United States Patent
Mao et al.

(10) Patent No.: US 11,441,165 B2
(45) Date of Patent: Sep. 13, 2022

(54) BIOSYNTHETIC PRODUCTION OF STEVIOL GLYCOSIDES REBAUDIOSIDE J AND REBAUDIOSIDE N

(71) Applicant: Conagen Inc., Bedford, MA (US)

(72) Inventors: Guohong Mao, Burlington, MA (US); Michael Batten, Westford, MA (US); Phillip Hunt, Tewksbury, MA (US); Oliver (Xiaodan) Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 17/109,473

(22) Filed: Dec. 2, 2020

(65) Prior Publication Data

US 2021/0189448 A1 Jun. 24, 2021

Related U.S. Application Data

(60) Division of application No. 16/679,032, filed on Nov. 8, 2019, now Pat. No. 10,883,130, which is a continuation of application No. PCT/US2019/021876, filed on Mar. 12, 2019.

(60) Provisional application No. 62/695,252, filed on Jul. 9, 2018, provisional application No. 62/682,260, filed on Jun. 8, 2018, provisional application No. 62/641,590, filed on Mar. 12, 2018.

(51) Int. Cl.
*C12P 19/56* (2006.01)
*C12N 15/82* (2006.01)
*C12N 9/10* (2006.01)

(52) U.S. Cl.
CPC ............ *C12P 19/56* (2013.01); *C12N 9/1081* (2013.01); *C12N 15/8245* (2013.01); *C12Y 204/01013* (2013.01); *C12Y 204/99* (2013.01)

(58) Field of Classification Search
CPC ... C12P 19/56; C12N 9/1081; C12N 15/8245; C12N 9/1051; C12Y 204/01013; C12Y 204/99; C12Y 204/01; A23L 27/36
See application file for complete search history.

(56) References Cited

U.S. PATENT DOCUMENTS

| | | | |
|---|---|---|---|
| 8,791,253 B2 | 7/2014 | Prakash et al. |
| 9,631,215 B2 | 4/2017 | Houghton-Larsen et al. |
| 9,783,566 B2 | 10/2017 | Mao et al. |
| 9,908,913 B2 | 3/2018 | Mao et al. |
| 9,957,540 B2 | 5/2018 | Mikkelsen et al. |
| 10,435,730 B2 | 10/2019 | Houghton-Larsen et al. |
| 10,463,062 B2 | 11/2019 | Philippe et al. |
| 10,570,163 B2 | 2/2020 | Mao et al. |
| 10,724,062 B2 | 7/2020 | Mao et al. |
| 10,883,130 B2 | 1/2021 | Mao et al. |
| 2006/0143729 A1 | 6/2006 | Alexandrov et al. |
| 2012/0107362 A1 | 5/2012 | Hofmann et al. |
| 2014/0329281 A1 | 11/2014 | Houghton-Larsen et al. |
| 2014/0357588 A1 | 12/2014 | Markosyan et al. |
| 2017/0112176 A1 | 4/2017 | Markosyan et al. |
| 2017/0275666 A1 | 9/2017 | Prakash et al. |
| 2017/0303865 A1 | 10/2017 | Kojima et al. |
| 2017/0321238 A1 | 11/2017 | Houghton-Larsen et al. |
| 2017/0332673 A1 | 11/2017 | Philippe et al. |
| 2017/0362267 A1 | 12/2017 | Mao et al. |
| 2018/0163244 A1 | 6/2018 | Anderson et al. |
| 2019/0338332 A1 | 11/2019 | Tao et al. |
| 2020/0002742 A1 | 1/2020 | Mao et al. |
| 2020/0087695 A1 | 3/2020 | Mao et al. |

FOREIGN PATENT DOCUMENTS

WO WO 2015/171555 A1 11/2015
WO WO 2016/028899 A1 2/2016

OTHER PUBLICATIONS

PCT/2019/21876, Jul. 17, 2019, International Search Report and Written Opinion.
PCT/2019/21876, Sep. 24, 2020, International Preliminary Report on Patentability.
U.S. Appl. No. 16/506,892, filed Jul. 9, 2019, Mao et al.
Branden et al., Introduction to Protein Structure, Garland Publishing Inc., New York, p. 247, 1991.
Chaturvedula et al., Isolation, NMR Spectral Analysis and Hydrolysis Studies of a Hepta Pyranosyl Diterpene Glycoside from Stevia rebaudiana Bertoni. Biomolecules. Sep. 30, 2013;3(4):733-40. doi: 10.3390/biom3040733.
Sadowski et al., The Sequence-Structure Relationship and Protein Function Prediction. Curr Opin Struct Biol. Jun. 2009;19(3):357-62. doi: 10.1016/j.sbi.2009.03.008. Epub May 4, 2009.
Seffernick et al., Melamine Deaminase and Atrazine Chlorohydrolase: 98 Percent Identical but Functionally Different. J Bacteriol. Apr. 2001;183(8):2405-10. doi: 10.1128/JB.183.8.2405-2410.2001.
Tang et al., Identification of Dehalobacter Reductive Dehalogenases That Catalyse Dechlorination of Chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Witkowski et al., Conversion of a Beta-Ketoacyl Synthase to a Malonyl Decarboxylase by Replacement of the Active-Site Cysteine With Glutamine. Biochemistry. Sep. 7, 1999;38(36):11643-50. doi: 10.1021/bi990993h.
U.S. Appl. No. 17/570,544, filed Jan. 7, 2022, Mao et al.

*Primary Examiner* — Delia M Ramirez
(74) *Attorney, Agent, or Firm* — Wolf, Greenfield & Sacks, P.C.; W. John Keyes

(57) ABSTRACT

The present disclosure relates to the production of steviol glycosides rebaudioside J and rebaudioside N through the use of rebaudioside A as a substrate and a biosynthetic pathway involving various 1,2 RhaT-rhamnosyltransferases.

17 Claims, 9 Drawing Sheets

Specification includes a Sequence Listing.

BIOSYNTHETIC PRODUCTION OF STEVIOL GLYCOSIDES REBAUDIOSIDE J AND REBAUDIOSIDE N

CROSS-REFERENCE TO RELATED APPLICATIONS

This application is a divisional of U.S. application Ser. No. 16/679,032, filed on Nov. 8, 2019, now U.S. Pat. No. 10,883,130, issued Jan. 5, 2021, which is a continuation of International Application No. PCT/US2019/021876, filed on Mar. 12, 2019, which claims priority to U.S. Provisional Application No. 62/641,590, filed on Mar. 12, 2018, U.S. Provisional-Application No. 62/682,260, filed on Jun. 8, 2018, and U.S. Provisional Application No. 62/695,252, filed on Jul. 9, 2018, the contents of each of which are incorporated by reference herein in their entirety.

FIELD OF THE INVENTION

The present disclosure generally relates to the biosynthesis of steviol glycosides. More specifically, the present disclosure relates to biocatalytic processes for preparing compositions comprising rebaudioside J ("Reb J") and/or rebaudioside N ("Reb N"), as well as recombinant polypeptides having enzymatic activity useful in the relevant biosynthetic pathways for producing Reb J and/or Reb N.

BACKGROUND OF THE INVENTION

Steviol glycosides are a class of compounds found in the leaves of *Stevia rebaudiana* plant that can be used as high intensity, low-calorie sweeteners. These naturally occurring steviol glycosides share the same basic diterpene structure (steviol backbone) but differ in the number and type of carbohydrate residues (e.g., glucose, rhamnose, and xylose residues) at the C13 and C19 positions of the steviol backbone. Interestingly, these variations in sugar 'ornamentation' of the basic steviol structure often dramatically and unpredictably affect the properties of the resulting steviol glycoside. The properties that are affected can include, without limitation, the overall taste profile, the presence and extent of any off-flavors, crystallization point, "mouth feel", solubility and perceived sweetness among other differences. Steviol glycosides with known structures include stevioside, rebaudioside A, rebaudioside B, rebaudioside C, rebaudioside D, rebaudioside E, rebaudioside F, rebaudioside M, rebaudioside J, rebaudioside N, and dulcoside A.

On a dry weight basis, stevioside, rebaudioside A, rebaudioside C, and dulcoside A account for approximately 9.1%, 3.8%, 0.6%, and 0.3%, respectively, of the total weight of all steviol glycosides found in wild type *stevia* leaves. Other steviol glycosides such as Reb J and Reb N are present in significantly lower amounts. Extracts from the *Stevia rebaudiana* plant are commercially available. In such extracts, stevioside and rebaudioside A typically are the primary components, while the other known steviol glycosides are present as minor or trace components. The actual content level of the various steviol glycosides in any given *stevia* extract can vary depending on, for example, the climate and soil in which the *stevia* plants are grown, the conditions under which the *stevia* leaves are harvested, and the processes used to extract the desired steviol glycosides. To illustrate, the amount of rebaudioside A in commercial preparations can vary from about 20% to more than about 90% by weight of the total steviol glycoside content, while the amount of rebaudioside B, rebaudioside C, and rebaudioside D, respectively, can be about 1-2%, about 7-15%, and about 2% by weight of the total steviol glycoside content. In such extracts, rebaudioside J and rebaudioside N typically account for, individually, less than 0.5% by weight of the total steviol glycoside content.

As natural sweeteners, different steviol glycosides have different degrees of sweetness, mouth feel, and aftertastes. The sweetness of steviol glycosides is significantly higher than that of table sugar (i.e., sucrose). For example, stevioside itself is 100-150 times sweeter than sucrose but has a bitter aftertaste as noted in numerous taste tests, while rebaudiosides A and E are 250-450 times sweeter than sucrose and the aftertaste profile is much better than stevioside. However, these steviol glycosides themselves still retain a noticeable aftertaste. Accordingly, the overall taste profile of any *stevia* extract is profoundly affected by the relative content of the various steviol glycosides in the extract, which in turn may be affected by the source of the plant, the environmental factors (such as soil content and climate), and the extraction process. In particular, variations of the extraction conditions can lead to inconsistent compositions of the steviol glycosides in the *stevia* extracts, such that the taste profile varies among different batches of extraction productions. The taste profile of *stevia* extracts also can be affected by plant-derived or environment-derived contaminants (such as pigments, lipids, proteins, phenolics, and saccharides) that remain in the product after the extraction process. These contaminants typically have off-flavors undesirable for the use of the *stevia* extract as a sweetener. In addition, the process of isolating individual or specific combinations of steviol glycosides that are not abundant in *stevia* extracts can be cost- and resource-wise prohibitive.

Further, the extraction process from plants typically employs solid-liquid extraction techniques using solvents such as hexane, chloroform, and ethanol. Solvent extraction is an energy-intensive process, and can lead to problems relating to toxic waste disposal. Thus, new production methods are needed to both reduce the costs of steviol glycoside production as well as to lessen the environmental impact of large scale cultivation and processing.

Accordingly, there is a need in the art for novel preparation methods of steviol glycosides, particularly minor steviol glycosides such as Reb J and Reb N, that can yield products with better and more consistent taste profiles. More preferably, such preparation methods can make use of more abundant steviol glycosides such as Reb A, to reduce the cost of production.

SUMMARY OF THE INVENTION

The present disclosure encompasses, in some embodiments, a method of preparing Reb J from Reb A as well as the preparation of Reb N from Reb A through the intermediate of Reb J. In some embodiments, the present disclosure provides a method of preparing Reb N from Reb I as well as the preparation of Reb N from Reb A through the intermediate of Reb I.

In one embodiment, the current disclosure provides for the production of steviol glycoside rebaudioside J "Reb J", or 13-[(2-O-β-D-glucopyranosyl-3-O-β-D-glucopyranosyl-β-D-glucopyranosyl)oxy] ent-kaur-16-en-19-oic acid-[(2-O-α-L-rhamnopyranosyl-β-D-glucopyranosyl) ester], by various 1,2-rhamnosyltransferase enzymes described herein from Reb A. FIG. 1 shows the chemical structure of Reb J.

In another embodiment, the current disclosure provides for the production of steviol glycoside rebaudioside N "Reb N", or 13-[(2-O-β-D-glucopyranosyl-3-O-β-D-glucopyranosyl-β-D-glucopyranosyl)oxy] ent-kaur-16-en-19-oic acid-[(2-O-α-L-rhamnopyranosyl-3-O-β-D-glucopyranosyl-β-D-glucopyranosyl) ester] by various UDP-glycosyltransferases described herein from Reb J. FIG. 2 shows the chemical structure of Reb N.

The current method provides an approach for the synthesis of specific steviol glycosides using certain specific synthetic pathways.

In terms of product/commercial utility there are several dozen products containing steviol glycosides on the market in the United States and can be used in everything from foods, beverages, and dietary supplements to analgesics and pest repellents. Products containing steviol glycosides can be liquids, granular formulations, gels or aerosols.

Provided herein, inter alia, are biosynthetic methods of preparing a rebaudioside, such as rebaudioside N, the methods comprising reacting a steviol glycoside composition with a rhamnose donor moiety in the presence of a first recombinant polypeptide having 1,2-rhamnosytransferase activity; wherein the first recombinant polypeptide comprises an amino acid sequence having at least 80% (e.g., at least 80%. at least 85%, at least 90%, at least 95%, at least 96%, at least 97%, at least 98%, at least 99% or 100%) sequence identity to SEQ ID NO: 3, SEQ ID NO: 9, or SEQ ID NO: 19.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 3.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 9.

In some embodiments, the first recombinant polypeptide comprises an amino acid sequence having at least 80%, at least 85%, at least 90%, at least 95%, at least 96%, at least 97%, at least 98%, at least 99%, or 100% identity to SEQ ID NO: 19.

In some embodiments, biosynthetic methods provided herein comprise expressing the first recombinant polypeptide in a transformed cellular system. In some embodiments, the transformed cellular system is selected from the group consisting of a yeast, a non-steviol glycoside producing plant, an alga, a fungus, and a bacterium. In some embodiments, the bacterium or yeast is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansemla; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium*.

In some embodiments, biosynthetic methods provided herein comprise a reacting step that is performed in the transformed cellular system. In other embodiments, the reacting step can be performed in vitro. In some embodiments, biosynthetic methods comprise isolating the first recombinant polypeptide from the transformed cellular system and the reacting step can be performed in vitro.

In some embodiments, the rhamnose donor is rhamnose. In some embodiments, the rhamnose donor is L-rhamnose. In some embodiments, the rhamnose donor moiety is UDP-L-rhamnose.

In some embodiments, the steviol glycoside composition comprises rebaudioside A and the reacting step leads to the production of rebaudioside J.

In some embodiments, biosynthetic methods provided herein further comprise reacting the rebaudioside J with a glucose donor moiety in the presence of a second recombinant polypeptide having glucosytransferase activity. In some embodiments, the glucose donor moiety is generated in situ.

In some embodiments, the second recombinant polypeptide has both glucosyltransferase activity and sucrose synthase activity. In some embodiments, the second recombinant polypeptide comprises an amino acid sequence having at least 80% (e.g., at least 80%, at least 85%, at least 90%, at least 95%, at least 96%, at least 97%, at least 98%, at least 99% or 100%) sequence identity to SEQ ID NO: 7, SEQ ID NO: 11, SEQ ID NO: 13, or SEQ ID NO: 15.

In some embodiments, the second recombinant polypeptide comprises an amino acid sequence having at least 80%, at least 85%, at least 90%, at least 95%, at least 96%, at least 97%, at least 98%, at least 99/a, or 100% identity to SEQ ID NO: 7.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 11.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 13.

In some embodiments, the second recombinant polypeptide comprises an amino acid sequence having at least 80%, at least 85%, at least 90%, at least 95%, at least 96%, at least 97%, at least 98%, at least 99%, or 100% identity to SEQ ID NO: 15.

In some embodiments, biosynthetic methods provided herein further comprise reacting the rebaudioside J with a glucose donor moiety in the presence of a third recombinant polypeptide having sucrose synthase activity.

In some embodiments, the steviol glycoside composition can include rebaudioside I. In some embodiments, the rebaudioside I can be prepared by reacting a steviol glycoside composition comprising rebaudioside A with a glucose donor moiety in the presence of a second recombinant polypeptide having glucosyltransferase activity.

In some embodiments, biosynthetic methods provided herein further comprise reacting the steviol glycoside composition comprising rebaudioside A with a glucose donor moiety in the presence of a third recombinant polypeptide having sucrose synthase activity.

Also provided herein, inter alia, are biosynthetic methods of preparing a rebaudioside, such as rebaudioside J, the methods comprising reacting a steviol glycoside composition comprising rebaudioside A with a rhamnose donor moiety in the presence of a recombinant polypeptide having 1,2-rhamnosytransferase activity; wherein said recombinant polypeptide comprises an amino acid sequence having at least 80% (e.g., at least 80%, at least 85%, at least 90%, at least 95%, at least 96%, at least 97%, at least 98%, at least 99% or 100%) sequence identity to SEQ ID NO: 3, SEQ ID NO: 9, or SEQ ID NO: 19.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 3.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 9.

In some embodiments, the recombinant polypeptide having 1,2-rhamnosytransferase activity comprises an amino acid sequence having at least 80%, at least 85%, at least 90%, at least 95%, at least 96%, at least 97%, at least 98%, at least 99%, or 100% identity to SEQ ID NO: 19.

Aspects of the present disclosure also provide a rebaudioside obtainable by or produced by any biosynthetic method described herein, including any of the above-mentioned embodiments.

Aspects of the present disclosure also provide a nucleic acid encoding a polypeptide as described herein. In some embodiments, the nucleic acid comprises a sequence encoding a polypeptide comprising an amino acid sequence having at least 80%, at least 85%, at least 90%, at least 95%, at least 96%, at least 97%, at least 98%, at least 99%, or 100% identity to SEQ ID NO: 3, SEQ ID NO: 9, or SEQ ID NO: 19. In some embodiments, the nucleic acid comprises a sequence having at least 80%, at least 85%, at least 90%, at least 95%, at least 96%, at least 97%, at least 98%, at least 99%, or 100% identity to SEQ ID NO: 4, SEQ ID NO: 10, or SEQ ID NO: 20. In some embodiments, the nucleic acid comprises the sequence of SEQ ID NO: 4. In some embodiments, the nucleic acid comprises the sequence of SEQ ID NO: 10. In some embodiments, the nucleic acid comprises the sequence of SEQ ID NO: 20. In some embodiments, the nucleic acid is a plasmid or other vector.

Aspects of the present disclosure also provide a cell comprising a nucleic acid described herein, including any of the above-mentioned embodiments.

Other aspects of the present disclosure provide a composition comprising at least one polypeptide comprising an amino acid sequence having at least 80%, at least 85%, at least 90%, at least 95%, at least 96%, at least 97%, at least 98%, at least 99% or 100% identity to SEQ ID NO: 3, SEQ ID NO: 9, or SEQ ID NO: 19. In some embodiments, the composition comprises at least one polypeptide comprising the sequence of SEQ ID NO: 3. In some embodiments, the composition comprises at least one polypeptide comprising the sequence of SEQ ID NO: 9. In some embodiments, the composition comprises at least one polypeptide comprising the sequence of SEQ ID NO: 19. In some embodiments, the composition is an in vitro reaction mixture, e.g., comprising a rhamnose donor moiety as described herein and a steviol glycoside composition as described herein.

Aspects of the present disclosure provide a cell comprising at least one polypeptide comprising an amino acid sequence having at least 80%, at least 85%, at least 90%, at least 95%, at least 96%, at least 97%, at least 98%, at least 99%, or 100% identity to SEQ ID NO: 3, SEQ ID NO: 9, or SEQ ID NO: 19. In some embodiments, the cell comprises at least one polypeptide comprising the sequence of SEQ ID NO: 3. In some embodiments, the cell comprises at least one polypeptide comprising the sequence of SEQ ID NO: 9. In some embodiments, the cell comprises at least one polypeptide comprising the sequence of SEQ ID NO: 19. In some embodiments, the cell is a yeast cell, a non-steviol glycoside producing plant cell, an algal cell, a fungal cell, or a bacterial cell. In some embodiments, the bacterium or yeast cell is selected from the group consisting of *Escherichia*; *Salmonella*; *Bacillus*; *Acinetobacter*; *Streptomyces*; *Corynebacterium*; *Methylosiums*; *Methylomonas*; *Rhodococcus*; *Pseudomonas*; *Rhodobacter*; *Synechocystis*; *Saceharomyces*; *Zygosaceharomyces*; *Kluyveromyces*; *Candida*; *Hansemla*; *Debaryomyces*; *Mucor*; *Pichia*; *Torlopsis*; *Aspergillus*; *Arthrobotilvs*; *Brevibacteria*; *Microbacterium*; *Arthrobacter*; *Citrobacter*; *Klebsiella*; *Pantoea*; and *Clostridium*. In some embodiments, the cell further comprises a second polypeptide having glucosytransferase activity or glucosyltransferase activity and sucrose synthase activity as described herein, such as a second polypeptide comprising an amino acid sequence having at least 80% (e.g., at least 80%, at least 85%, at least 90%, at least 95%, at least 96%, at least 97%, at least 98%, at least 99% or 100%) sequence identity to SEQ ID NO: 7, SEQ ID NO: 11, SEQ ID NO: 13, or SEQ ID NO: 15.

As for the cellular system in the embodiment, it can be selected from the group consisting of one or more bacteria, one or more yeasts, and a combination thereof, or any cellular system that would allow the genetic transformation with the selected genes and thereafter the biosynthetic production of the desired steviol glycosides. In a most preferred microbial system, *E. coli* are used to produce the desired steviol glycoside compounds.

In some embodiments, the disclosure provides a mutant of EUI1 enzyme comprising the amino acid sequence of SEQ ID NO: 3 and identified as EUCP1. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 3.

In some embodiments, the disclosure provides a DNA molecule having a sequence corresponding to EUCP1 and comprising SEQ ID NO: 4. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 4.

In some embodiments, the disclosure provides a mutant of the EU11 enzyme comprising the amino acid sequence of SEQ ID NO: 1. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 1.

In some embodiments, the disclosure provides a DNA molecule having a sequence corresponding to EU11 and comprising SEQ ID NO: 2. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 2.

In some embodiments, the disclosure provides an enzyme referred herein as UGT2E-B comprising the amino acid sequence of SEQ ID NO: 9. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 9.

In some embodiments, the disclosure provides a DNA molecule having a sequence corresponding to UGT2E-B and comprising SEQ ID NO: 10. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 10.

In some embodiments, the disclosure provides an enzyme referred herein as NX114 comprising the amino acid sequence of SEQ ID NO: 19. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 19.

In some embodiments, the disclosure provides a DNA molecule having a sequence corresponding to NX114 and comprising SEQ ID NO: 20. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 20.

In some embodiments, the disclosure provides a microbial host cell comprising a vector capable of producing one or more enzymes described herein. In certain embodiments, the enzyme can be selected from the group consisting of EUCP1 [SEQ ID. NO. 3], UGT2E-B [SEQ ID. No. 9], and NX114 [SEQ ID NO. 19]. In some embodiments, the enzyme can be selected from the group consisting of CP1 [SEQ ID NO. 11] and CP2 [SEQ ID NO. 13]. In some embodiments, the enzyme can be a fusion enzyme referred herein as GS [SEQ ID No. 15]. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium* (e.g., *Clostridium acetobutylicum*). In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum* yulgare; switchgrass (*Panicum vigratum*); *Brachypodium* spp.; *Brassica* spp.; and *Crambe abyssinica*.

In some embodiments, the disclosure provides a method of producing rebaudioside J, the method comprising incubating a substrate with a recombinant polypeptide comprising an amino acid sequence having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the recombinant polypeptide is a 1,2 rhamnosyltranferase having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the substrate is selected from the group consisting of rubusoside, stevioside or rebaudioside A and combinations thereof.

In some embodiments, the disclosure provides a sweetener comprising Reb J produced by any of the embodiments of the above-mentioned method.

In some embodiments, the disclosure provides a method of producing rebaudioside N, the method comprising incubating a substrate with a first recombinant polypeptide comprising an amino acid sequence having at least 80% (e.g., at least 80%, at least 85%, at least 90%, at least 95%, at least 96%, at least 97%, at least 98%, at least 99% or 100%) identity to SEQ ID NO: 3, SEQ ID NO: 9, or SEQ ID NO: 19. In some embodiments, the substrate is selected from the group consisting of Reb J, Reb I, Reb A, stevioside or rubusoside and combinations thereof. In some embodiments, the substrate comprises Reb J. In other embodiments, the substrate comprises Reb I. In some embodiments, the method further comprises incubating a second recombinant polypeptide having glucosyltransferase activity and optionally a recombinant sucrose synthase, with the substrate and the first recombinant polypeptide.

In some embodiments, the disclosure provides a sweetener comprising Reb N produced by any of the embodiments of the above-mentioned method.

In some embodiments, the disclosure provides a method for synthesizing rebaudioside N from rebaudioside J, the method comprising: preparing a reaction mixture comprising rebaudioside J, a glucose donor moiety selected from the group consisting of sucrose, uridine diphosphate (UDP) and uridine diphosphate glucose (UDP-glucose), and a UGT enzyme, incubating the reaction mixture for a sufficient time to produce rebaudioside N, wherein a glucose is covalently coupled to the rebaudioside J to produce rebaudioside N. In various embodiments, the UGT enzyme can be a polypeptide comprising an amino acid sequence having at least 80% sequence identity to UGT76G1 [SEQ ID No. 7], CP1 [SEQ ID No. 11], CP2 [SEQ ID No. 13], or GS [SEQ ID No. 15]. In some embodiments, the method further comprises adding a sucrose synthase to the reaction mixture. In some embodiments, the sucrose synthase is selected from the group consisting of an *Arabidopsis* sucrose synthase 1, an *Arabidopsis* sucrose synthase 3 and a *Vigna* radiate sucrose synthase. In some embodiments, the sucrose synthase is an *Arabidopsis thaliana* sucrose synthase 1 (SEQ ID NO: 17).

In some embodiments, said Reb N is greater than 70% (e.g., greater than 80%, greater than 85%, greater than 90%, greater than 95%, greater than 96%, greater than 97%, greater than 98%, or greater than 99%) pure.

In some embodiments, the disclosure provides a host cell comprising a vector capable of producing an enzyme wherein the amino acid sequence corresponds to SEQ ID NO: 3, SEQ ID NO: 9, or SEQ ID NO: 19. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum* yulgare; switchgrass (*Panicum vigratum*); *Brachypodium* spp.; *Brassica* spp.; and *Crambe abyssinica*.

In some embodiments, the disclosure provides a beverage product comprising: up to about 125 ppm Rebaudioside N; and at least one non-nutritive sweetener selected from the group consisting of Reb J; Reb W; Reb V; Reb D4, Reb E, and Reb M, and combinations thereof, wherein the at least one non-nutritive sweetener is present in a concentration from about 30 ppm to about 600 ppm. In some embodiments, the at least one non-nutritive sweetener is selected from the group consisting of Reb J; Reb W; Reb V; Reb D4, Reb E, and Reb M, and combinations thereof, and wherein the Reb N and the at least one non-nutritive sweetener are present in a weight ratio of about 1:5.

In some embodiments, the disclosure provides a GS fusion enzyme comprising a first domain having an amino acid sequence at least 90% identical to UGT76G1 and a second domain having an amino acid sequence at least 90% identical to AtSUS1. The GS fusion enzyme can have an amino acid sequence comprising SEQ ID NO: 15. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 15.

In some embodiments, the disclosure provides a DNA molecule having a sequence corresponding to GS and comprising SEQ ID NO: 16. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 16.

In some embodiments, the disclosure provides a UDP-glycosyltransferase comprising the UGT2E-B enzyme and having the amino acid sequence of SEQ ID NO: 9. In some embodiments, the disclosure provides a recombinant polypeptide comprising an amino acid sequence having at least 90% (e.g., at least 90%, at least 95%, at least 96%, at least 97%, at least 98%, at least 99% or 100%) identity to SEQ ID NO: 9.

In some embodiments, the disclosure provides a DNA molecule having a sequence corresponding to UGT2E-B and comprising SEQ ID NO: 10. In some embodiments, the disclosure provides a nucleic acid molecule having a sequence having at least 90% (e.g., at least 90%, at least 95%, at least 96%, at least 97%, at least 98%, at least 99% or 100%) identity to SEQ ID NO: 10.

In some embodiments, the disclosure provides a microbial host cell comprising a vector capable of producing the UGT2E-B enzyme. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum* yulgare; switchgrass (*Panicum vigratum*); *Brachypodium* spp.; *Brassica* spp.; and, *Crambe abyssinica*.

In some embodiments, the disclosure provides a method of producing rebaudioside N, the method comprising incubating a substrate with a recombinant polypeptide comprising an amino acid sequence having at least 80% identity to SEQ ID NO: 11 or SEQ ID NO: 13 or SEQ ID NO: 15. In some embodiments, the substrate is selected from the group consisting of Reb J, Reb A., stevioside or rubusoside and combinations thereof. In some embodiments, the method further comprises incubating a recombinant sucrose synthase with the substrate and the recombinant polypeptide.

In some embodiments, the disclosure provides a host cell comprising a vector capable of producing the CP1 and CP2 enzymes wherein the amino acid sequence corresponds to SEQ ID NOs: 11 and 13, respectively. In some embodiments, the host cell is selected from the group consisting of a bacterium, a yeast, a filamentous fungus, a cyanobacteria alga and a plant cell. In some embodiments, the host cell is selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea; Corynebacterium; Clostridium*. In some embodiments, the host cell is a cell isolated from plants selected from the group consisting of soybean; rapeseed; sunflower; cotton; corn; tobacco; alfalfa; wheat; barley; oats; sorghum; rice; broccoli; cauliflower; cabbage; parsnips; melons; carrots; celery; parsley; tomatoes; potatoes; strawberries; peanuts; grapes; grass seed crops; sugar beets; sugar cane; beans; peas; rye; flax; hardwood trees; softwood trees; forage grasses; *Arabidopsis thaliana*; rice (*Oryza sativa*); *Hordeum* yulgare; switchgrass (*Panicum vigratum*); *Brachypodium* spp.; *Brassica* spp.; and, *Crambe abyssinica*.

In some embodiments, the disclosure provides a mutant enzyme comprising the amino acid sequence of SEQ ID NO: 11 and identified as CP1.

In some embodiments, the disclosure provides a mutant enzyme comprising the amino acid sequence of SEQ ID NO: 13 and identified as CP2.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

DETAILED DESCRIPTION

Figure 1:
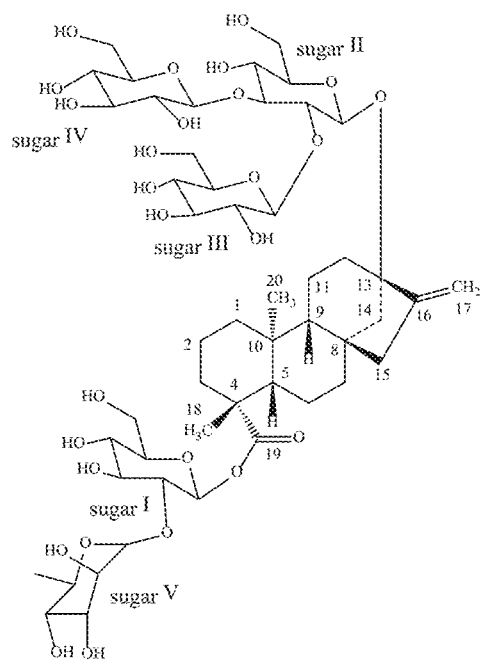
FIG. 1 shows the chemical structure of rebaudioside J ("Reb J").
Figure 2:
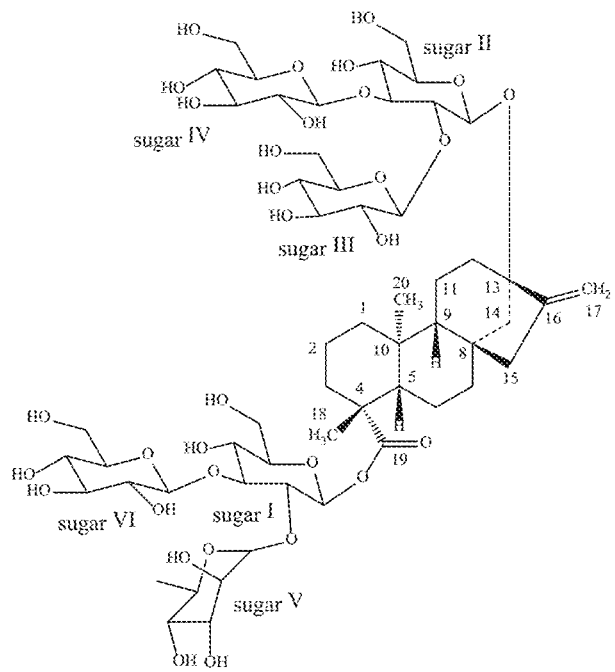
FIG. 2 shows the chemical structure of rebaudioside N ("Reb N").

Explanation of Terms Used Herein:

Steviol Glycosides are a class of chemical compounds responsible for the sweet taste of the leaves of the South American plant *Stevia rebaudiana* (*Asteraceae*), and can be used as sweeteners in food, feed and beverages.

Definitions:

Cellular system is any cells that provide for the expression of ectopic proteins. It included bacteria, yeast, plant cells and animal cells. It includes both prokaryotic and eukaryotic cells. It also includes the in vitro expression of proteins based on cellular components, such as ribosomes.

Coding sequence is to be given its ordinary and customary meaning to a person of ordinary skill in the art and is used without limitation to refer to a DNA sequence that encodes for a specific amino acid sequence.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current disclosure a yeast as claimed herein are eukaryotic, single-celled microorganisms classified as members of the fungus kingdom. Yeasts are unicellular organisms which evolved from multicellular ancestors but with some species useful for the current disclosure being those that have the ability to develop multicellular characteristics by forming strings of connected budding cells known as pseudo hyphae or false hyphae.

UGT Names. The names of the UGT enzymes used in the present disclosure are consistent with the nomenclature system adopted by the UGT Nomenclature Committee (Mackenzie et al., "*The UDP glycosyltransferase gene super family: recommended nomenclature updated based on evolutionary divergence*," PHARMACOGENETICS, 1997, vol. 7, pp. 255-269), which classifies the UGT genes by the combination of a family number, a letter denoting a subfamily, and a number for an individual gene. For example, the name "UGT76G1" refers to a UGT enzyme encoded by a gene belonging to UGT family number 76 (which is of plant origin), subfamily G, and gene number I.

Structural Terms:

As used herein, the singular forms "a, an" and "the" include plural references unless the content clearly dictates otherwise.

To the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration". Any embodiment described herein as "exemplary" is not necessarily to be construed as preferred or advantageous over other embodiments.

The term "complementary" is to be given its ordinary and customary meaning to a person of ordinary skill in the art and is used without limitation to describe the relationship between nucleotide bases that are capable to hybridizing to one another. For example, with respect to DNA, adenosine is complementary to thymine and cytosine is complementary to guanine. Accordingly, the subjection technology also includes isolated nucleic acid fragments that are complementary to the complete sequences as reported in the accompanying Sequence Listing as well as those substantially similar nucleic acid sequences The terms "nucleic acid" and "nucleotide" are to be given their respective ordinary and customary meanings to a person of ordinary skill in the art and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is to be given its ordinary and customary meaning to a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein means a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxy inosine residues. A nucleic acid sequence and all of its degenerate variants will express the same amino acid or polypeptide.

The terms "polypeptide," "protein,' and "peptide" are to be given their respective ordinary' and customary meanings to a person of ordinary skill in the art; the three terms are sometimes used interchangeably and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term 'polypeptide" as used herein refers to peptides, polypeptides, and proteins, unless otherwise noted. The terms "protein," "polypeptide," and "peptide" are used interchangeably herein when refe1Ting to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are to be given their ordinary and customary meanings to a person of ordinary skill in the art and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full-length polypeptide or protein, and has substantially the same biological activity, or carries out substantially the same function as the full-length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from super families and homologous polynucleotides or proteins from different species (Reeck et al., CELL 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 900 at least 91%, at least 92%, at least 93%, at least 94%, at least 95%, at least 96%, at least 97%, at least 98%, at least 99%, and even 100% identical.

"Suitable regulatory sequences" is to be given its ordinary and customary meaning to a person of ordinary skill in the art and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is to be given its ordinary and customary meaning to a person of ordinary skill in the art and is used without limitation to refer to a DNA sequence capable of controlling the expression of a coding sequence or functional RNA. In general, a coding sequence is located 3' to a promoter sequence. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters, which cause a gene to be expressed in most cell types at most times, are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it can affect the expression of that coding sequence (i.e., that the coding sequence is under the transcriptional control of the promoter). Coding sequences can be operably linked to regulatory sequences in sense or antisense orientation.

The term "expression" as used herein, is to be given its ordinary and customary meaning to a person of ordinary skill in the art and is used without limitation to refer to the transcription and stable accumulation of sense (mRNA) or antisense RNA derived from the nucleic acid fragment of the subject technology. "Over-expression" refers to the production of a gene product in transgenic or recombinant organisms that exceeds levels of production in normal or non-transformed organisms.

"Transformation" is to be given its ordinary and customary meaning to a person of reasonable skill in the craft and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "transformed".

The terms "transformed," "transgenic," and "recombinant," when used herein in connection with host cells, are to be given their respective ordinary and customary meanings to a person of ordinary skill in the art and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are to be given their ordinary and customary meanings to a person of ordinary skill in the art and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are to be given their respective ordinary and customary meanings to a person of ordinary skill in the art and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Figure 3A:
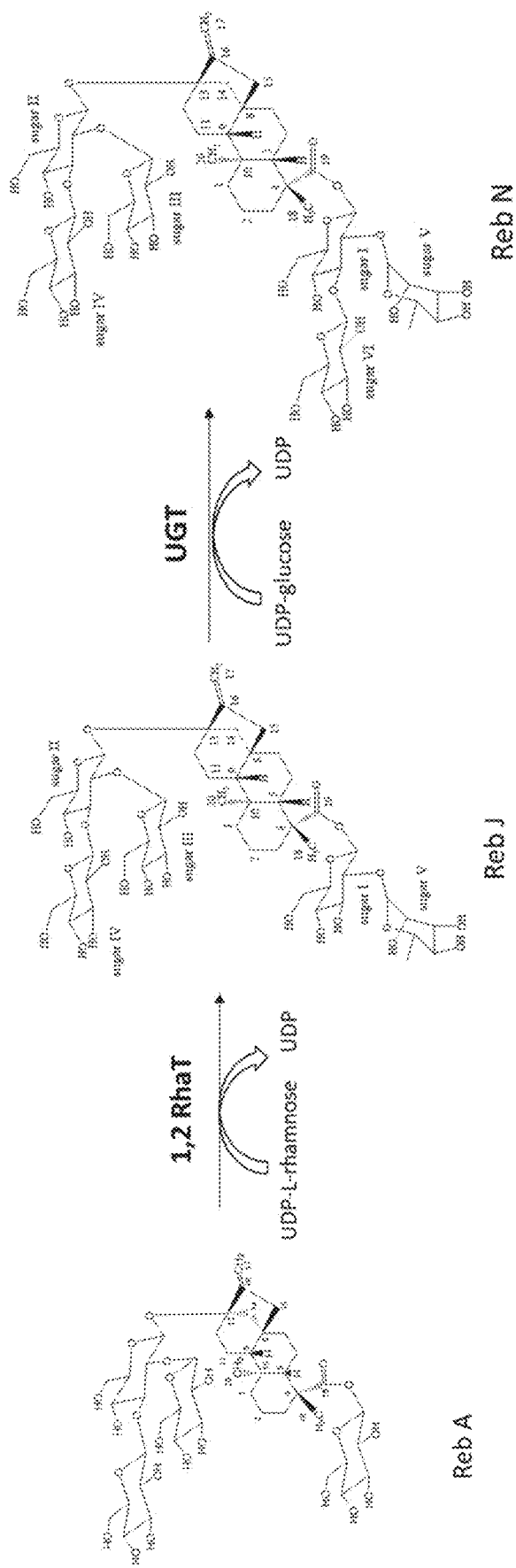
FIG. 3A illustrates the biosynthetic pathway for the production of Reb J and Reb N. More specifically, starting from rebaudioside A ("Reb A"), a 1,2 rhamnosyltransferase ("1,2 RhaT") can be used to produce Reb J by catalyzing the transfer of a rhamnose moiety from a UDP-rhamnose donor to the C-2' of the 19-O-glucose of the Reb A acceptor. In a subsequent reaction, a UDP-glycosytransferase ("UGT") can be used to produce Reb N from Reb J by catalyzing the transfer of a glucose moiety from a UDP-glucose donor to the C-3' of the 19-O-gluocose of the Reb J acceptor.
Figure 3B:
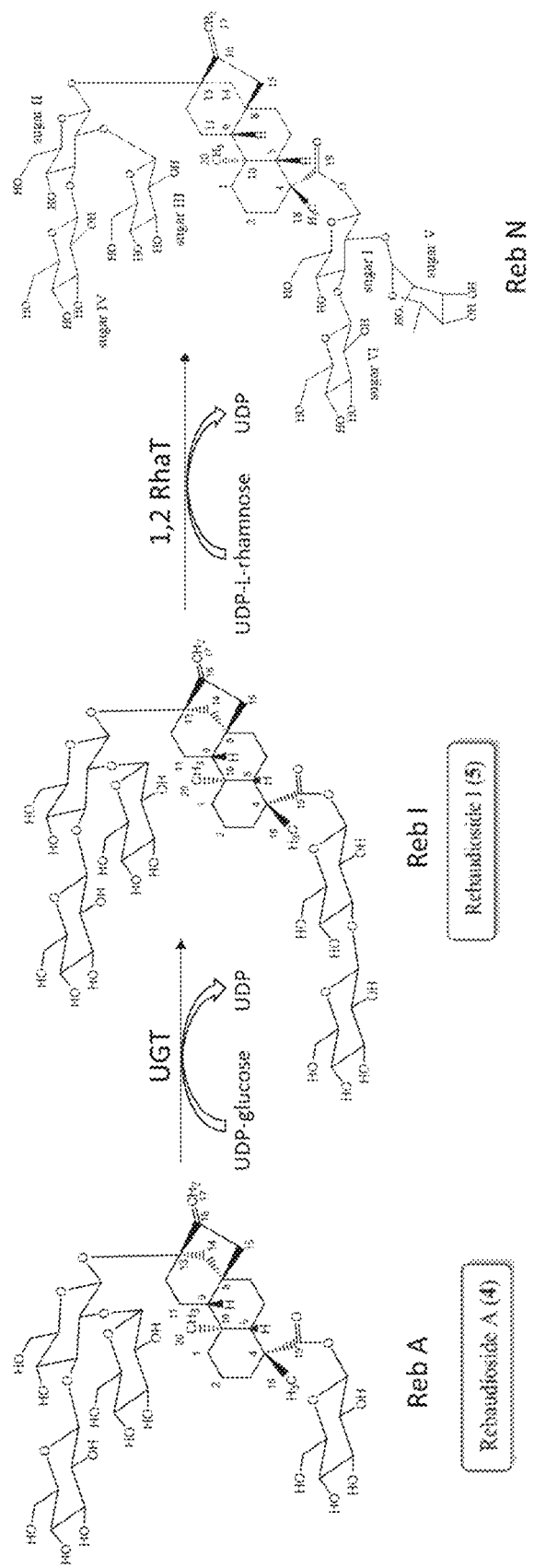
FIG. 3B shows the biosynthetic pathway for the production of Reb I from Reb A using a UGT. Reb I can then be converted to Reb N using a 1,2 RhaT.

The present disclosure relates, in some embodiments, to the production of a steviol glycoside of interest, Reb N, from Reb A using at least one novel UDP-rhamnosyltransferases (RhaT) described herein, which can transfer a rhamnose moiety from UDP-L-rhamnose to a steviol glycoside acceptor in a rhamnosylation reaction. Referring to FIG. 3, the synthetic pathway can involve rebaudioside J as an intermediate (FIG. 3A), or rebaudioside I as an intermediate (FIG. 3B). The subject technology provides, in some embodiments, recombinant polypeptides with UDP glycosyltransferase activities for synthesizing steviol glycosides. In some embodiments, the recombinant polypeptides can have 1,2-19-O-rhamnose glycosylation activity. In some embodiments, the recombinant polypeptides can have 1,3-19-O-glucose glycosylation activity. The recombinant polypeptide of the subject technology is useful for the biosynthesis of steviol glycoside compounds. In the present disclosure, UDP-rhamnosyltransferase (Rha T) refers to an enzyme that transfers a rhamnose sugar moiety from an activated donor molecule (typically UDP-L-rhamnose) to an acceptor steviol glycoside molecule. The 1,2 Rha T refers to an enzymatic activity that transfers a rhamnose moiety from UDP-L-rhamnose to the C-2' of the 19-O-glucose or the 13-0-glucose of steviol glycosides. The 1,2-19-O— rhamnose glycosylation activity refers to an enzymatic activity that transfers a rhamnose moiety to the C-2' of the 19-0 glucose moiety of a steviol glycoside such as rebaudioside A (to produce rebaudioside J) or rebaudioside I (to produce rebaudioside N). The 1,3-19-O-glucose glycosylation activity refers to an enzymatic activity that transfers a glucose moiety to the C-3' of the 19-0 glucose moiety of a steviol glycoside such as rebaudioside J (to produce rebaudioside N) or rebaudioside A (to produce rebaudioside I) (FIG. 3).

Synthetic Biology

Standard recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WIH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred materials and methods are described below.

The disclosure will be more fully understood upon consideration of the following non-limiting Examples. It should be understood that these Examples, while indicating preferred embodiments of the subject technology, are given by way of illustration only. From the above discussion and these Examples, one skilled in the art can ascertain the essential characteristics of the subject technology, and without departing from the spirit and scope thereof, can make various changes and modifications of the subject technology to adapt it to various uses and conditions.

Glycosylation is often considered a ubiquitous reaction controlling the bioactivity and storage of plant natural products. Glycosylation of small molecules is catalyzed by a superfamily of transferases in most plant species that have been studied to date. These glycosyltransferases (GTs) have been classified into over 60 families. Of these, the family of GT enzymes, also known as the UDP glycosyltransferases (UGTs) and UDP-rhamnosyltransferase, transfers sugar moieties to specific acceptor molecules. These are the molecules that transfer such sugar moieties in the steviol glycosides to help create various rebaudiosides. Each of these enzymes have their own activity profile and preferred structure locations where they transfer their activated sugar moieties.

Production Systems

Expression of proteins in prokaryotes is most often carried out in a bacterial host cell with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and, 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such vectors are within the scope of the present disclosure.

In an embodiment, the expression vector includes those genetic elements for expression of the recombinant polypeptide in bacterial cells. The elements for transcription and translation in the bacterial cell can include a promoter, a coding region for the protein complex, and a transcriptional terminator.

A person of ordinary skill in the art will be aware of the molecular biology techniques available for the preparation of expression vectors. The polynucleotide used for incorporation into the expression vector of the subject technology, as described above, can be prepared by routine techniques such as polymerase chain reaction (PCR).

Several molecular biology techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the polynucleotide of the subject technology to the expression vector. In an embodiment, the polynucleotide is generated by restriction endonuclease digestion. In an embodiment, the nucleic acid molecule is treated with bacteriophage T4 DNA polymerase or *E. coli* DNA polymerase I, enzymes that remove protruding, 3'-single-stranded termini with their 3'-5'-exonucleolytic activities and fill in recessed 3'-ends with their polymerizing activities, thereby generating blunt ended DNA segments. The blunt-ended segments are then incubated with a large molar excess of linker molecules in the presence of an enzyme that can catalyze the ligation of blunt-ended DNA molecules, such as bacteriophage T4 DNA ligase. Thus, the product of the reaction is a polynucleotide carrying polymeric linker sequences at its ends. These polynucleotides are then cleaved with the appropriate restriction enzyme and ligated to an expression vector that has been cleaved with an enzyme that produces termini compatible with those of the polynucleotide.

Alternatively, a vector having ligation-independent cloning (LIC) sites can be employed. The required PCR amplified polynucleotide can then be cloned into the LIC vector without restriction digest or ligation (Aslanidis and de Jong, NUCL. ACID. RES. 18 6069-74, (1990), Haun, et al, BIOTECHNIQUES 13, 515-18 (1992), which is incorporated herein by reference).

In an embodiment, to isolate and/or modify the polynucleotide of interest for insertion into the chosen plasmid, it is suitable to use PCR. Appropriate primers for use in PCR preparation of the sequence can be designed to isolate the required coding region of the nucleic acid molecule, add restriction endonuclease or LIC sites, place the coding region in the desired reading frame.

In an embodiment, a polynucleotide for incorporation into an expression vector of the subject technology is prepared using PCR using appropriate oligonucleotide primers. The coding region is amplified, whilst the primers themselves become incorporated into the amplified sequence product. In an embodiment, the amplification primers contain restriction endonuclease recognition sites, which allow the amplified sequence product to be cloned into an appropriate vector.

The expression vectors can be introduced into plant or microbial host cells by conventional transformation or transfection techniques. Transformation of appropriate cells with an expression vector of the subject technology is accomplished by methods known in the art and typically depends on both the type of vector and cell. Suitable techniques include calcium phosphate or calcium chloride co-precipitation, DEAE-dextran mediated transfection, lipofection, chemoporation or electroporation.

Successfully transformed cells, that is, those cells containing the expression vector, can be identified by techniques well known in the art. For example, cells transfected with an expression vector of the subject technology can be cultured to produce polypeptides described herein. Cells can be examined for the presence of the expression vector DNA by techniques well known in the art.

The host cells can contain a single copy of the expression vector described previously, or alternatively, multiple copies of the expression vector, In some embodiments, the transformed cell is an animal cell, an insect cell, a plant cell, an algal cell, a fungal cell, or a yeast cell. In some embodiments, the cell is a plant cell selected from the group consisting of: canola plant cell, a rapeseed plant cell, a palm plant cell, a sunflower plant cell, a cotton plant cell, a corn plant cell, a peanut plant cell, a flax plant cell, a sesame plant cell, a soybean plant cell, and a *petunia* plant cell.

Microbial host cell expression systems and expression vectors containing regulatory sequences that direct high-level expression of foreign proteins are well known to those skilled in the art. Any of these could be used to construct vectors for expression of the recombinant polypeptide of the subjection technology in a microbial host cell. These vectors could then be introduced into appropriate microorganisms via transformation to allow for high level expression of the recombinant polypeptide of the subject technology.

Vectors or cassettes useful for the transformation of suitable microbial host cells are well known in the art. Typically, the vector or cassette contains sequences directing transcription and translation of the relevant polynucleotide, a selectable marker, and sequences allowing autonomous replication or chromosomal integration. Suitable vectors comprise a region 5' of the polynucleotide which harbors transcriptional initiation controls and a region 3' of the DNA fragment which controls transcriptional termination. It is preferred for both control regions to be derived from genes homologous to the transformed host cell, although it is to be understood that such control regions need not be derived from the genes native to the specific species chosen as a host.

Initiation control regions or promoters, which are useful to drive expression of the recombinant polypeptide in the desired microbial host cell are numerous and familiar to those skilled in the art. Virtually any promoter capable of driving these genes is suitable for the subject technology including but not limited to CYCI, HIS3, GALI, GALIO, ADHI, PGK, PH05. GAPDH, ADCI, TRPL, URA3, LEU2, ENO, TPI (useful for expression in *Saccharomyces*); AOXI (useful for expression in *Pichia*); and lac, trp, JPL, IPR, T7, tac, and trc (useful for expression in *Escherichia coli*).

Termination control regions may also be derived from various genes native to the microbial hosts. A termination site optionally may be included for the microbial hosts described herein.

In plant cells, the expression vectors of the subject technology can include a coding region operably linked to promoters capable of directing expression of the recombinant polypeptide of the subject technology in the desired tissues at the desired stage of development. For reasons of convenience, the polynucleotides to be expressed may comprise promoter sequences and translation leader sequences derived from the same polynucleotide. 3' non-coding sequences encoding transcription termination signals should also be present. The expression vectors may also comprise one or more introns to facilitate polynucleotide expression. For plant host cells, any combination of any promoter and any terminator capable of inducing expression of a coding region may be used in the vector sequences of the subject technology. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with an expression vector of the subject technology should be capable of promoting the expression of the vector. High level plant promoters that may be used in the subject technology include the promoter of the small subunit (ss) of the ribulose-1, 5-bisphosphate carboxylase for example from soybean (Berry-Lowe et al., J. MOLECULAR AND APP. GEN., 1:483 498 (1982), the entirety of which is hereby incorporated herein to the extent it is consistent herewith), and the promoter of the chlorophyll alb binding protein. These two promoters are known to be light-induced in plant cells (see, for example, GENETIC ENGINEERING OF PLANTS, AN AGRICULTURAL PERSPECTIVE, A. Cashmore, Plenum, N.Y. (1983), pages 29 38; Coruzzi, G. et al., The Journal of Biological CHEMISTRY, 258: 1399 (1983), and Dunsmuir, P. et al., JOURNAL OF MOLECULAR AND APPLIED GENETICS, 2:285 (1983), each of which is hereby incorporated herein by reference to the extent they are consistent herewith).

Precursor Synthesis to Reb J or Reb I

As previously stated steviol glycosides are the chemical compounds responsible for the sweet taste of the leaves of the South American plant *Stevia rebaudiana* (*Asteraceae*) and in the plant *Rubus chingii* (*Rosaceae*). These compounds are glycosylated diterpenes. Specifically, their molecules can be viewed as a steviol molecule, with its hydroxyl hydrogen atom replaced by a glucose molecule to form an ester, and a hydroxyl hydrogen with combinations of glucose and rhamnose to form an acetal.

One method of making the compounds of interest in the current disclosure is to take common or inexpensive precursors such as steviol, stevioside, Reb A or rubososide derived chemically or produced via biosynthesis in engineered microbes such as bacteria and/or yeast and to synthesize targeted steviol glycosides through known or inexpensive methods, such as Reb J or Reb I.

Aspects of the present disclosure relate to methods involving recombinantly expressing enzymes in a microbial system capable of producing steviol. In general, such enzymes may include: a copalyl diphosphate synthase (CPS), a kaurene synthase (KS) and a geranylgeranyl diphosphate to synthase (GGPPS) enzyme. This should occur in a microbial strain that expresses an endogenous isoprenoid synthesis pathway, such as the non-mevalonate (MEP) pathway or the mevalonic acid pathway (MVA). In some embodiments, the cell is a bacterial cell, including *E. coli*, or yeast cell such as a *Saccharomyces* cell, *Pichia* cell, or a *Yarrowia* cell. In some embodiments, the cell is an algal cell or a plant cell.

Thereafter, the precursor is recovered from the fermentation culture for use in chemical synthesis. Typically, this is steviol though it can be kaurene, or a steviol glycoside from the cell culture. In some embodiments, the steviol, kaurene and/or steviol glycosides is recovered from the gas phase while in other embodiments, an organic layer or polymeric resin is added to the cell culture, and the kaurene, steviol and/or steviol glycosides is recovered from the organic layer or polymeric resin. In some embodiments, the steviol glycoside is selected from rebaudioside A, rebaudioside B, rebaudioside C, rebaudioside N, rebaudioside E, rebaudioside F, rebaudioside J or dulcoside A. In some embodiments, the terpenoid produced is steviobioside or stevioside. It should also be appreciated that in some embodiments, at least one enzymatic step, such as one or more glycosylation steps, are performed ex vivo.

Part of the disclosure is the production of the Reb J steviol glycoside, which can be subject to further enzymatic conversion to Reb N. In some embodiments, Reb A can be converted to Reb J using a rhamnosyltransferase (RhaT) as described herein, e.g., EU11, EUCP1. HV1, UGT2E-B, or NX114, and a rhamnose donor moiety such as UDP-rhamnose. In some embodiments, the biosynthesis for the conversion of microbially produced steviol to a desired steviol glycoside (e.g., Reb N) occurs when the diterpenoid steviol is converted to rubososide and stevioside using multi-step chemical assembly of sugar moiety into the steviol backbone utilizing specifically identified and/or modified enzymes created by the inventors. In addition to the EU11,EUCP1, HV1 and UGT76G1 enzymes utilized herein other enzymes were identified that can work to deliver these steviol rebaudiosides as well. For example, it was determined that other UGT enzymes (CP1 and CP2 respectively—amino acid sequences at SEQ ID NO: 11 and SEQ ID NO: 13) and the UGT76G-AtSUS1 fusion enzyme can convert Reb J to Reb N.

Part of the disclosure is the production of the Reb I steviol glycoside from Reb A, which can be subject to further enzymatic conversion to Reb N. In some embodiments, the biosynthesis for the conversion of Reb A to Reb I occurs by reacting Reb A with a glucose donor moiety in the presence of a recombinant polypeptide having glucosyltransferase activity. In some embodiments, the glucose donor moiety is generated in situ. In some embodiments, the glucose donor moiety is added to the reaction. In some embodiments, the recombinant polypeptide having glucosyltransferase activity further comprises sucrose synthase activity. For example, in some embodiments, an enzyme identified as UGT76G1 (SEQ ID NO: 7) can convert Reb A to Reb I. In some embodiments, other UGT enzymes (e.g., CP1 and CP2 respectively—amino acid sequences at SEQ ID NO: 11 and SEQ ID NO: 13) can convert Reb A to Reb I. In some embodiments, the UCT76G-AtSUS1 fusion enzyme can convert Reb A to Reb I. In some embodiments, Reb I can be converted to Reb N using a rhamnosyltransferase (RhaT) as described herein, e.g., EU11, EUCP1, HV1, UGT2E-B, or NX114, and a rhamnose donor moiety such as UDP-rhamnose.

Biosynthesis of Steviol Glycosides

As described herein, the recombinant polypeptides of the present technology have UDP-glycosyltransferase (UDP-gluocosytransferase and/or UDP-rhamnosyltransferase) activities and are useful for developing biosynthetic methods for preparing steviol glycosides that are either not present in nature or typically of low abundance in natural sources, such as rebaudioside J, rebaudioside I and rebaudioside N, respectively. The recombinant polypeptides of the present technology have UDP-glycosyltransferase activities, are useful for developing biosynthetic methods for preparing steviol glycosides, such as rebaudioside J or rebaudioside I, and reaching the synthetic production of rebaudioside N.

The substrate or starting steviol glycoside composition, can be any natural or synthetic compound capable of being converted into a steviol glycoside compound in a reaction catalyzed by one or more UDP-rhamnosyltransferases. For example, the substrate can be natural *stevia* extract, steviol, steviol-13-O-glucoside, steviol-19-O-glucoside, steviol-1, 2-bioside, rubusoside, stevioside, rebaudioside A, rebaudioside B or rebaudioside I. The substrate can be a pure compound or a mixture of different compounds. Preferably, the substrate includes a compound selected from the group consisting of rubusoside, stevioside, steviol, rebaudioside A, rebaudioside B, rebaudioside J and combinations thereof.

The method described herein also provides a coupling reaction system in which the recombinant peptides described herein can function in combination with one or more additional enzymes to improve the efficiency or modify the outcome of the overall biosynthesis of steviol glycoside compounds. For example, the additional enzymes may regenerate the UDP-rhamnose needed for the rhamnosylation reaction (see e.g., Pei et al., "Construction of a novel UDP-rhamnose regeneration system by a two-enzyme reaction system and application in glycosylation of flavonoid," *Biochemical Engineering Journal*, 139: 33-42 (2018), the entire disclosure of which is incorporated herein by reference) and the additional enzyme may regenerate the UDP-glucose needed for the glycosylation reaction by converting the UDP produced from the glycosylation reaction back to UDP-glucose (using, for example, sucrose as a donor of the glucose residue), thus improving the efficiency of the glycosylation reaction.

In another embodiment, the method of the subject technology further includes incubating a recombinant and novel UDP-rhamnosyltransferase (RhaT) according to the current disclosure with the substrate and one or more additional recombinant polypeptides (e.g., a recombinant UGT) described herein. The recombinant UGT can catalyze a different glycosylation reaction than the one catalyzed by the recombinant polypeptide of the subject technology leading to the production of Reb J and Reb N.

Suitable UDP-glycosyltransferase includes any UGT known in the art as capable of catalyzing one or more reactions in the biosynthesis of steviol glycoside compounds, such as UGT85C2, UGT74G1, UGT76G1, or the functional homologs thereof.

In some embodiments, in the in vitro method of the subject technology, UDP-glucose and/or UDP-L-rhamnose can be included in the buffer at a concentration of from about 0.2 mM to about 5 mM, preferably from about 0.5 mM to about 2 mM, more preferably from about 0.7 mM to about 1.5 mM. In an embodiment, when a recombinant sucrose synthase is included in the reaction, sucrose is also included in the buffer at a concentration of from about 100 mM to about 500 mM, preferably from about 200 mM to about 400 mM, more preferably from about 250 mM to about 350 mM.

In some embodiments, in the in vitro method of the subject technology, the weight ratio of the recombinant polypeptide to the substrate, on a dry weight basis, is from about 1:100 to about 1:5, preferably from about 1:50 to about 1:10, more preferably from about 1:25 to about 1:15.

In some embodiments, the reaction temperature of the in vitro method is from about 20° C. to about 40° C., suitably from 25° C. to about 37° C.

One skilled in the art will recognize that the steviol glycoside composition produced by the method described herein can be further purified and mixed with other steviol glycosides, flavors, or sweeteners to obtain a desired flavor or sweetener composition. For example, a composition enriched with Reb J or Reb N produced as described herein can be mixed with a natural *stevia* extract containing rebaudioside A as the predominant steviol glycoside, or with other synthetic or natural steviol glycoside products to make a desired sweetener composition. Alternatively, a substantially purified steviol glycoside (e.g., rebaudioside J and rebaudioside N) obtained from the methods described herein can be combined with other sweeteners, such as sucrose, maltodextrin, aspartame, sucralose, neotame, acesulfame potassium, and saccharin. The amount of steviol glycoside relative to other sweeteners can be adjusted to obtain a desired taste, as known in the art. The steviol glycoside described herein (including rebaudioside N, rebaudioside I, rebaudioside J, or a combination thereof) can be included in food products (such as beverages, soft drinks, ice cream, dairy products, confectioneries, cereals, chewing gum, baked goods, etc.), dietary supplements, medical nutrition, as well as pharmaceutical products.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this disclosure "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the disclosure is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the 1,2 RhaT and UGT enzymes of the current disclosure are capable of directing the production of a variety of steviol glycosides and have a substantial percent sequence identity to the polynucleotide sequences provided herein and are encompassed within the scope of this disclosure.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

EXAMPLES

Example 1: Enzymatic Activity Screening of 1,2 RhaT Enzymes

Phylogenetic, gene cluster, and protein BLAST analyses were used to identify candidate 1,2 RhaT transferase genes. Full-length DNA fragments of candidate 1,2 RhaT transferase genes were optimized and synthesized according to the codon preference of *E. coli* (Genscript, NJ). The synthesized DNA fragments were cloned into a bacterial expression vector pETite N-His SUMO Kan Vector (Lucigen).

Each expression construct was transformed into *E. coli* BL21 (DE3), which was subsequently grown in LB media containing 50 µg/mL kanamycin at 37° C. until reaching an $OD_{600}$ of 0.8-1.0. Protein expression was induced by adding 1 mM of isopropyl β-D-1-thiogalactopyranoside (IPTG), and the culture was incubated further at 16° C. for 22 hours. Cells were harvested by centrifugation (3,000×g; 10 min; 4° C.). The cell pellets were collected and were either used immediately or stored at −80° C.

The cell pellets typically were re-suspended in lysis buffer (50 mM potassium phosphate buffer, pH 7.2, 25 µg/ml lysozyme, 5 µg/ml DNase I, 20 mM imidazole, 500 mM NaCl, 10% glycerol, and 0.4% Triton X-100). The cells were disrupted by sonication at 4° C., and the cell debris was clarified by centrifugation (18,000×g; 30 min). The supernatant was loaded to an equilibrated (equilibration buffer: 50 mM potassium phosphate buffer, pH 7.2, 20 mM imidazole, 500 mM NaCl, 10% glycerol) Ni-NTA (Qiagen) affinity column. After loading of the protein samples, the column was washed with equilibration buffer to remove unbound contaminant proteins. The His-tagged 1,2 RhaT recombinant polypeptides were eluted with an equilibration buffer containing 250 mM of imidazole.

The purified candidate 1,2 RhaT recombinant polypeptides were assayed for UDP-rhamnosyltransferase activity. Typically, the recombinant polypeptide (20-50 µg) was tested in a 200 µl in vitro reaction system. The reaction system contains 50 mM of potassium phosphate buffer, pH 7.2, 3 mM of $MgCl_2$, 0.25-1 mg/ml of rebaudioside A and UDP-L-rhamnose. The reaction was performed at 30-37° C. and terminated by adding 1-butanol.

The product samples were extracted three times with 200 µL of 1-butanol. The pooled fraction was dried and dissolved in 100 µL of 80% methanol for high-performance liquid chromatography (HPLC) analysis.

HPLC analysis was performed using a Dionex UPLC ultimate 3000 system (Sunnyvale, Calif.), including a quaternary pump, a temperature controlled column compartment, an auto sampler and a UV absorbance detector. A Synergi Hydro-RP column (Phenomenex) with guard column was used for the characterization of steviol glycosides in the pooled samples. The detection wavelength used in the HPLC analysis was 210 nm.

After activity screening, several 1,2 RhaT enzymes having UDP-rhamnosyltransferase activity were identified for bioconversion of Reb A to Reb J.

Example 2: Enzymatic Bioconversion of Reb A to Reb J

The biosynthesis of rebaudioside J involves glucosylation and rhamnosylation of the aglycone steviol. Specifically, Reb J can be produced by rhamnosylation of the C-2 of the 19-O-glucose of Reb A, i.e., via a 1,2 rhamnosylation (FIG. 3).

Figure 4:
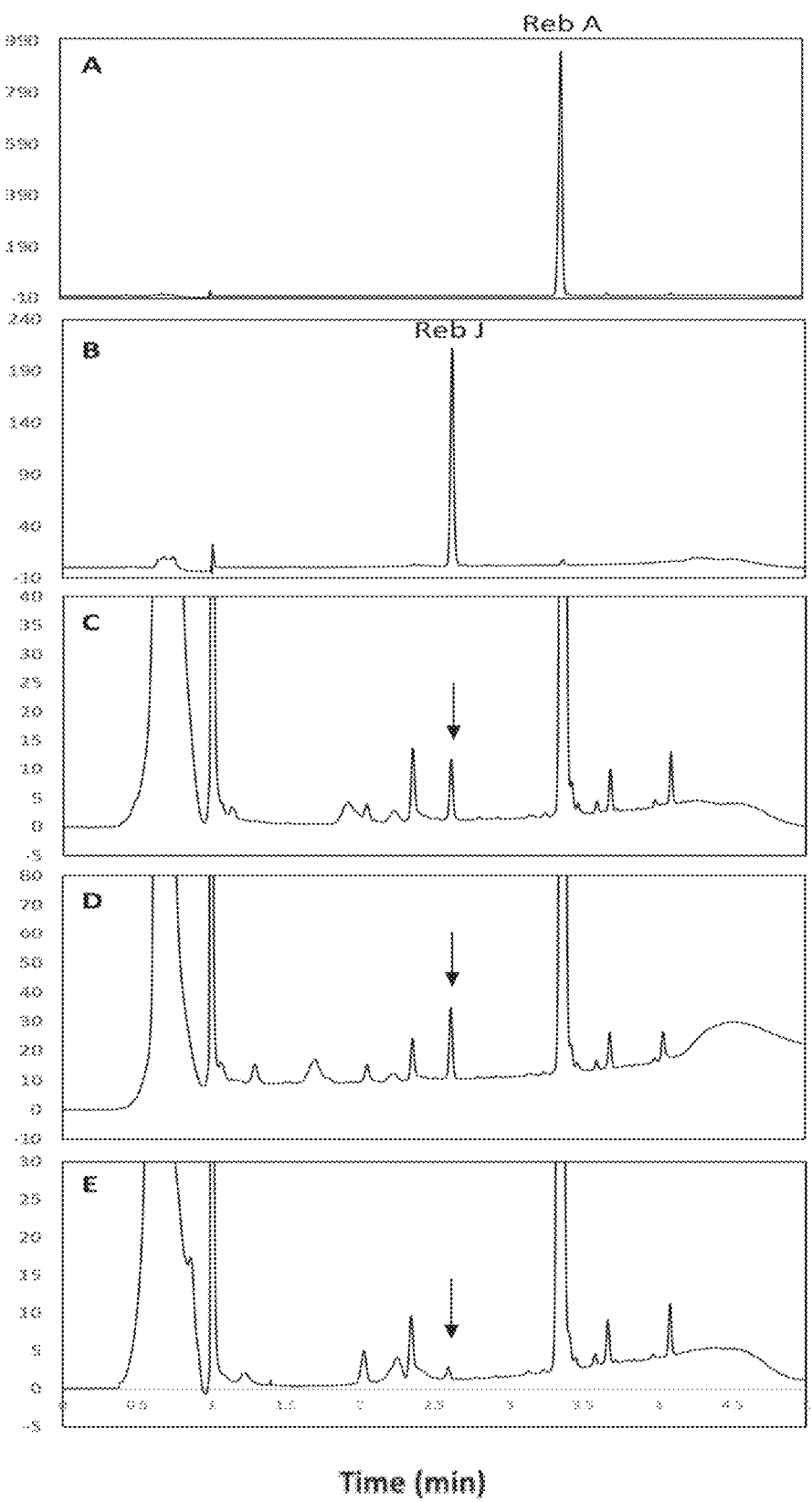
FIG. 4 shows the in vitro production of Reb J from Reb A as catalyzed by selected 1,2 RhaT enzymes via HPLC analysis. Panel A shows the retention time of a Reb A standard. Panel B shows the retention time of a Reb J standard. Panel C shows the retention times of the products obtained from a reaction system catalyzed by EU11 (SEQ ID NO: 1) using Reb A as the substrate. Panel D shows the retention times of the products obtained from a reaction system catalyzed by EUCP1 (SEQ ID NO: 3) using Reb A as the substrate. Panel E shows the retention times of the products obtained from a reaction system catalyzed by HV1 (SEQ ID NO: 5) using Reb A as the substrate. Arrows indicate the presence of Reb J.
Figure 5:
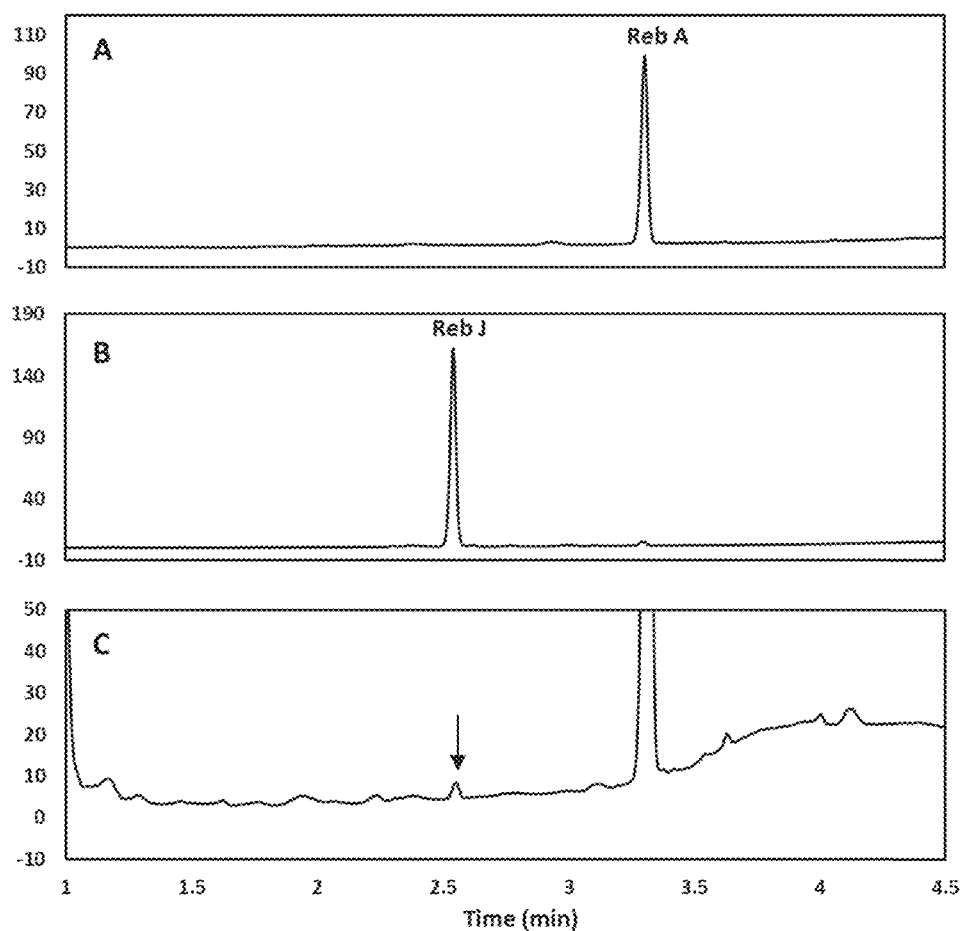
FIG. 5 shows the in vitro production of Reb J from Reb A as catalyzed by UGT2E-B via HPLC analysis. Panel A shows the retention time of a Reb A standard. Panel B shows the retention time of a Reb J standard. Panel C shows the retention times of the products obtained from a reaction system catalyzed by UGT2E-B (SEQ ID NO: 9) using Reb A as the substrate. The arrow indicates the presence of Reb J.
Figure 6:
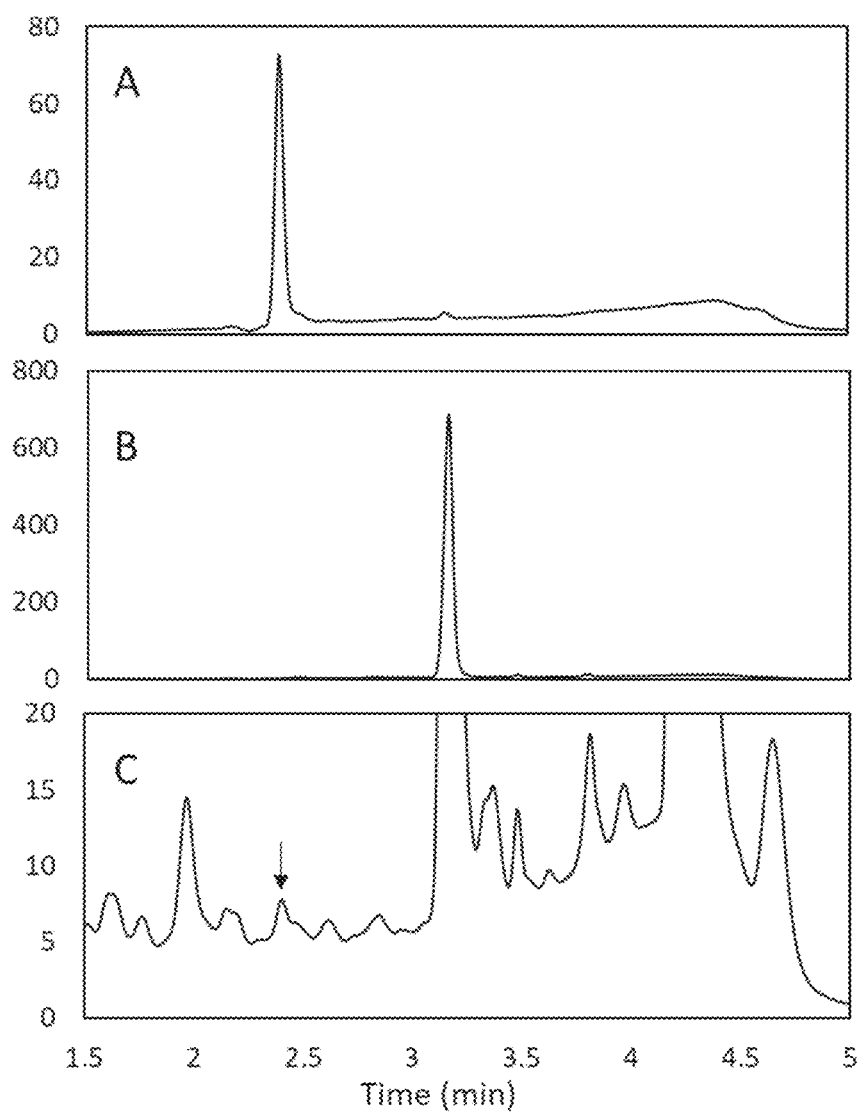
FIG. 6 shows the in vitro production of Reb J from Reb A as catalyzed by NX114 via HPLC analysis. Panel A shows the retention time of a Reb J standard. Panel B shows the retention time of a Reb A standard. Panel C shows the retention times of the products obtained from a reaction system catalyzed by NX114 (SEQ ID NO: 19) using Reb A as the substrate. The arrow indicates the presence of Reb J.

FIGS. 4-6 compare the retention times of Reb A and Reb J standards as analyzed by HPLC against the retention times of the reaction products obtained from the rhamnosylation reaction catalyzed by the candidate 1,2 RhaT enzymes.

It has been reported that EU11, EUCP1 and HV1 have glucosylation activity and are capable of transferring a glucose moiety from UDP-glucose to steviol glycosides, producing compounds such as stevioside, rebaudioside KA, rebaudioside E, rebaudioside D, rebaudioside V, and rebaudioside D3 etc.

As shown in FIGS. 4(C)-4(E), Reb A was converted into Reb J in reaction systems catalyzed by EU11 (SEQ ID NO: 1), a circular permutation of EU11 designated herein as EUCP1 (SEQ ID NO: 3), and HV1 (SEQ ID NO: 5), respectively, demonstrating that in addition to glucosylation activity, these enzymes also have 1,2 rhamnosyltranferase activity. EUCP1 was found to have higher 1,2 rhamnosyltranferase activity than EU11, while EU11 showed much higher 1,2 rhamnosyltranferase activity than HV1.

FIG. 5 shows that Reb A was converted into Reb J in a reaction system catalyzed by UGT2E-B (SEQ ID NO: 9). FIG. 6 shows that Reb A was converted into Reb J in a reaction system catalyzed by NX114 (SEQ ID NO: 19).

Collectively, these data demonstrate that each of the enzymes EU11, EUCP1, HV1, UGT2E-B, and NX114 exhibits 1,2 RhaT activity and is capable of transferring a rhamnose moiety from a UDP-L-rhamnose donor to the C-2' of the 19-O-glucose moiety of Reb A in an a 1,2 rhamnosylation reaction, thereby producing Reb J.

Example 3: Confirmation of Reb J Production by LC-MS Analysis

To confirm the identity of the compounds produced in the reactions catalyzed by the 1,2 RhaT candidate enzymes, LC-MS analyses were performed using a Synergy Hydro-RP column. Mobile phase A was 0.1% formic acid in water, and mobile phase B was 0.1% formic acid in acetonitrile. The flow rate was 0.6 ml/min. Mass spectrometry analysis of the samples was done on the Q Exactive Hybrid Quadrupole-Orbitrap Mass Spectrometer (Thermo Fisher Scientific) with an optimized method in positive ion mode.

LC-MS analysis confirmed that the products obtained from the rhamsylation reaction catalyzed by EU11, EUCP1, HV1, UGT2E-B, and NX114, respectively, have the same mass [(M+Na$^+$) 1135.48 m/z] and retention time (2.61 min) as the Reb J standard.

Example 4: Enzymatic Bioconversion of Reb J to Reb N

Referring again to FIG. 3, Reb N can be produced by glucosylation of the C-3' of the 19-O-glucose of Reb J in a s 1,3 glucosylation reaction.

To identify suitable UGTs for bioconversion of Reb J to Reb N, enzyme candidates were assayed using the Reb J products obtained from Example 1.

After terminating Reb J production by heating (to denature the 1,2 RhaT enzymes), UGT candidate enzymes (5 μg of enzymes per 200 μl of reaction mixture) and 1 mM of UDP-glucose was added into the reaction mixture. The glucosylation reaction was performed at 37° C. for 3 hours.

Figure 7:
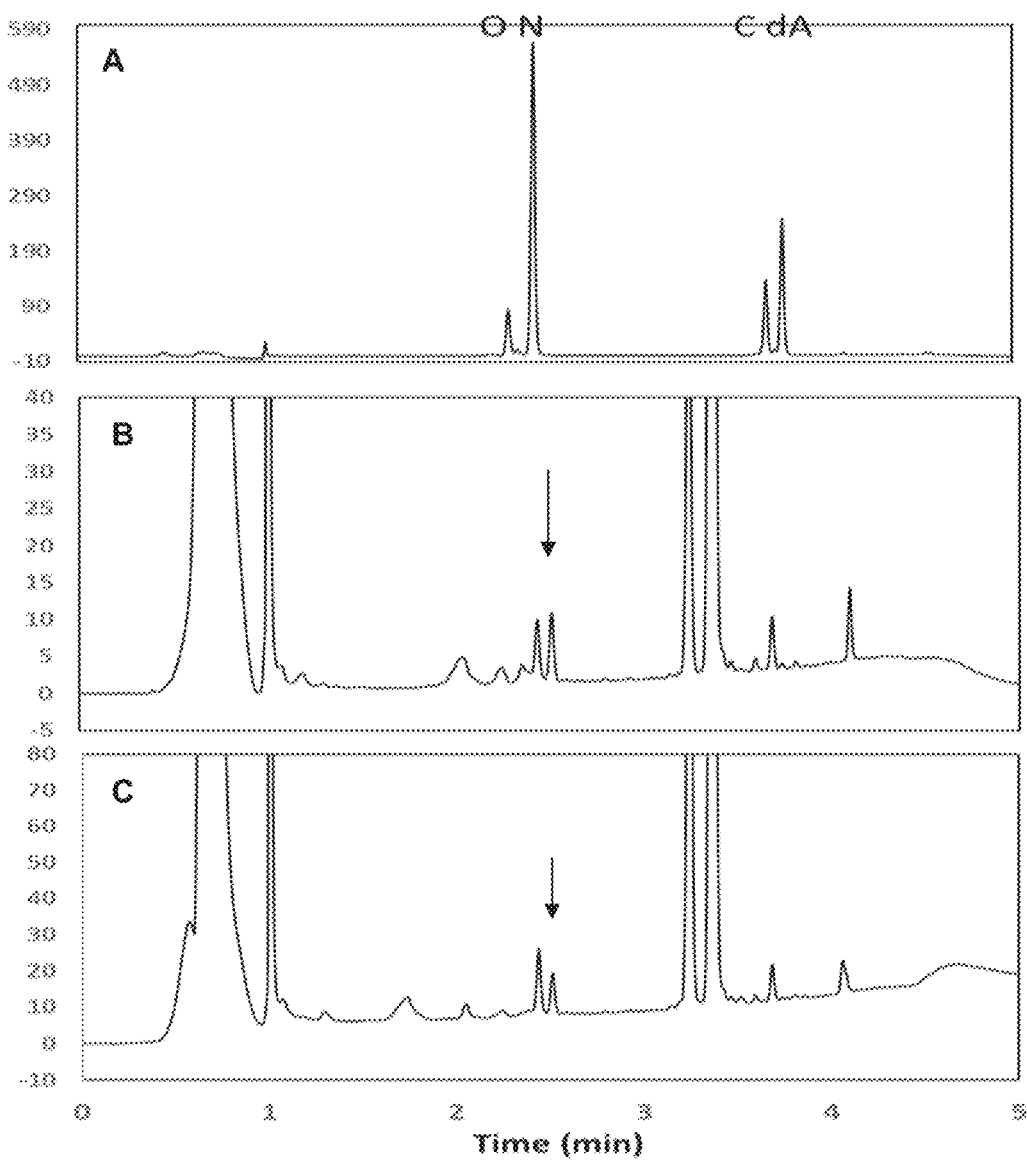
FIG. 7 shows the in vitro production of Reb N from Reb J as catalyzed by UGT76G1 via HPLC analysis. Panel A shows the retention time of various steviol glycoside standards include rebaudioside O, Reb N, rebaudioside C, and dulcoside A. Panel B shows the retention time of the products obtained from a reaction system catalyzed by UGT76G1 (SEQ ID NO: 7) using Reb J obtained from a EUI1-catalyzed reaction. Panel C shows the retention time of the products obtained from a reaction system catalyzed by UGT76G1 (SEQ ID NO: 7) using Reb J obtained from a EUCP1-catalyzed reaction. Arrows indicate the presence of Reb N.

FIG. 7 compares the retention times of Reb O, Reb N, Reb C, and dulcoside A ("dA") standards as analyzed by HPLC against the retention times of the reaction products obtained from the glucosylation reaction catalyzed by UGT76G1 (SEQ ID NO: 7) using the Reb J products obtained from the EU1-catalyzed (FIG. 7(B)) and EUCP1-catalzyed (FIG. 7(C)) reaction systems of Example 1, respectively, as the substrate. As shown in FIGS. 7(B) and 7(C), Reb J was converted to Reb N in the presence of UGT76G1.

Based on the structure of UGT76G1, the inventors were able to design CP1 (SEQ ID NO: 11) which is a circular permutation of UGT76G1, CP2 (SEQ ID NO: 13) which is a mutant of CP1 and was generated by inserting a linker between the C-terminal and N-terminal of CP1, and a fusion enzyme GS (SEQ ID NO: 15) that includes a UDP-glycosyltransferase (UGT) domain, UGT76G1, coupled to a sucrose synthase (SUS) domain, AtSUS1.

Figure 8:
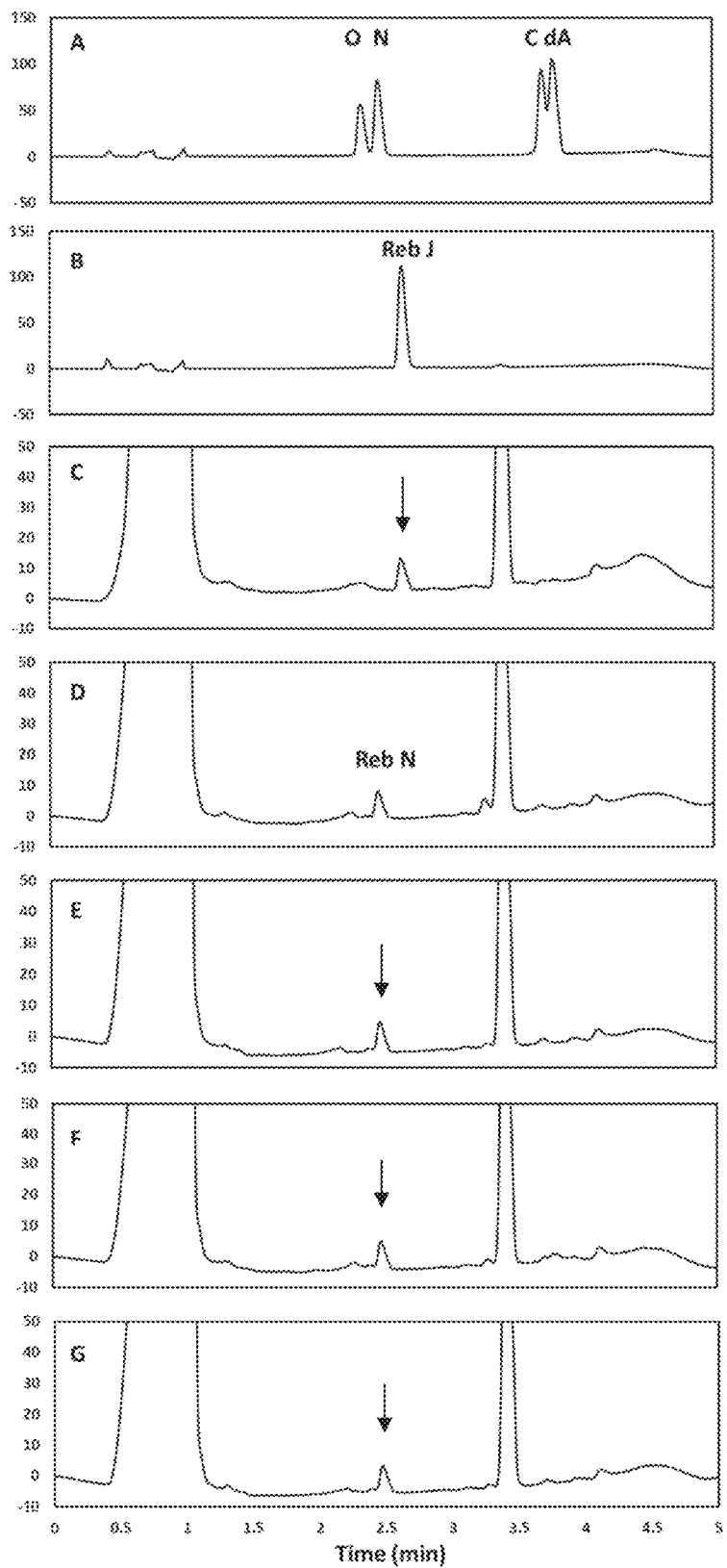
FIG. 8 shows the in vitro production of Reb N from Reb J as catalyzed by selected UGT enzymes via HPLC analysis. Panel A shows the retention time of various steviol glycoside standards include rebaudioside O, Reb N, rebaudioside C, and dulcoside A. Panel B shows the retention time of a Reb J standard. Panel B shows the retention time of the Reb J intermediate obtained from a EUCP1-catalyzed reaction (as indicated by the arrow). Panel D shows the retention time of the Reb N product obtained from a reaction system catalyzed by UGT76G1 (SEQ ID NO: 7) using the Reb J intermediate shown in Panel B. Panel E shows the retention time of the Reb N product obtained from a reaction system catalyzed by CP1 (SEQ ID NO: 11) using the Reb J intermediate shown in Panel B (as indicated by the arrow). Panel F shows the retention time of the Reb N product obtained from a reaction system catalyzed by CP2 (SEQ ID NO: 13) using the Reb J intermediate shown in Panel B (as indicated by the arrow). Panel G shows the retention time of the Reb N product obtained from a reaction system cata-lyzed by fusion enzyme GS (SEQ ID NO: 15) using the Reb J intermediate shown in Panel B (as indicated by the arrow).

Referring to FIG. 8, FIG. 8(A) shows the retention time of the Reb J standard. FIG. 8(B) confirms the bioconversion of Reb A into Reb J as catalyzed by EUCP1. Using the Reb J product obtained from the EUCP1-catalyzed reaction as the substrate, UGT76G1, CP1, CP2, and GS were assayed for their glucosylation activity to convert Reb J into Reb N. Comparing against FIG. 8(C) which shows the retention time of the Reb N standard, FIGS. 8(D), 8(E), 8(F), and 8G demonstrate that each of the UGT76G1, CP1, CP2, and GS enzymes is capable of transferring a glucose moiety from UDP-glucose to the C-3' of the 19-O-glucose of Reb J in a p 1,3 glucosylation reaction, thereby producing Reb N.

To evaluate further the activity of a UGT-SUS fusion enzyme in the bioconversion of Reb J to Reb N, assays were performed in the presence of UDP and sucrose but without UDP-glucose using the following enzymatic systems: (1) UGT76G1 (SEQ ID NO: 7) by itself, (2) addition of both a UDP-glycosyltransferase UGT76G1 (SEQ ID NO: 7) and a sucrose synthase AtSUS1 (SEQ ID NO: 17), and (3) fusion enzyme GS (SEQ ID NO: 15) including UDP-glycosyltransferase (UGT) domain, UGT76G1, coupled to a sucrose synthase (SUS) domain, AtSUS1, which has both UDP-glycosyltransferase activity and sucrose synthase activity.

Figure 9:
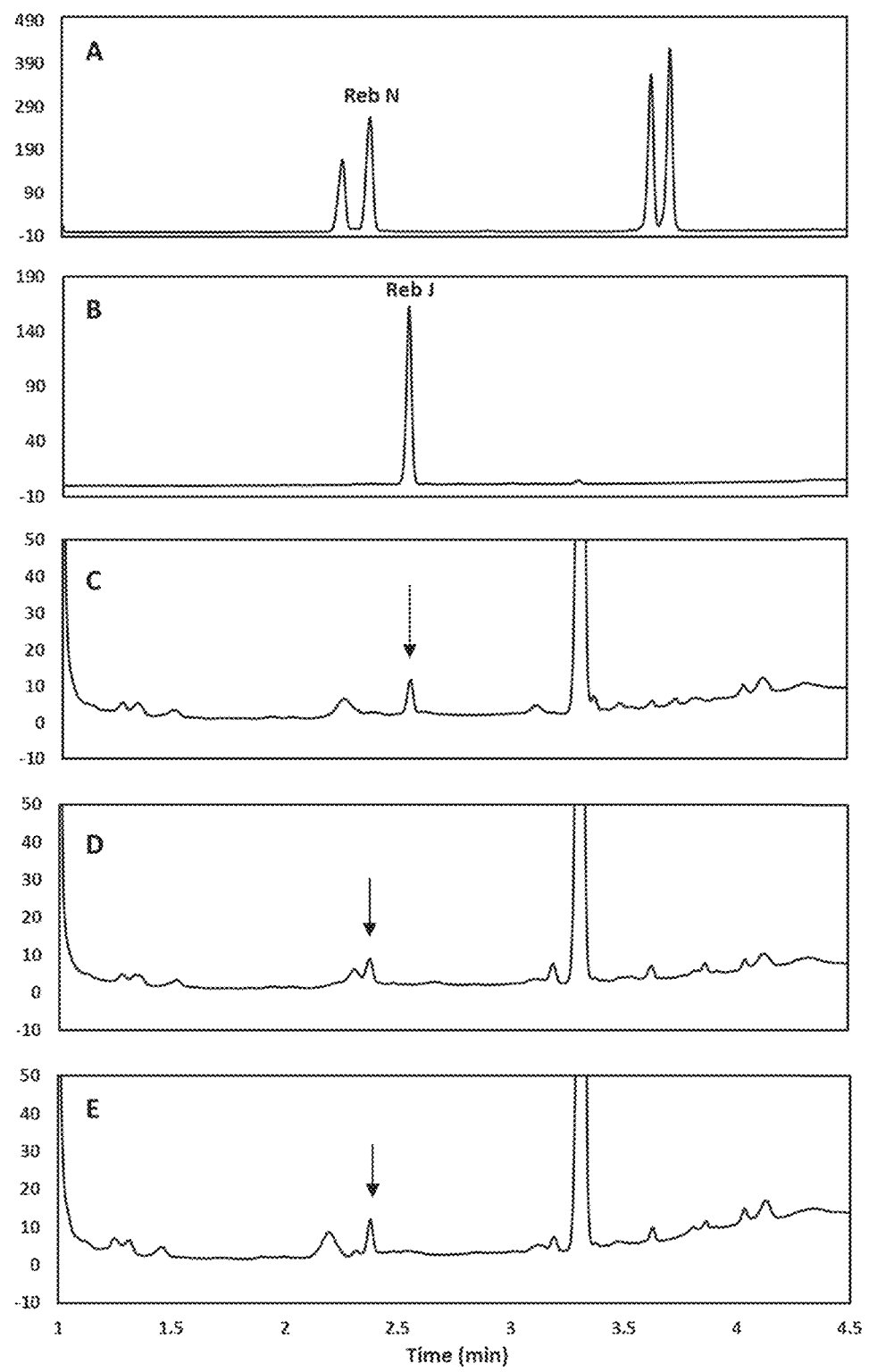
FIG. 9 shows the in vitro production of Reb N from Reb J in the presence of UDP and sucrose as catalyzed by selected UGT enzymes via HPLC analysis. Panel A shows the retention time of a Reb N standard. Panel B shows the retention time of a Reb J standard. Panel C shows the retention time of the product obtained from a UGT76G-catalyzed reaction. No Reb N production is observed. The arrow indicates the presence of Reb J. Panel D shows the retention time of the product obtained from a reaction system catalyzed by both UGT76G1 and AtSUS1 (SEQ ID NO: 17). Arrow indicates the presence of Reb N. Panel E shows the retention time of the product obtained from a reaction system catalyzed by fusion enzyme GS (SEQ ID NO: 15). Arrow indicates the presence of Reb N.

As shown in FIG. 9(C), UGT76G1 is unable to convert Reb J to Reb N when only UDP and sucrose are present in the reaction system. On the other hand, by using a catalytic system including both a UGT enzyme (e.g., UGT76G1) and an SUS enzyme (e.g., AtSUS1), the SUS enzyme was able to generate UDP-glucose from UDP and sucrose, and the UGT enzyme was able to transfer the glucose moiety from UDP-glucose to Reb J, thereby producing Reb N (FIG. 9(D)). Similarly, the fusion enzyme GS was able to produce Reb N from Reb J (FIG. 9(E)), indicating that the fusion enzyme has sucrose synthase activity and was able to generate UDP-glucose from UDP and sucrose. Additionally, the fusion enzyme GS was found to have higher enzymatic activity (more Reb N was produced) compared to the reaction system where UGT76G1 and AtSUS1 are present as individual enzymes.

Example 5: Confirmation of Reb N Production by LC-MS Analysis

To confirm further the identity of the compounds produced in the reactions catalyzed by the UGT enzymes, LC-MS analyses were performed using a Synergy Hydro-RP column. Mobile phase A was 0.1% formic acid in water, and mobile phase B was 0.1% formic acid in acetonitrile. The flow rate was 0.6 ml/min. Mass spectrometry analysis of the samples was done on the Q Exactive Hybrid Quadrupole-Orbitrap Mass Spectrometer (Thermo Fisher Scientific) with an optimized method in positive ion mode.

LC-MS analysis confirmed that the products obtained from the glucosylation reaction catalyzed by UGT76G1, CP1, CP2, and GS, respectively, using Reb J (produced from the rhamnosylation reaction catalyzed by EU11/EUCP1/HV/UGT2E-B/NX114 as described in Example 1) as the substrate, have the same mass [(M+Na$^+$) 1297.53 m/z] and retention time (2.43 min) as the Reb N standard.

Sequences of Interest:

Sequences:
EU11: Amino Acid Sequence
(SEQ ID NO: 1)
MDSGYSSSYAAAAGMHVVICPWLAFGHLLPCLDLAQRLASRGHRVSFVST
PRNISRLPPVRPALAPLVAFVALPLPRVEGLIPDGAESTNDVPHDRPDMV
ELFIRRAFDGLAAPFSEFLGTACADWVIVDVFHHWAAAAALEHKVPCAMM
LLGSAHMIASIADRRLERAETESPAAAGQGRPAAAPTFEVARMKLIRTKG
SSGMSLAERFSLTLSRSSINVGRSCVEFEYETVPLLSTLRGKPLEFLGLN
IPPLHEGRREDGEDATVRWLDAQPAKSVVYNALGSEVPLGVEKVHELALG
LELAGTRFLWALRICPTGVSDADLITAGFEERTRGRGVVATRWVPQMSIL
AHAAVGAFLTIICGWINSTIEGLMFGHPLEMPITGDQGPNARLIEAKNAG
LQVARNDGDGSFDREGVAAAIRAVAVEEESSKAIMAKAKKLQEIVADMAC
ITERYIDGFIQQLRSYKD EU11: DNA Sequence
(SEQ ID NO: 2)
ATGGATTCGGGTTACTCTTCCTCCTATGCGGCGGCTGCGGGTATGCACGT
TGTTATCTGTCCGTGGCTGGCTTTTGGTCACCTGCTGCCGTGCCTGGATC
TGGCACAGCGTCTGGCTTCACGCGGCCATCGTGTCAGCTTCGTGTCTACC
CCGCGCAATATTTCGCGTCTGCCGCCGGTTCGTCCGGCACTGGCTCCGCT
GGTTGCATTTGTCGCTCTGCCGCTGCCGCGCGTGGAAGGTCTGCCGGATG
GTGCGGAAAGTACCAACGACCTTGCCGCATGATCGCCCGGACATGGTTGA
ACTGCACCGTCGTGCATTCGATGGTCTGGCAGCACCGTTTTCCGAATTTC
TGGGTACGGCGTGCGCCGATTGGGTGATCCTTTGACGTCTTTCATCACTG
GCGGCGGCGGCGGCGCTGGAACATAAAGTTCCGTGTGCAATGATGCTGC
TGGGCTCAGCTCACATGATTGCGTCGATCGCAGACCGTCGCCTGGNACGT
GCAGAAACCGAAAGTCCGGCTGCGGCCGGCCAGGGTCGCCCGGCAGCTGC
GCCGACCTTCGAAGTGGCCCGCATGAAACTGATTCGTACGAAAGGCAGCT
CTGGTATGAGCCTGGCAGAACGCTTCTAGTCTGACCCTCTTCCCGTAGTT
CCCTGGTGGTTGGTCGCAGTTGCGTTGAATTTGAACCGGAAACCGTCCCG
CTGCTGTCCACGCTGCGTGGTAAACCGATCAccuTcTGGGTCTGATGCCG
CCGCTGCATGAAGGCCGTCGCGAAGATGGTGAAGACGCAACGGTGCGTTG
GCTGGATGCACAGCCGGCTAAAAGCGTCGTGTATGTCGCCCTGGGCTCTG
AAGTGCCGCTGGGTGTGGAAAAAGTTCACGAACTGGCACTGGGCCTGGAA
CTGGCTGGCACCCGCTTCCTGTGGGCACTGCGTAAACCGACGGGTGTGAG
CGATGCGGACCTGCTGCCGGCCGGTTTTGAAGAACGTACCCGCGGCCGTG
GTGTTGTCGCAACGCGTTGGGTCCCGCAAATGAGCATTCTGGCGCATGCC
GCAGTGGGCGCCTTTCTGACCCACTGTGGTTGGAACAGCACGATCGAAGG
CCTGATGTTTGGTCACCCGCTGATTATGCTGCCGATCTTCGGCGATCAGG
GTCCGAACGCACGTCTGATTGAAGCGAAAAATGCCGGCCTGCAACTTTGC
GCGCAACGATGGCGACGGTTCTTTCGACCGTGAGGGTGTGGCTGCGGCCA
TTCGCGCAGTGGCTGTTGAAGAAGAATCATCGAAAGTTTTTCAGGCGAAA
GCCAAAAAACTGCAAGAAATCGTCGCGGATATGGCCTGCCACGAACGCTA
CATTGATGGTTTCATTCAGCAACTGCGCTCCTACAAAGACTAA EUCP1: Amino Acid sequence
(SEQ ID NO: 3)
MGSSGMSLAERFSLTLSRSSLVVGRSCVEFEYETVPLLSILRGKPITFLG
LMPPLHEGRREDGEDATVRWLDAQPAKSVVYVALGSEVLGVEKVHELALG
LELAGTRFLWALRKPTGVSDADLLPAGFEERTRGRGVVATRWVPQMSILA
HAAVGAFLTHCGWNSTIEGLMFGHPLIIMLPIFGDQGPNARLIEAKNAGL
QVARNDGDGSFDREGVAAAIRAVAVEEESSKVFQAKAKKLANIVADMACH
ERYIDGFIQQLRSYKDDSGYSSSYAAAAGMHVVICPWLAFGHLLPCLDLA
QRLASRGHRVSFVSTPRNISRLPPVRPALAPINAFVALPLPRVEGLPDGA
ESTNDVPHDRPDMVELHRRAFDGLAAPFSEFLGTACADWVIVDVFHHWAA
AAALEHKVPCAMMLLGSAHMIASIADRRLERAETESPAAAGQGRPAAAPT
FEVARMKLIRTK EUCP1: DNA Sequence
(SEQ ID NO: 4)
ATGGGTAGCTCGGGCATGTCCCTGGCGGAACGCTTTTCGCTGACGCTGAG
TCGCTCATCCCTGGTTGTTGGTCGCAGTTGTGTTGAATTTGAACCGGAAA
CCGTTCCGCTGCTGTCTACGCTGCGCGGCAAACCGATTACCTTCCTGGGT
CTGATGCCGCCGCTGCATGAAGGCCGTCGCGAAGATGGTGAAGACGCCAC
GGTGCGTTGGCTGGATGCTCAGCCGGCGAAATCGGTGGTTTATGTCGCAC
TGGGCAGCGAAGTGCCGCTGGGTGTCGAAAAAGTGCACGAACTGGCCCTG
GGCCTGGAACTGGCAGGCACCCGCTTTCTGTGGGCACTGCGTAAACCGAC
GGGCGTTAGCGATGCTGACCTGCTGCCGGCGGGTTTCGAAGAACGCACCC
GCGGCCGTGGTGTCGTGGCCACCCGTTGGGTGCCGCAAATGTCCATTCTG
GCTCATGCGGCCGTTGGCGCATTTCTGACCCACTGCGGTTGGAACAGCAC
GATCGAAGGCCTGATGTTTGGTCATCCGCTGATTATGCTGCCGATCTTCG
GCGATCAGGGTCCGAACGCACGCCTGATCGAAGCCAAAAATGCAGGCCTG
CAAGTTGCGCGTAACGATGGCGACGGTAGCTTTGACCGCGAAGGTGTCGC
AGCTGCGATTCGTGCTGTGGCGGTTGAAGAAGAAGCAGCAAAGTCTTCC
AGGCCAAAGCGAAAAAACTGCAAGAAATCGTGGCTGATATGGCGTGTCAT
GAACGCTATATTGACGGCTTTATCCAGCAACTGCGTTCTTACAAAGATGA
CAGTGGCTATAGTTCCTCATACGCCGCAGCTGCGGGTATGCATGTTGTCA
TTTGCCCGTGGCTGGCGTTTGGTCACCTGCTGCCGTGTCTGGATCTGGCA
CAGCGCCTGGCATCTCGCGGTCACCGTGTTTCGTTCGTCAGCACCCCGCG
CAATATCAGTCGTCTGCCGCCGGTTCGTCCGGCGCTGGCGCCGCTGGTTG
CGTTCGTTGCACTGCCGCTGCCGCGTGTGGAAGGTCTGCCGGATGGTGCC
GAATCGACCAACGACGTTCCGCATGATCGTCCGGACATGGTCGAACTGCA
TCGTCGCGCCTTTGATGGCCTGGCCGCACCGTTTAGCGAATTTCTGGGTA
CGGCCTGCGCAGATTGGGTCATTGTGGACGTTTTTCACCACTGGGCGGCG
GCGGCGGCGCTGGAACATAAAGTGCCGTGTGCGATGATGCTGCTGGGTTC
CGCCCACATGATTGCTTCAATCGCGGATCGTCGCCTGGAACGTGCCGAAA HV1: Amino Acid sequence (SEQ ID NO: 5)
MDGNSSSSPLHVVICPWLALGHLLPCLDIAERLASRGHRVSFVSTPRNIA

RLPPLRYAVAPLVDFVALPLPHVDGLPEGAESTNDVPYDKFELHRKAFDG

LAAPFSEFLRAACAEGAGSRPDWLIVDTFHHWAAAAAVENKVPCVMLLLG

AATVIAGFARGVSEHAAAAVGKERPAAEAPSFETERRKLMTTQNASGMTV

AFRYFLTLMRSDLVAIRSCAEWEPESVAALTTLAGKPVVPLGLLPPSPEG

GRGVSKEDAAVRWLDAQPAKSVVYVALGSEVPLRAEQVHELATGLELSGA

RFLWALRKPTDAPDAAVLPPGFEERTRGRGLVVTGWVPQIGVLAHGAVAA

FLTHCGWNSTIEGLLFGHPLIMLPISSDQGPNARIMEGRKVGMQVPRDES

DGSFRREDVAATVRAVAVEEDGRRVFTANAKKMQEIVADGACHERCIDGF

IQQLRSYKA

HV1: DNA Sequence (SEQ ID NO: 6)
ATGGATGGTAACTCCTCCTCCTCGCCGCTGCATGTGGTCATTTGTCCGTG

GCTGGCTCTGGGTCACCTGCTGCCGTGTCTGGATATTGCTGAACGTCTGG

CGTCACGCGGCCATCGTGTCAGTTTTGTGTCCACCCCGCGCAACATTGCC

CGTCTGCCGCCGCTGCGTTACGCTGTTGCACCGCTGGTTGATTTCGTCGC

ACTGCCGCTGCCGCATGTTGACGGTCTGCCGGAGGGTGCGGAATCGACCA

ATGATGTGCCGTATGACAAATTTGAACTGCACCGTAAGGCGTTCGATGGT

CTGGCGGCCCCCGTTTAGCGAATTTCTGCGTGCAGCTTGCGCAGAAGGTGC

AGGTTCTCGCCCGGATTGGCTGATTGTGGACACCTTTCATCACTGGGCGG

CGGCGGCGGCGGTGGAAAACAAAGTGCCGTGTGTTATGCTGCTGCTGGGT

GCAGCAACGGTGATCGCTGGTTTCGCGCGTGGTGTTAGCGAACATGCGGC

GGCGGCGGTGGGTAAAGAACGTCCGGCTGCGGAAGCCCCGAGTTTTGAAA

CCGAACGTCGCAAGCTGATGACCACGCAGAATGCCTCCGGCATGACCGTG

GCAGAACGCTATTTCCTGACGCTGATGCGTAGCGATCTGGTTGCCATCCG

CTCTTGCGCAGAATGGGAACCGGAAAGCGTGGCAGCACTGACCACGCTGG

CAGGTAAACCGGTGGTTCCGCTGGGTCTGCTGCCGCCGAGTCCGGAAGGC

GGTCGTGGCGTTTCCAAAGAAGATGCTGCGGTCCGTTGGCTGGACGCACA

GCCGGCAAAGTCAGTCGTGTACGTCGCACTGGGTTCGGAAGTGCCGCTGC

GTGCGGAACAAGTTCACGAACTGGCACTGGGCCTGGAACTGAGCGGTGCT

CGCTTTCTGTGGGCGCTGCGTAAACCGACCGATGCACCGGACGCCGCAGT

GCTGCCGCCGGGTTTCGAAGAACGTACCCGCGGCCGTGGTCTGGTTGTCA

CGGGTTGGGTGCCGCAGATTGGCGTTCTGGCTCATGGTGCGGTGGCTGCG

TTTCTGACCCACTGTGGCTGGAACTCTACGATCGAAGGCCTGCTGTTCGG

TCATCCGCTGATTATGCTGCCGATCAGCTCTGATCAGGGTCCGAATGCGC

GCCTGATGGAAGGCCGTAAAGTCGGTATGCAAGTGCCGCGTGATGAATCA

GACGGCTCGTTTCGTCGCGAAGATGTTGCCGCAACCGTCCGCGCCGTGGCC

AGTTGAAGAAGACGGTCGTCGCGTCTTCACGGCTAACGCGAAAAAGATGC

AAGAAATTGTGGCCGATGGCGCATGCCACGAACGTTGTATTGACGGTTTT

ATCCAGCAACTGCGCAGTTACAAGGCGTAA

UGT76G1: Amino Acid sequence (SEQ ID NO: 7)
MENKTETTVRRRRRIILFPVPFQGHINPILQLANVLYSKGFSITIFHTNF

NKPKTSNYPHFTFRFILDNDPQDERISNLPTHGPLAGMRIPIINEHGADE

LRRELELLMLASEEDEEVSCLITDALWYFAQSVADSLNLRRLVLMTSSLF

NFHAFIVSLPQFDELGYLDPDDKTRLEEQASGFPMLKVKDIKSAYSNWQI

LKEILGKMIKQTKASSGVIWNSFKELEESELETVIREIPAPSFLIPLPKH

LTASSSSLLDHDRTVFQWLDQQPPSSVLYVSFGSTSEVDEKDFLEIARGL

VDSKQSFLWVVRPGFVKGSTWVEPLPDGFLGERGRIVKYVVPQQEVLAHG

AIGAFWTHSGWNSTLESVCEGVPMIFSDFGLDQPLNARYMSDVLKVGVYL

ENGWERGEIANA1RRVMVDEEGEYIRQNARVLKQKADVSLMKGGSSYESL

ESLVSYISSL

UGT76G1: DNA Sequence (SEQ ID NO: 8)
ATGGAGAATAAGACAGAAACAACCGTAAGACGGAGGCGGAGGATTATCTT

GTTCCCTGTACCATTTCAGGGCCATATTAATCCGATCCTCCAATTAGCAA

ACGTCCTCTACTCCAAGGGATTTTCAATAACAATCTTCCATACTAACTTT

AACAAGCCTAAAACGAGTAATTATCCTCACTTTACATTCAGGTTCATTCT

AGACAACGACCCTCAGGATGAGCGTATCTCAAATTTACCTACGCATGGCC

CCTTGGCAGGTATGCGAATACCAATAATCAATGAGCATGGAGCCGATGAA

CTCCGTCGCGAGTTAGAGCTTCTCATGCTCGCAAGTGAGGAAGACGAGGA

AGTTTCGTGCCTAATAACTGATGCGCTTTGGTACTTCGCCCAATCAGTCG

CAGACTCACTGAATCTACGCCGTTTGGTCCTTATGACAAGTTCATTATTC

AACTTTCACGCACATGTATCACTGCCGCAATTTGACGAGTTGGGTTACCT

GGACCCGGATGACAAAACGCGATTGGAGGAACAAGCGTCGGGCTTCCCCA

TGCTGAAAGTCAAAGATATTAAGAGCGCTTATAGTAATTGGCAAATTCTG

AAAGAAATTCTCGGAAAAATGATAAAGCAAACCAAAGCGTCCTCTGGAGT

AATCTGGAACTCCTTCAAGGAGTTAGAGGAATCTGAACTTGAAACGGTCA

TCAGAGAAATCCCCGCTCCCTCGTTCTTAATTCCACTACCCAAGCACCTT

ACTGCAAGTAGCAGTTCCCTCCTAGATCATGACCGAACCGTGTTTCAGTG

GCTGGATCAGCAACCCCCGTCGTCAGTTCTATATGTAAGCTTTGGGAGTA

CTTCGGAAGTGGATGAAAAGGACTTCTTAGAGATTGCGCGAGGGCTCGTG

GATAGCAAACAGAGCTTCCTGTGGGTAGTGAGACCGGGATTCGTTAAGGG

CTCGACGTGGGTCGAGCCGTTGCCAGATGGTTTTCTAGGGGAGAGAGGGA

GAATCGTGAAATGGGTTCCACAGCAAGAGGTTTTGGCTCACGGAGCTATA

GGGGCCTTTTGGACCCACTCTGGTTGGAATTCTACTCTTGAAAGTGTCTG

TGAAGGCGTTCCAATGATATTTTCTGATTTTGGGCTTGACCAGCCTCTAA

ACGCTCGCTATATGTCTGATGTGTTGAAGGTTGGCGTGTACCTGGAGAAT

GGTTGGGAAAGGGGGGAAATTGCCAACGCCATACGCCGGGTAATGGTGGA

CGAGGAAGGTGAGTACATACGTCAGAACGCTCGGGTTTTAAAACAAAAAG

CGGACGTCAGCCTTATGAAGGGAGGTAGCTCCTATGAATCCCTAGAATCC

TTGGTAAGCTATATATCTTCGTTATAA

UGT2E-B: Amino Acid sequence (SEQ ID NO: 9)

MATSDSIVDDRKQLHVATFPWLAFGHILPYLQLSKLIAEKGHKVSFLSTT

RNIQRLSSHISPLINVVQLTLPRVQELPEDAEATTDVHPEDIPYLKKASD

GLQPEVTRFLEQHSPDWIIYDYTHYWLPSIAASLGISRAHFSVTTPWAIA

YMGPSADAM1NGSDGRTTVEDLTTPPKWFPFPTKVCWRKHDLARLVPYKA

PGISDGYRMGMVLKGSDCLLSKCYHEFGTQWLPLLETLHQVPVVPVGLLP

PEIPGDEKDETWVSIKKWLDGKQKGSVVYVALGSEALVSQTEVVELALGL

ELSGLPFVWAYRKPKGPAKSDSVELPDGFVERTRDRGLVWTSWAPQLRIL

SHESVCGFLTHCGSGSIVEGLMFGHPLLMLPIFGDQPLNARLLEDKQVGI

EIPRNEEDGCLTKESVARSLRSVVVEKEGEIYKANARELSKIYNDTKVEK

EYVSQFVDYLEKNARAVAIDHES

UGT2E-B: DNA Sequence (SEQ ID NO: 10)

ATGGCTACCAGTGACTCCATAGTTGACGACCGTAAGCAGCTTCATGTTGC

GACGTTCCCATGGCTTGCTTTCGGTCACATCCTCCCTTACCTTCAGCTTT

CGAAATTGATAGCTGAAAAGGGTCACAAAGTCTCGTTTCTTTCTACCACC

AGAAACATTCAACGTCTCTCTTCTCATATCTCGCCACTCATAAATGTTGT

TCAACTCACACTTCCACGTGTCCAAGAGCTGCCGGAGGATGCAGAGGCGA

CCACTGACGTCCACCCTGAAGATATTCCATATCTCAAGAAGGCTTCTGAT

GGTCTTCAACCGGAGGTCACCCGGTTTCTAGAACAACACTCTCCGGACTG

GATTATTTATGATTATACTCACTACTGGTTGCCATCCATCGCGGCTAGCC

TCGGTATCTCACGAGCCCACTTCTCCGTCACCACTCCATGGGCCATTGCT

TATATGGGACCCTCAGCTGACGCCATGATAAATGGTTCAGATGGTCGAAC

CACGGTTGAGGATCTCACGACACCGCCCAAGTGGTTTCCCTTTCCGACCA

AAGTATGCTGGCGGAAGCATGATCTTGCCCGACTGGTGCCTTACAAAGCT

CCGGGGATATCTGATGGATACCGTATGGGATGGTTCTTAAGGGATCTGA

TTGTTTGCTTTCCAAATGTTACCATGAGTTTGGAACTCAATGGCTACCTC

TTTTGGAGACACTACACCAAGTACCGGTGGTTCCGGTGGGATTACTGCCA

CCCGGAAATACCCGGAGACGAGAAAGATGAAACATGGGTGTCAATCAAGAA

ATGGCTCGATGGTAAACAAAAAGGCAGTGTGGTGTACGTTGCATTAGGAA

GCGAGGCTTTGGTGAGCCAAACCGAGGTTGTTGAGTTAGCATTGGGTCTC

GAGCTTTCTGGGTTGCCATTTGTTTGGGCTTATAGAAAACCAAAAGGTCC

CGCGAAGTCAGACTCGGTGGAGTTGCCAGACGGGTTCGTGGAACGAACTC

GTGACCGTGGGTTGGTCTGGACGAGTTGGGCACCTCAGTTACGAATACTG

AGCCATGAGTCGGTTTGTGGTTTCTTGACTCATTGTGGTTCTGGATCAAT

TGTGGAAGGGCTAATGTTTGGTCACCCTCTAATCATGCTACCGATTTTTG

GGGACCAACCTCTGAATGCTCGATTACTGGAGGACAAACAGGTGGGAATC

GAGATACCAAGAAATGAGGAAGATGGTTGCTTGACCAAGGAGTCGGTTGC

TAGATCACTGAGGTCCGTTGTTGTGGAAAAAGAAGGGGAGATCTACAAGG

CGAACGCGAGGGAGCTGAGTAAAATCTATAACGACACTAAGGTTGAAAAA

GAATATGTAAGCCAATTCGTAGACTATTTGGAAAAGAATGCGCGTGCGGT

TGCCATCGATCATGAGAGTTAA

CP1: Amino Acid sequence (SEQ ID NO: 11)

MNWQILKEILGKMIKQTKASSGVIWNSFKELEESELETVIREIPAPSFLI

PLPKHLTASSSSLLDHDRTVFQWLDQQPPSSVLYVSFGSTSEVDEKDFLE

IARGLVDSKQSFLWVVRPGFVKGSTWVEPLPDGFLGERGRIVKWVPQQEV

LAHGAIGAFWTHSGWNSTLESVCEGVPMIFSDFGLDQPLNARYMSDVLKV

GVYLENGWERGEIANAIRRVMVDEEGEYIRQNARVLKQKADVSLMKGGSS

YESLESLVSYISSLENKTETTVRRRRRIILFPVPFQGHINPILQLANVLY

SKGFSITIFHTNFNKPKTSNYPHFTFRFILDNDPQDERISNLPTHGPLAG

MRIPIINEHGADELRRELELLMLASEEDEEVSCLITDALWYFAQSVADSL

NLRRLVLMTSSLFNFHAHVSLPQFDELGYLDPDDKTRLEEQASGFPMLKV

KDIKSAYS

CP1: DNA Sequence (SEQ ID NO: 12)

ATGAACTGGCAAATCCTGAAAGAAATCCTGGGTAAAATGATCAAACAAAC

CAAAGCGTCGTCGGGCGTTATCTGGAACTCCTTCAAAGAACTGGAAGAAT

CAGAACTGGAAACCGTTATTCGCGAAATCCCGGCTCCGTCGTTCCTGATT

CCGCTGCCGAAACATCTGACCGCGAGCAGCAGCAGCCTGCTGGATCACGA

CCGTACGGTCTTTCAGTGGCTGGATCAGCAACCGCCGTCATCGGTGCTGT

ATGTTTCATTCGGTAGCACCTCTGAAGTCGATGAAAAAGACTTTCTGGAA

ATCGCTCGCGGCCTGGTGGATAGTAAACAGTCCTTCCTGTGGGTGGTTCG

TCCGGGTTTTGTGAAAGGCAGCACGTGGGTTGAACCGCTGCCGGATGGCT

TCCTGGGTGAACGCGGCCGTATTGTCAAATGGGTGCCGCAGCAAGAAGTG

CTGGCACATGGTGCTATCGGCGCGTTTTGGACCCACTCTGGTTGGAACAG

TACGCTGGAATCCGTTTGCGAAGGTGTCCCGATGATTTTCAGCGATTTTG

GCCTGGACCAGCCGCTGAATGCCCGCTATATGTCTGATGTTCTGAAAGTC

GGTGTGTACCTGGAAAACGGTTGGGAACGTGGCGAAATTGCGAATGCCAT

CCGTCGCGTTATGGTCGATGAAGAAGGCGAATACATTCGCCAGAACGCTC

GTGTCCTGAAACAAAAAGCGGACGTGAGCCTGATGAAAGGCGGTAGCTCT

TATGAATCACTGGAATCGCTGGTTAGCTACATCAGTTCCCTGGAAAATAA

AACCGAAACCACGGTGCGTCGCCGTCGCCGTATTATCCTGTTCCCGGTTC

CGTTTCAGGGTCATATTAACCCGATCCTGCAACTGGCGAATGTTCTGTAT

TCAAAAGGCTTTTCGATCACCATCTTCCATACGAACTTCAACAAACCGAA

AACCAGTAACTACCCGCACTTTACGTTCCGCTTTATTCTGGATAACGACC

CGCAGGATGAACGTATCTCCAATCTGCCGACCCACGGCCCGCTGGCCGGT

ATGCGCATTCCGATTATCAATGAACACGGTGCAGATGAACTGCGCCGTGA

ACTGGAACTGCTGATGCTGGCCAGTGAAGAAGATGAAGAAGTGTCCTGTC

TGATCACCGACGCACTGTGGTATTTCGCCCAGAGCGTTGCAGATTCTCTG

AACCTGCGCCGTCTGGTCCTGATGACGTCATCGCTGTTCAATTTTCATGC

-continued
GCACGTTTCTCTGCCGCAATTTGATGAACTGGGCTACCTGGACCCGGATG
ACAAAACCCGTCTGGAAGAACAAGCCACTGGTTTTCCGATGCTGAAAGTC
AAAGACATTAAATCCGCCTATTCGTAA CP2: Amino Acid sequence (SEQ ID NO: 13)
MNWQILKEILGKMIKQTKASSGVIWNSFKELEESELETVIREIPAPSFLI
PLPKHLTASSSSLLDHDRTVFQWLDQQPPSSVLYVSFGSTSEVDEKDFLE
IARGLVDSKQSFLWVVRPGFVKGSTWVEPLPDGFLGERGRIVKWVPQQEV
LAHGAIGAFWTHSGWNSTLESVCEGVPMIFSDFGLDQPLNARYMSDVLKV
GVYLENGWERGEIANAIRRVMVDEEGEYIRQNARVLKQKADVSLMKGGSS
YESLESLVSYISSLYKDDSGYSSSYAAAAGMENKTETTVRRRRIILFPV
PFQGHINPILQLANVLYSKGFSITIFHTNFNKPKTSNYPHFTFRFILDND
PQDERISNLPTHGPLAGMRIPIINEHGADELRRELELLMLASEEDEEVSC
LITDALWYFAQSVADSLNLRRLVLMTSSLFNFHAHVSLPQFDELGYLDPD
DKTRLEEQASGFPMLKVKDIKSAYS CP2: DNA Sequence (SEQ ID NO: 14)
ATGAACTGGCAAATCCTGAAAGAAATCCTGGGTAAAATGATCAAACAAAC
CAAAGCGTCGTCGGGCGTTATCTGGAACTCCTTCAAAGAACTGGAAGAAT
CAGAACTGGAAACCGTTATTCGCGAAATCCCGGCTCCGTCGTTCCTGATT
CCGCTGCCGAAACATCTGACCGCGAGCAGCAGCAGCCTGCTGGATCACGA
CCGTACGGTCTTTCAGTGGCTGGATCAGCAACCGCCGTCATCGGTGCTGT
ATGTTTCATTCGGTAGCACCTCTGAAGTCGATGAAAAAGACTTTCTGGAA
ATCGCTCGCGGCCTGGTGGATAGTAAACAGTCCTTCCTGTGGGTGGTTCG
TCCGGGTTTTGTGAAAGGCAGCACGTGGGTTGAACCGCTGCCGGATGGCT
TCCTGGGTGAACGCGGCCGTATTGTCAAATGGGTGCCGCAGCAAGAAGTG
CTGGCACATGGTGCTATCGGCGCGTTTTGGACCCACTCTGGTTGGAACAG
TACGCTGGAATCCGTTTGCGAAGGTGTCCCGATGATTTTCAGCGATTTTG
GCCTGGACCAGCCGCTGAATGCCCGCTATATGTCTGATGTTCTGAAAGTC
GGTGTGTACCTGGAAAACGGTTGGGAACGTGGCGAAATTGCGAATGCCAT
CCGTCGCGTTATGGTCGATGAAGAAGGCGAATACATTCGCCAGAACGCTC
GTGTCCTGAAACAAAAAGCGGACGTGAGCCTGATGAAAGGCGGTAGCTCT
TATGAATCACTGGAATCGCTGGTTAGCTACATCAGTTCCCTGTACAAAGA
TGACAGCGGTTATAGCAGCAGCTATGCGGCGGCGGCGGGTATGGAAAATA
AAACCGAAACCACGGTGCGTCGCCGTCGCCGTATTATCCTGTTCCCGGTT
CCGTTTCAGGGTCATATTAACCCGATCCTGCAACTGGCGAATGTTCTGTA
TTCAAAAGGCTTTTCGATCACCATCTTCCATACGAACTTCAACAAACCGA
AAACCAGTAACTACCCGCACTTTACGTTCCGCTTTATTCTGGATAACGAC
CCGCAGGATGAACGTATCTCCAATCTGCCGACCCACGGCCCGCTGGCCGG
TATGCGCATTCCGATTATCAATGAACACGGTGCAGATGAACTGCGCCGTG
AACTGGAACTGCTGAGTATTTCGCCCAGAGCGTTGCAGATTCTCTGAACC
TGCGCCGTCTGGTCCTGATGACGTCATCGCTGTTCAATTTTCATGCGCAC
GTTTCTCTGCCGCAATTTGATGAACTGGGCTACCTGGACCCGGATGACAA -continued
AACCCGTCTGGAAGAACAAGCCAGTGGTTTTCCGATGCTGAAAGTCAAAG
ACATTAAATCCGCCTATTCGTAA GS: Amino Acid sequence (SEQ ID NO: 15)
MENKTETTVRRRRIILFPVPFQGHINPILQLANVLYSKGFSITIFHTNF
NKPKTSNYPHFTFRFILDNDPQDERISNLPTHGPLAGMRIPIINEHGADE
LRRELELLMLASEEDEEVSCLITDALWYFAQSVADSLNLRRLVLMTSSLF
NFHAHVSLPQFDELGYLDPDDKTRLEEQASGFPMLKVKDIKSAYSNWQIL
KEILGKMIKQTKASSGVIWNSFKELEESELETVIREIPAPSFLIPLPKHL
TASSSSLLDHDRTVFQWLDQQPPSSVLYVSFGSTSEVDEKDFLEIARGLV
DSKQSFLWVVRPGFVKGSTWVEPLPDGFLGERGRIVKWVPQQEVLAHGAI
GAFWTHSGVWSTLESVCEGVPMIFSDFGLDQPLNARYMSDVLKVGVYLEN
GVVERGEIANAIRRVMVDEEGEYIRQNARVLKQKADVSLMKGGSSYESLE
SLVSYISSLGSGANAERMITRVHSQRERLNETLVSERNEVLALLSRVEAK
GKGILQQNQIIAEFEALPEQTRKKLEGGPFFDLLKSTQEAIVLPPWVALA
VRPRPGVWEYLRVNLHALVVEELQPAEFLHFKEELVDGVKNGNFTLELDF
EPFNASIPRPTLHKYIGNGVDFLNRHLSAKLFHDKESLLPLLKFLRLHSH
QGKNLMLSEKIQNLNTLQHTLRKAEEYLAELKSETLYEEFEAKFEEIGLE
RGWGDNAERVLDMIRLLLDLLEAPDPCTLETFLGRVPMVFNVVILSPHGY
FAQDNVLGYPDTGGQVVYILDQVRALEIEMLQRIKQQGLNIKPRILILTR
LLPDAVGTTCGERLERVYDSEYCDILRVPFRTEKGIVRKWISRFEVWPYL
ETYTEDAAVELSKELNGKPDLIIGNYSDGNLVASLLAHKLGVTQCTIAHA
LEKTKYPDSDIYWKKLDDKYHFSCQFTADIFAMNHTDFIITSTFQEIAGS
KETVGQYESHTAFTLPGLYRVVHGIDVFDPKFNIVSPGADMSIYFPYTEE
KRRLTKFHSEIEELLYSDVENKEHLCVLKDKKKPILFTMARLDRVKNLSG
LVEWYGKNTRLRELANLVVVGGDRRKESKDNEEKAEMKKMYDLIEEYKLN
GQFRWISSQMDRVRNGELYRYICDTKGAFVQPALYEAFGLTVVEAMTCGL
PTFATCKGGPAEIIVHGKSGFHIDPYHGDQAADTLADFFTKCKEDPSHWD
EISKGGLQRIEEKYTWQIYSQRLLTLTGVYGFWKHVSNLDRLEARRYLEM
FYALKYRPLAQAVPLAQDD GS: DNA Sequence (SEQ ID NO: 16)
ATGGAGAATAAGACAGAAACAACCGTAAGACGGAGGCGGAGGATTATCTT
GTTCCCTGTACCATTTCAGGGCCATATTAATCCGATCCTCCAATTAGCAA
ACGTCCTCTACTCCAAGGGATTTTCAATAACAATCTTCCATACTAACTTT
AACAAGCCTAAAACGAGTAATTATCCTCACTTTACATTCAGGTTCATTCT
AGACAACGACCCTCAGGATGAGCGTATCTCAAATTTACCTACGCATGGCC
CCTTGGCAGGTATGCGAATACCAATAATCAATGAGCATGGAGCCGATGAA
CTCCGTCGCGAGTTAGAGCTTCTCATGCTCGCAAGTGAGGAAGACGAGGA
AGTTTCGTGCCTAATAACTGATGCGCTTTGGTACTTCGCCCAATCAGTCG
CAGACTCACTGAATCTACGCCGTTTGGTCCTTATGACAAGTTCATTATTC
AACTTTCACGCACATGTATCACTGCCGCAATTTGACGAGTTGGGTTACCT

```
GGACCCGGATGACAAAACGCGATTGGAGGAACAAGCGTCGGGCTTCCCCA
TGCTGAAAGTCAAAGATATTAAGAGCGCTTATAGTAATTGGCAAATTCTG
AAAGAAATTCTCGGAAAAATGATAAAGCAAACCAAAGCGTCCTCTGGAGT
AATCTGGAACTCCTTCAAGGAGTTAGAGGAATCTGAACTTGAAACGGTCA
TCAGAGAAATCCCCGCTCCCTCGTTCTTAATTCCACTACCCAAGCACCTT
ACTGCAAGTAGCAGTTCCCTCCTAGATCATGACCGAACCGTGTTTCAGTG
GCTGGATCAGCAACCCCGTCGTCAGTTCTATATGTAAGCTTTGGGAGTA
CTTCGGAAGTGGATGAAAAGGACTTCTTAGAGATTGCGCGAGGGCTCGTG
GATAGCAAACAGAGCTTCCTGTGGGTAGTGAGACCGGGATTCGTTAAGGG
CTCGACGTGGGTCGAGCCGTTGCCAGATGGTTTTCTAGGGGAGAGAGGGA
GAATCGTGAAATGGGTTCCACAGCAAGAGGTTTTGGCTCACGGAGCTATA
GGGGCCTTTTGGACCCACTCTGGTTGGAATTCTACTCTTCAAAGTGTCTG
TGAAGGCGTTCCAATGATATTTTCTGATTTTGGGCTTGACCAGCCTCTAA
ACGCTCGCTATATGTCTGATGTGTTGAAGGTTGGCGTGTACCTGGAGAAT
GGTTGGGAAAGGGGGGAAATTGCCAACGCCATACGCCGGGTAATGGTGGA
CGAGGAAGGTGAGTACATACGTCAGAACGCTCGGGTTTTAAAACAAAAAG
CGGACGTCAGCCTTATGAAGGGAGGTAGCTCCTATGAATCCCTAGAATCC
TTGGTAAGCTATATATCTTCGTTAGGTTCTGGTGCAAACGCTGAACGTAT
GATAACGCGCGTCCACAGCCAACGTGAGCGTTTGAACGAAACGCTTGTTT
CTGAGAGAAACGAAGTCCTTGCCTTGCTTTCCAGGGTTGAAGCCAAAGGT
AAAGGTATTTTACAACAAAACCAGATCATTGCTGAATTCGAAGCTTTGCC
TGAACAAACCCGGAAGAAACTTGAAGGTGGTCCTTTCTTTGACCTTCTCA
AATCCACTCAGGAAGCAATTGTGTTGCCACCATGGGTTGCTCTAGCTGTG
AGGCCAAGGCCTGGTGTTTGGGAATACTTACGAGTCAATCTCCATGCTCT
TGTCGTTGAAGAACTCCAACCTGCTGAGTTTCTTCATTTCAAGGAAGAAC
TCGTTGATGGAGTTAAGAATGGTAATTTCACTCTTGAGCTTGATTTCGAG
CCATTCAATGCGTCTATCCCTCGTCCAACACTCCACAAATACATTGGAAA
TGGTGTTGACTTCCTTAACCGTCATTTATCGGCTAAGCTCTTCCATGACA
AGGAGAGTTTGCTTCCATTGCTTAAGTTCCTTCGTCTTCACAGCCACCAG
GGCAAGAACCTGATGTTGAGCGAGAAGATTCAGAACCTCAACACTCTGCA
ACACACCTTGAGGAAAGCAGAAGAGTATCTAGCAGAGCTTAAGTCCGAAA
CACTGTATGAAGAGTTTGAGGCCAAGTTTGAGGAGATTGGTCTTGAGAGG
GGATGGGGAGACAATGCAGAGCGTGTCCTTGACATGATACGTCTTCTTTT
GGACCTTCTTGAGGCGCCTGATCCTTGCACTCTTGAGACTTTTCTTGGAA
GAGTACCAATGGTGTTCAACGTTGTGATCCTCTCTCCACATGGTTACTTT
GCTCAGGACAATGTTCTTGGTTACCCTGACACTGGTGGACAGGTTGTTTA
CATTCTTGATCAAGTTCGTGCTCTGGAGATAGAGATGCTTCAACGTATTA
AGCAACAAGGACTCAACATTAAACCAAGGATTCTCATTCTAACTCGACTT
CTACCTGATGCGGTAGGAACTACATGCGGTGAACGTCTCGAGAGAGTTTA
TGATTCTGAGTACTGTGATATTCTTCGTGTGCCCTTCAGAACAGAGAAGG
GTATTGTTCGCAAATGGATCTCAAGGTTCGAAGTCTGGCCATATCTAGAG
```

```
ACTTACACCGAGGATGCTGCGGTTGAGCTATCGAAAGAATTGAATGGCAA
GCCTGACCTTATCATTGGTAACTACAGTGATGGAAATCTTGTTGCTTCTT
TATTGGCTCACAAACTTGGTGTCACTCAGTGTACCATTGCTCATGCTCTT
GAGAAAACAAAGTACCCGGATTCTGATATCTACTGGAAGAAGCTTGACGA
CAAGTACCATTTCTCATGCCAGTTCACTGCGGATATTTTCGCAATGAACC
ACACTGATTTCATCATCACTAGTACTTTCCAAGAAATTGCTGGAAGCAAA
GAAACTGTTGGGCAGTATGAAAGCCACACAGCCTTTACTCTTCCCGGATT
GTATCGAGTTGTTCACGGGATTGATGTGTTTGATCCCAAGTTCAACATTG
TCTCTCCTGGTGCTGATATGAGCATCTACTTCCCTTACACAGAGGAGAAG
CGTAGATTGACTAAGTTCCACTCTGAGATCGAGGAGCTCCTCTACAGCGA
TGTTGAGAACAAAGAGCACTTATGTGTGCTCAAGGACAAGAAGAAGCCGA
TTCTCTTCACAATGGCTAGGCTTGATCGTGTCAAGAACTTGTCAGGTCTT
GTTGAGTGGTACGGGAAGAACACCCGCTTGCGTGAGCTAGCTAACTTGGT
TGTTGTTGGAGGAGACAGGAGGAAAGAGTCAAAGGACAATGAAGAGAAAG
CAGAGATGAAGAAAATGTATGATCTCATTGAGGAATACAAGCTAAACGGT
CAGTTCAGGTGGATCTCCTCTCAGATGGACCGGGTAAGGAACGGTGAGCT
GTACCGGTACATCTGTGACACCAAGGGTGCTTTTGTCCAACCTGCATTAT
ATGAAGCCTTTGGGTTAACTGTTGTGGAGGCTATGACTTGTGGTTTACCG
ACTTTCGCCACTTGCAAAGGTGGTCCAGCTGAGATCATTGTGCACGGTAA
ATCGGGTTTCCACATTGACCCTTACCATGGTGATCAGGCTGCTGATACTC
TTGCTGATTTCTTCACCAAGTGTAAGGAGGATCCATCTCACTGGGATGAG
ATCTCAAAAGGAGGGCTTCAGAGGATTGAGGAGAAATACACTTGGCAAAT
CTATTCACAGAGGCTCTTGACATTGACTGGTGTGTATGGATTCTGGAAGC
ATGTCTCGAACCTTGACCGTCTTGAGGCTCGCCGTTACCTTGAAATGTTC
TATGCATTGAAGTATCGCCCATTGGCTCAGGCTGTTCCTCTTGCACAAGA
TGATTGA

AtSUS1: Amino Acid sequence
                                              (SEQ ID NO: 17)
MANAERMITRVHSQRERLNETLVSHRNEVLALLSRVEAKGKGILQQNQII
AEFEALPEQTRKKLEGGPFFDLLKSTQEAIVLPPWVALAVRPRPGVWEYL
RVNLHALVVEELQPAEFLHFKEELVDGVKNGNFTLELDFEPFNASIPRPT
LHKYIGNGVDFLNRHLSAKLFHDKESLLPLLKFLRLHSHQGKNLMLSEKI
QNLNTLQHTLRKAEEYLAELKSETLYEEFEAKFEEIGLERGWGDNAERVL
DMIRLLLDLLEAPDPCTLETFLGRVPMVFNVVBLSPHGYFAQDNVLGYPD
TGGQVVYILDQVRALEIEMLQRIKQQGLNIKPRILILTRLLPDAVGTTCG
ERLERVYDSEYCDILRVPFRTEKGIVRKWISRFEVWPYLETYTEDAAVEL
SKELNGKPDLIIGNYSDGNXVASLLAHKLGVTQCTIAHALEKTKYPDSDI
YWKKLDDKYHFSCQFTADIFAMNHTDFIITSTFQEIAGSKETVGQYESHT
AFTLPGLYRVVHGIDVFDPKFNIVSPGADMSIYFPYTEEKRRLTKFHSEI
EELLYSDVENKEHLCVLKDKKKPILFTMARLDRVKNLSGLVEWYGKNTRL
RELANLVVGGDRRKESKDNEEKAEMKKMYDLIEEYKLNGQFRVVISSQM
```

DRVRNGELYRYICDTKGAFVQPALYEAFGLTVVEAMTCGLPTFATCKGGP

AEIIVHGKSGFHIDPYHGDQAADTLADFFTKCKEDPSHWDEISKGGLQRI

EEKYTWQIYSQRLLTLTGVYGFWKHVSNLDRLEARRYLEMFYALKYRPLA

QAVPLAQDD

AtSUS1: DNA Sequence (SEQ ID NO: 18)
ATGGCAAACGCTGAACGTATGATTACCCGTGTCCACTCCCAACGCGAACG

CCTGAACGAAACCCTGGTGTCGGAACGCAACGAAGTTCTGGCACTGCTGA

GCCGTGTGGAAGCTAAGGGCAAAGGTATTCTGCAGCAAAACCAGATTATC

GCGGAATTTGAAGCCCTGCCGGAACAAACCCGCAAAAAGCTGGAAGGCGG

TCCGTTTTTCGATCTGCTGAAATCTACGCAGGAAGCGATCGTTCTGCCGC

CGTGGGTCGCACTGGCAGTGCGTCCGCGTCCGGGCGTTTGGGAATATCTG

CGTGTCAACCTGCATGCACTGGTGGTTGAAGAACTGCACCCGGCTGAATT

TCTGCACTTCAAGGAAGAACTGGTTGACGGCGTCAAAAACGGTAATTTTA

CCCTGGAACTGGATTTTGAACCGTTCAATGCCAGTATCCCGCGTCCGACG

CTGCATAAATATATTGGCAACGGTGTGGACTTTCTGAATCGCCATCTGAG

CGCAAAGCTGTTCCACGATAAAGAATCTCTGCTGCCGCTGCTGAAATTCC

TGCGTCTGCATAGTCACCAGGGCAAGAACCTGATGCTGTCCGAAAAAATT

CAGAACCTGAATACCCTGCAACACACGCTGCGCAAGGCGGAAGAATACCT

GGCCGAACTGAAAGTGAAACCCTGTACGAAGAATTCGAAGCAAAGTTCG

AAGAAATTGGCCTGGAACGTGGCTGGGGTGACAATGCTGAACGTGTTCTG

GATATGATCCGTCTGCTGCTGGACCTGCTGGAAGCACCGGACCCGTGCAC

CCTGGAAACGTTTCTGGGTCGCGTGCCGATGGTTTTCAACGTCGTGATTC

TGTCCCCGCATGGCTATTTTGCACAGGACAATGTGCTGGGTTACCCGGAT

ACCGGCGGTCAGGTTGTCTATATTCTGGATCAAGTTCGTGCGCTGGAAAT

TGAAATGCTGCAGCGCATCAAGCAGCAAGGCCTGAACATCAAACCGCGTA

TTCTGATCCTGACCCGTCTGCTGCCGGATGCAGTTGGTACCACGTGCGGT

GAACGTCTGGAACGCGTCTATGACAGCGAATACTGTGATATTCTGCGTGT

CCCGTTTCGCACCGAAAAGGGTATTGTGCGTAAATGGATCAGTCGCTTCG

AAGTTTGGCCGTATCTGGAAACCTACACGGAAGATGCGGCCGTGGAACTG

TCCAAGGAACTGAATGGCAAACCGGACCTGATTATCGGCAACTATAGCGA

TGGTAATCTGGTCGCATCTCTGCTGGCTCATAAACTGGGTGTGACCCAGT

GCACGATTGCACACGCTCTGGAAAAGACCAAATATCCGGATTCAGACATC

TACTGGAAAAAGCTGGATGACAAATATCATTTTTCGTGTCAGTTCACCGC

GGACATTTTTGCCATGAACCACACGGATTTTATTATCACCAGTACGTTCC

AGGAAATCGCGGGCTCCAAAGAAACCGTGGGTCAATACGAATCACATACC

GCCTTCACGCTGCCGGGCCTGTATCGTGTGGTTCACGGTATCGATGTTTT

TGACCCGAAATTCAATATTGTCAGTCCGGGCGCGGATATGTCCATCTATT

TTCCGTACACCGAAGAAAAGCGTCGCCTGACGAAATTCCATTCAGAAATT

GAAGAACTGCTGTACTCGGACGTGGAAAACAAGGAACACCTGTGTGTTCT

GAAAGATAAAAAGAAACCGATCCTGTTTACCATGGCCCGTCTGGATCGCG

TGAAGAATCTGTCAGGCCTGGTTGAATGGTATGGTAAAAACACGCGTCTG

CGCGAACTGGCAAATCTGGTCGTGGTTGGCGGTGACCGTCGCAAGGAATC

GAAAGATAACGAAGAAAAGGCTGAAATGAAGAAAATGTACGATCTGATCG

AAGAATACAAGCTGAACGGCCAGTTTCGTTGGATCAGCTCTCAAATGGAC

CGTGTGCGCAATGGCGAACTGTATCGCTACATTTGCGATACCAAGGGTGC

GTTTGTTCAGCCGGCACTGTACGAAGCTTTCGGCCTGACCGTCGTGGAAG

CCATGACGTGCGGTCTGCCGACCTTTGCGACGTGTAAAGGCGGTCCGGCC

GAAATTATCGTGCATGGCAAATCTGGTnCCATATCGATCCGTATCACGGT

GATCAGGCAGCTGACACCCTGGCGGATTTCTTTACGAAGTGTAAAGAAGA

CCCGTCACACTGGGATGAAATTTCGAAGGGCGGTCTGCAACGTATCGAAG

AAAAATATACCTGGCAGATTTACAGCCAACGCCTGCTGACCCTGACGGGC

GTCTACGGTTTTTGGAAACATGTGTCTAATCTGGATCGCCTGGAAGCCCG

TCGCTATCTGGAAATGTTTTACGCACTGAAGTATCGCCCGCTGGCACAAG

CCGTTCCGCTGGCACAGGACGACTAA

NX114: Amino Acid Sequence (SEQ ID NO: 19)
MENGSSPLHVVIFPWLAFGHLLPFLDLAERLAARGHRVSFVSTPRNLARL

RPVRPALRGLVDLVALPLPRVHGLPDGAEATSDVPFEKFELHRKAFDGLA

APFSAFLDAACAGDKRPDWVIPDFMHYWVAAAAQKRGVPCAVLIPCSADV

MALYGQPTETSTEQPEAIARSMAAEAPSFEAERNTEEYGTAGASGVSIMT

RFSLTLKWSKLVALRSCPELEPGVFTTLTRVYSKPVVPFGLLPPRRDGAH

GVRKNGEDDGAIIRWLDEQPAKSVVYVALGSEAPVSADLLRELAHGLELA

GTRFLWALRRPAGVNDGDSILPNGFLERTGERGLVTTGWVPQVSILAHAA

VCAFLTHCGWGSVVEGLQFGHPLIMLPIIGDQGPNARFLEGRKVGVAVPR

NHADGSFDRSGVAGAVRAVAVEEEGKAFAANARKLQEIVADRERDERCTD

GFIHHLTSWNELEA

NX114: DNA Sequence (SEQ ID NO: 20)
ATGGAAAATGGTAGCAGTCCGCTGCATGTTGTTATTTTTCCGTGGCTGGC

ATTTGGTCATCTGCTGCCGTTTCTGGATCTGGCAGAACGTCTGGCAGCAC

GTGGTCATCGTGTTAGCTTTGTTAGCACACCGCGTAATCTGGCACGTCTG

CGTCCGGTTCGTCCGGCACTGCGTGGTCTGGTTGATCTGGTTGCACTGCC

GCTGCCTCGTGTTCATGGTCTGCCGGATGGTGCCGAAGCAACCAGTGATG

TTCCGTTTGAAAAATTTGAACTGCACCGCAAAGCATTTGATGGCCTGGCT

GCACCGTTTAGCGCATTTCTGGATGCAGCATGTGCCGGTGATAAACGTCC

GGATTGGGTTATTCCGGATTTTATGCATTATTGGGTTGCAGCAGCAGCAC

AGAAACGTGGTGTTCCGTGTGCAGTTCTGATTCCGTGTAGCGCAGATGTT

ATGGCACTGTATGGTCAGCCGACCGAAACCAGCACCGAACAGCCGGAAGC

AATTGCACGTAGCATGGCAGCAGAAGCACCGAGCTTTGAAGCAGAACGTA

ATACCGAAGAATATGGTACAGCCGGTGCAAGCGGTGTTAGCATTATGACC

CGTTTTAGTCTGACCCTGAAATGGTCAAAACTGGTTGCCCTGCGTAGCTG

TCCGGAACTGGAACCGGGTGTTTTTACCACACTGACCCGTGTTTATAGCA

AACCGGTTGTGCCGTTTGGTCTGCTGCCTCCGCGTCGTGATGGTGCACAT

-continued

GGTGTTCGTAAAAATGGTGAAGATGATGGTGCCATTATTCGTTGGCTGGA

TGAACAGCCTGCAAAAAGCGTTGTTTATGTTGCACTGGGTAGCGAAGCAC

CGGTTTCAGCCGATCTGCTGCGTGAACTGGCACATGGTCTGGAATTAGCA

GGCACCCGTTTTCTGTGGGCTCTGCGTCGTCCTGCCGGTGTTAATGATGG

TGATAGCATTCTGCCGAATGGTTTTCTGGAACGTACCGGTGAACGCGGTC

TGGTTACCACCGGTTGGGTTCCGCAGGTTAGTATTCTGGCCCATGCAGCA

GTTTGTGCATTTCTGACCCATTGTGGTTGGGGTAGCGTTGTTGAAGGTTT

-continued

ACAGTTTGGCCATCCGCTGATTATGCTGCCGATTATTGGTGATCAGGGTC

CGAATGCACGCTTTCTGGAAGGTCGTAAAGTTGGTGTTGCAGTTCCGCGT

AACCATGCAGATGGTAGCTTTGATCGTAGCGGTGTTGCCGGTGCCGTTCG

TGCAGTTGCAGTTGAAGAAGAAGGTAAAGCCTTTGCAGCAAATGCCCGTA

AACTGCAAGAAATTGTTGCAGATCGTGAACGTGATGAACGTTGTACCGAT

GGTTTTATTCATCATCTGACCAGCTGGAATGAACTGGAAGCATAA

What is claimed is:

1. A biosynthetic method of preparing rebaudioside N, the method comprising:

reacting a steviol glycoside composition comprising rebaudioside A with a glucose donor moiety in the presence of a first recombinant polypeptide having glucosyltransferase activity to produce rebaudioside I, wherein said first recombinant polypeptide comprises (i) an amino acid sequence having at least 95% sequence identity to SEQ ID NO: 7, SEQ ID NO: 11, or SEQ ID NO: 13, or (ii) an amino acid sequence having at least 97% sequence identity to SEQ ID NO: 15; and reacting said rebaudioside I with a rhamnose donor moiety in the presence of a second recombinant polypeptide having 1,2-rhamnosyltransferase activity to produce rebaudioside N; wherein said second recombinant polypeptide comprises an amino acid sequence having at least 95% sequence identity to SEQ ID NO: 3.

2. The method of claim 1, wherein said second recombinant polypeptide comprises the amino acid sequence of SEQ ID NO: 3.

3. The method of claim 1, wherein said first recombinant polypeptide comprises an amino acid sequence having at least 98% identity to SEQ ID NO: 7, SEQ ID NO: 11, SEQ ID NO: 13, or SEQ ID NO: 15.

4. The method of claim 3, wherein said first recombinant polypeptide comprises the amino acid sequence of SEQ ID NO: 7.

5. The method of claim 3, wherein said first recombinant polypeptide comprises the amino acid sequence of SEQ ID NO: 11.

6. The method of claim 3, wherein said first recombinant polypeptide comprises the amino acid sequence of SEQ ID NO: 13.

7. The method of claim 3, wherein said first recombinant polypeptide comprises the amino acid sequence of SEQ ID NO: 15.

8. The method of claim 1, wherein the rhamnose donor moiety is UDP-L-rhamnose.

9. The method of claim 1, wherein the glucose donor moiety is generated in situ.

10. The method of claim 1, comprising reacting said steviol glycoside composition comprising rebaudioside A with a glucose donor moiety in the presence of a third recombinant polypeptide having sucrose synthase activity.

11. The method of claim 1, comprising expressing said second recombinant polypeptide in a transformed cell.

12. The method of claim 11, wherein the transformed cell is selected from the group consisting of a yeast, a non-steviol glycoside producing plant, an alga, a fungus, and a bacterium.

13. The method of claim 12, wherein the transformed cell is a bacterium or yeast selected from the group consisting of *Escherichia; Salmonella; Bacillus; Acinetobacter; Streptomyces; Corynebacterium; Methylosinus; Methylomonas; Rhodococcus; Pseudomonas; Rhodobacter; Synechocystis; Saccharomyces; Zygosaccharomyces; Kluyveromyces; Candida; Hansenula; Debaryomyces; Mucor; Pichia; Torulopsis; Aspergillus; Arthrobotlys; Brevibacteria; Microbacterium; Arthrobacter; Citrobacter; Klebsiella; Pantoea*; and *Clostridium*.

14. The method of claim 13, comprising isolating said second recombinant polypeptide from the transformed cell and the step of reacting the rebaudioside I with the second recombinant polypeptide is performed in vitro.

15. The method of claim 11, wherein the step of reacting the rebaudioside I with the second recombinant polypeptide is performed in the transformed cell.

16. The method of claim 1, further comprising isolating rebaudioside N from the steviol glycoside composition.

17. The method of claim 1, further comprising purifying rebaudioside N to obtain a steviol glycoside composition enriched with rebaudioside N.

* * * * *

SEQUENCE LISTING

<160> NUMBER OF SEQ ID NOS: 20

<210> SEQ ID NO 1
<211> LENGTH: 462
<212> TYPE: PRT
<213> ORGANISM: Oryza sativa

<400> SEQUENCE: 1

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Gly Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val

|     |     |     |     | 275 |     |     |     |     | 280 |     |     |     |     | 285 |     |
| --- | --- | --- | --- | --- | --- | --- | --- | --- | --- | --- | --- | --- | --- | --- | --- |
| Glu | Lys | Val | His | Glu | Leu | Ala | Leu | Gly | Leu | Glu | Leu | Ala | Gly | Thr | Arg |
|     |     |     |     | 290 |     |     |     |     | 295 |     |     |     |     | 300 |     |
| Phe | Leu | Trp | Ala | Leu | Arg | Lys | Pro | Thr | Gly | Val | Ser | Asp | Ala | Asp | Leu |
| 305 |     |     |     |     | 310 |     |     |     |     | 315 |     |     |     |     | 320 |
| Leu | Pro | Ala | Gly | Phe | Glu | Arg | Thr | Arg | Gly | Arg | Gly | Val | Val | Ala |     |
|     |     |     |     |     | 325 |     |     |     |     | 330 |     |     |     |     | 335 |
| Thr | Arg | Trp | Val | Pro | Gln | Met | Ser | Ile | Leu | Ala | His | Ala | Val | Gly |     |
|     |     |     | 340 |     |     |     |     | 345 |     |     |     |     | 350 |     |     |
| Ala | Phe | Leu | Thr | His | Cys | Gly | Trp | Asn | Ser | Thr | Ile | Glu | Gly | Leu | Met |
|     |     | 355 |     |     |     |     | 360 |     |     |     |     | 365 |     |     |     |
| Phe | Gly | His | Pro | Leu | Ile | Met | Leu | Pro | Ile | Phe | Gly | Asp | Gln | Gly | Pro |
|     | 370 |     |     |     |     | 375 |     |     |     |     | 380 |     |     |     |     |
| Asn | Ala | Arg | Leu | Ile | Glu | Ala | Lys | Asn | Ala | Gly | Leu | Gln | Val | Ala | Arg |
| 385 |     |     |     |     | 390 |     |     |     |     | 395 |     |     |     |     | 400 |
| Asn | Asp | Gly | Asp | Gly | Ser | Phe | Asp | Arg | Glu | Gly | Val | Ala | Ala | Ala | Ile |
|     |     |     |     | 405 |     |     |     |     | 410 |     |     |     |     | 415 |     |
| Arg | Ala | Val | Ala | Val | Glu | Glu | Glu | Ser | Ser | Lys | Val | Phe | Gln | Ala | Lys |
|     |     |     | 420 |     |     |     |     | 425 |     |     |     |     | 430 |     |     |
| Ala | Lys | Lys | Leu | Gln | Glu | Ile | Val | Ala | Asp | Met | Ala | Cys | His | Glu | Arg |
|     |     | 435 |     |     |     |     | 440 |     |     |     |     | 445 |     |     |     |
| Tyr | Ile | Asp | Gly | Phe | Ile | Gln | Gln | Leu | Arg | Ser | Tyr | Lys | Asp |     |     |
|     | 450 |     |     |     |     | 455 |     |     |     |     | 460 |     |     |     |     |

<210> SEQ ID NO 2
<211> LENGTH: 1389
<212> TYPE: DNA
<213> ORGANISM: Oryza sativa

<400> SEQUENCE: 2

| atggattcgg gttactcttc ctcctatgcg gcggctgcgg gtatgcacgt tgttatctgt | 60 |
| --- | --- |
| ccgtggctgg cttttggtca cctgctgccg tgcctggatc tggcacagcg tctggcttca | 120 |
| cgcggccatc gtgtcagctt cgtgtctacc ccgcgcaata tttcgcgtct gccgccggtt | 180 |
| cgtccggcac tggctccgct ggttgcattt gtcgctctgc cgctgccgcg cgtggaaggt | 240 |
| ctgccggatg gtgcggaaag taccaacgac gtgccgcatg atcgcccgga catggttgaa | 300 |
| ctgcaccgtc gtgcattcga tggtctggca gcaccgtttt ccgaatttct gggtacggcg | 360 |
| tgcgccgatt gggtgatcgt tgacgtcttt catcactggg cggcggcggc ggcgctggaa | 420 |
| cataaagttc cgtgtgcaat gatgctgctg ggctcagctc acatgattgc gtcgatcgca | 480 |
| gaccgtcgcc tggaacgtgc agaaaccgaa gtccggctgc ggccggcca gggtcgcccg | 540 |
| gcagctgcgc cgaccttcga agtggcccgc atgaaactga tcgtacgaa aggcagctct | 600 |
| ggtatgagcc tggcagaacg ctttagtctg accctgtccc gtagttccct ggtggttggt | 660 |
| cgcagttgcg ttgaatttga accggaaacc gtcccgctgc tgtccacgct gcgtggtaaa | 720 |
| ccgatcacct ttctgggtct gatgccgccg ctgcatgaag gccgtcgcga agatggtgaa | 780 |
| gacgcaacgg tgcgttggct ggatgcacag ccggctaaaa gcgtcgtgta tgtcgccctg | 840 |
| ggctctgaag tgccgctggg tgtggaaaaa gttcacgaac tggcactggg cctggaactg | 900 |
| gctggcaccc gcttcctgtg ggcactgcgt aaaccgacgg tgtgagcga tgcggacctg | 960 |
| ctgccggccg ttttgaaga acgtaccgc ggcgtggtg ttgtcgcaac gcgttgggtc | 1020 |
| ccgcaaatga gcattctggc gcatgccgca gtgggcgcct ttctgaccca ctgtggttgg | 1080 |

-continued

```
aacagcacga tcgaaggcct gatgtttggt cacccgctga ttatgctgcc gatcttcggc    1140
gatcagggtc cgaacgcacg tctgattgaa gcgaaaaatg ccggcctgca agttgcgcgc    1200
aacgatggcg acggttcttt cgaccgtgag ggtgtggctg cggccattcg cgcagtggct    1260
gttgaagaag aatcatcgaa agtttttcag gcgaaagcca aaaaactgca agaaatcgtc    1320
gcggatatgg cctgccacga acgctacatt gatggtttca ttcagcaact gcgctcctac    1380
aaagactaa                                                            1389
```

```
<210> SEQ ID NO 3
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 3
```

| | | | | | | | | | | | | | | | |
|---|---|---|---|---|---|---|---|---|---|---|---|---|---|---|---|
| Met | Gly | Ser | Ser | Gly | Met | Ser | Leu | Ala | Glu | Arg | Phe | Ser | Leu | Thr | Leu |
| 1 | | | | 5 | | | | | 10 | | | | | 15 | |
| Ser | Arg | Ser | Ser | Leu | Val | Val | Gly | Arg | Ser | Cys | Val | Glu | Phe | Glu | Pro |
| | | | 20 | | | | | 25 | | | | | 30 | | |
| Glu | Thr | Val | Pro | Leu | Leu | Ser | Thr | Leu | Arg | Gly | Lys | Pro | Ile | Thr | Phe |
| | | | | 35 | | | | | 40 | | | | | 45 | |
| Leu | Gly | Leu | Met | Pro | Pro | Leu | His | Glu | Gly | Arg | Arg | Glu | Asp | Gly | Glu |
| | | 50 | | | | | 55 | | | | | 60 | | | |
| Asp | Ala | Thr | Val | Arg | Trp | Leu | Asp | Ala | Gln | Pro | Ala | Lys | Ser | Val | Val |
| 65 | | | | | 70 | | | | | 75 | | | | | 80 |
| Tyr | Val | Ala | Leu | Gly | Ser | Glu | Val | Pro | Leu | Gly | Val | Glu | Lys | Val | His |
| | | | | 85 | | | | | 90 | | | | | 95 | |
| Glu | Leu | Ala | Leu | Gly | Leu | Glu | Leu | Ala | Gly | Thr | Arg | Phe | Leu | Trp | Ala |
| | | | 100 | | | | | 105 | | | | | 110 | | |
| Leu | Arg | Lys | Pro | Thr | Gly | Val | Ser | Asp | Ala | Asp | Leu | Leu | Pro | Ala | Gly |
| | | 115 | | | | | 120 | | | | | 125 | | | |
| Phe | Glu | Glu | Arg | Thr | Arg | Gly | Arg | Gly | Val | Val | Ala | Thr | Arg | Trp | Val |
| 130 | | | | | 135 | | | | | 140 | | | | | |
| Pro | Gln | Met | Ser | Ile | Leu | Ala | His | Ala | Ala | Val | Gly | Ala | Phe | Leu | Thr |
| 145 | | | | | 150 | | | | | 155 | | | | | 160 |
| His | Cys | Gly | Trp | Asn | Ser | Thr | Ile | Glu | Gly | Leu | Met | Phe | Gly | His | Pro |
| | | | | 165 | | | | | 170 | | | | | 175 | |
| Leu | Ile | Met | Leu | Pro | Ile | Phe | Gly | Asp | Gln | Gly | Pro | Asn | Ala | Arg | Leu |
| | | | 180 | | | | | 185 | | | | | 190 | | |
| Ile | Glu | Ala | Lys | Asn | Ala | Gly | Leu | Gln | Val | Ala | Arg | Asn | Asp | Gly | Asp |
| | | 195 | | | | | 200 | | | | | 205 | | | |
| Gly | Ser | Phe | Asp | Arg | Glu | Gly | Val | Ala | Ala | Ile | Arg | Ala | Val | Ala |
| | 210 | | | | | 215 | | | | | 220 | | | | |
| Val | Glu | Glu | Glu | Ser | Ser | Lys | Val | Phe | Gln | Ala | Lys | Ala | Lys | Lys | Leu |
| 225 | | | | | 230 | | | | | 235 | | | | | 240 |
| Gln | Glu | Ile | Val | Ala | Asp | Met | Ala | Cys | His | Glu | Arg | Tyr | Ile | Asp | Gly |
| | | | | 245 | | | | | 250 | | | | | 255 | |
| Phe | Ile | Gln | Gln | Leu | Arg | Ser | Tyr | Lys | Asp | Asp | Ser | Gly | Tyr | Ser | Ser |
| | | | 260 | | | | | 265 | | | | | 270 | | |
| Ser | Tyr | Ala | Ala | Ala | Ala | Gly | Met | His | Val | Val | Ile | Cys | Pro | Trp | Leu |
| | | 275 | | | | | 280 | | | | | 285 | | | |
| Ala | Phe | Gly | His | Leu | Leu | Pro | Cys | Leu | Asp | Leu | Ala | Gln | Arg | Leu | Ala |
| | 290 | | | | | 295 | | | | | 300 | | | | |

```
Ser Arg Gly His Arg Val Ser Phe Val Ser Thr Pro Arg Asn Ile Ser
305                 310                 315                 320

Arg Leu Pro Pro Val Arg Pro Ala Leu Ala Pro Leu Val Ala Phe Val
                325                 330                 335

Ala Leu Pro Leu Pro Arg Val Glu Gly Leu Pro Asp Gly Ala Glu Ser
            340                 345                 350

Thr Asn Asp Val Pro His Asp Arg Pro Asp Met Val Glu Leu His Arg
        355                 360                 365

Arg Ala Phe Asp Gly Leu Ala Ala Pro Phe Ser Glu Phe Leu Gly Thr
    370                 375                 380

Ala Cys Ala Asp Trp Val Ile Val Asp Val Phe His His Trp Ala Ala
385                 390                 395                 400

Ala Ala Ala Leu Glu His Lys Val Pro Cys Ala Met Met Leu Leu Gly
                405                 410                 415

Ser Ala His Met Ile Ala Ser Ile Ala Asp Arg Arg Leu Glu Arg Ala
            420                 425                 430

Glu Thr Glu Ser Pro Ala Ala Gly Gln Gly Arg Pro Ala Ala Ala
        435                 440                 445

Pro Thr Phe Glu Val Ala Arg Met Lys Leu Ile Arg Thr Lys
    450                 455                 460

<210> SEQ ID NO 4
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 4
atgggtagct cgggcatgtc cctggcggaa cgcttttcgc tgacgctgag tcgctcatcc        60
ctggttgttg gtcgcagttg tgttgaattt gaaccggaaa ccgttccgct gctgtctacg       120
ctgcgcggca aaccgattac cttcctgggt ctgatgccgc cgctgcatga aggccgtcgc       180
gaagatggtg aagacgccac ggtgcgttgg ctggatgctc agccggcgaa atcggtggtt       240
tatgtcgcac tgggcagcga agtgccgctg gtgtcgaaa aagtgcacga actggccctg        300
ggcctggaac tggcaggcac ccgctttctg tgggcactgc gtaaaccgac gggcgttagc       360
gatgctgacc tgctgccggc gggttttcga aaacgcaccc cgccgccgtgg tgtcgtggcc      420 acccgttggg tgccgcaaat gtccattctg gctcatgcgg ccgttggcgc atttctgacc      480
cactgcggtt ggaacagcac gatcgaaggc ctgatgtttg tcatccgct gattatgctg       540 ccgatcttcg gcgatcaggg tccgaacgca cgcctgatcg aagccaaaaa tgcaggcctg      600
caagttgcgc gtaacgatgg cgacggtagc tttgaccgcg aaggtgtcgc agctgcgatt      660
cgtgctgtgg cggttgaaga agaaagcagc aaagtcttcc aggccaaagc gaaaaaactg    720
caagaaatcg tggctgatat ggcgtgtcat gaacgctata ttgacggctt tatccagcaa    780
ctgcgttctt acaaagatga cagtggctat agttcctcat acgccgcagc tgcgggtatg    840
catgttgtca tttgcccgtg gctggcgttt ggtcacctgc tgccgtgtct ggatctggca     900
cagcgcctgg catctcgcgg tcaccgtgtt tcgttcgtca gcaccccgcg caatatcagt    960
cgtctgccgc cggttcgtcc ggcgctggcg ccgctggttg cgttcgttgc actgccgctg   1020
ccgcgtgtgg aaggtctgcc ggatggtgcc gaatcgacca acgacgttcc gcatgatcgt   1080
ccggacatgt tcgaactgca tcgtcgcgcc tttgatggcc tggccgcacc gtttagcgaa   1140
tttctgggta cggcctgcgc agattgggtc attgtggacg tttttcacca ctgggcggcg   1200
```

```
gcggcggcgc tggaacataa agtgccgtgt gcgatgatgc tgctgggttc cgcccacatg   1260
attgcttcaa tcgcggatcg tcgcctggaa cgtgccgaaa ccgaaagtcc ggcggcggca   1320
ggccagggtc gtccggcggc ggcaccgacc tttgaagtgg cacgtatgaa actgattcgc   1380
acgaaataa                                                           1389
```

<210> SEQ ID NO 5
<211> LENGTH: 459
<212> TYPE: PRT
<213> ORGANISM: Hordeum vulgare

<400> SEQUENCE: 5

```
Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
    210                 215                 220

Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
                245                 250                 255

Glu Asp Ala Ala Val Arg Trp Leu Asp Ala Gln Pro Ala Lys Ser Val
            260                 265                 270

Val Tyr Val Ala Leu Gly Ser Glu Val Pro Leu Arg Ala Glu Gln Val
        275                 280                 285

His Glu Leu Ala Leu Gly Leu Glu Leu Ser Gly Ala Arg Phe Leu Trp
    290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
                325                 330                 335
```

```
Val Pro Gln Ile Gly Val Leu Ala His Gly Ala Val Ala Ala Phe Leu
            340                 345                 350

Thr His Cys Gly Trp Asn Ser Thr Ile Glu Gly Leu Leu Phe Gly His
            355                 360                 365

Pro Leu Ile Met Leu Pro Ile Ser Ser Asp Gln Gly Pro Asn Ala Arg
    370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Thr Val Arg Ala Val
            405                 410                 415

Ala Val Glu Glu Asp Gly Arg Arg Val Phe Thr Ala Asn Ala Lys Lys
            420                 425                 430

Met Gln Glu Ile Val Ala Asp Gly Ala Cys His Glu Arg Cys Ile Asp
            435                 440                 445

Gly Phe Ile Gln Gln Leu Arg Ser Tyr Lys Ala
    450                 455
```

<210> SEQ ID NO 6
<211> LENGTH: 1380
<212> TYPE: DNA
<213> ORGANISM: Hordeum vulgare

<400> SEQUENCE: 6

```
atggatggta actcctcctc ctcgccgctg catgtggtca tttgtccgtg gctggctctg       60
ggtcacctgc tgccgtgtct ggatattgct gaacgtctgg cgtcacgcgg ccatcgtgtc      120
agttttgtgt ccacccccgcg caacattgcc cgtctgccgc cgctgcgtcc ggctgttgca      180
ccgctggttg atttcgtcgc actgccgctg ccgcatgttg acggtctgcc ggagggtgcg      240
gaatcgacca tgatgtgcc gtatgacaaa tttgaactgc accgtaaggc gttcgatggt       300
ctggcggccc cgtttagcga atttctgcgt gcagcttgcg cagaaggtgc aggttctcgc      360
ccggattggc tgattgtgga cacctttcat cactgggcgg cggcggcggc ggtggaaaac      420
aaagtgccgt gtgttatgct gctgctgggt gcagcaacgg tgatcgctgg tttcgcgcgt      480
ggtgttagcg aacatgcggc ggcggcggtg ggtaaagaac gtccggctgc ggaagccccg      540
agttttgaaa ccgaacgtcg caagctgatg accacgcaga atgcctccgg catgaccgtg      600
gcagaacgct atttcctgac gctgatgcgt agcgatctgg ttgccatccg ctcttgcgca      660
gaatgggaac cggaaagcgt ggcagcactg accacgctgg caggtaaacc ggtggttccg      720
ctgggtctgc tgccgccgag tccggaaggc ggtcgtggcg tttccaaaga gatgctgcg      780
gtccgttggc tggacgcaca gccggcaaag tcagtcgtgt acgtcgcact gggttcggaa      840
gtgccgctgc gtgcggaaca agttcacgaa ctggcactgg gcctgaact gagcggtgct      900
cgctttctgt gggcgctgcg taaaccgacc gatgcaccgg acgccgcagt gctgccgccg      960
ggtttcgaag aacgtaccccg cggccgtggt ctggttgtca cgggttgggt gccgcagatt     1020
ggcgttctgg ctcatggtgc ggtggctgcg tttctgaccc actgtggctg gaactctacg     1080
atcgaaggcc tgctgttcgg tcatccgctg attatgctgc cgatcagctc tgatcagggt     1140
ccgaatgcgc gcctgatgga aggccgtaaa gtcggtatgc aagtgccgcg tgatgaatca     1200
gacggctcgt tcgtcgcgga agatgttgcc gcaaccgtcc gcgccgtggc agttgaagaa     1260
gacggtcgtc gcgtcttcac ggctaacgcg aaaaagatgc aagaaattgt ggccgatggc     1320
gcatgccacg aacgttgtat tgacggtttt atccagcaac tgcgcagtta caaggcgtaa     1380
```

<210> SEQ ID NO 7
<211> LENGTH: 458
<212> TYPE: PRT
<213> ORGANISM: Stevia rebaudiana

<400> SEQUENCE: 7

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380
```

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
        420                 425                 430

Lys Ala Asp Val Ser Leu Met Lys Gly Gly Ser Ser Tyr Glu Ser Leu
    435                 440                 445

Glu Ser Leu Val Ser Tyr Ile Ser Ser Leu
    450                 455

<210> SEQ ID NO 8
<211> LENGTH: 1377
<212> TYPE: DNA
<213> ORGANISM: Stevia rebaudiana

<400> SEQUENCE: 8
atggagaata agacagaaac aaccgtaaga cggaggcgga ggattatctt gttccctgta     60
ccatttcagg gccatattaa tccgatcctc aattagcaa acgtcctcta ctccaaggga    120
ttttcaataa caatcttcca tactaacttt aacaagccta aaacgagtaa ttatcctcac    180
tttacattca ggttcattct agacaacgac cctcaggatg agcgtatctc aaatttacct    240
acgcatggcc ccttggcagg tatgcgaata ccaataatca atgagcatgg agccgatgaa    300
ctccgtcgcg agttagagct tctcatgctc gcaagtgagg aagacgagga agtttcgtgc    360
ctaataactg atgcgctttg gtacttcgcc aatcagtcg cagactcact gaatctacgc    420
cgtttggtcc ttatgacaag ttcattattc aactttcacg cacatgtatc actgccgcaa    480
tttgacgagt tgggttacct ggaccccggat gacaaaacgc gattggagga caagcgtcg    540
ggcttcccca tgctgaaagt caaagatatt aagagcgctt atagtaattg gcaaattctg    600
aaagaaattc tcggaaaaat gataaagcaa accaaagcgt cctctggagt aatctggaac    660
tccttcaagg agttagagga atctgaactt gaaacggtca tcagagaaat ccccgctccc    720
tcgttcttaa ttccactacc caagcacctt actgcaagta gcagttccct cctagatcat    780
gaccgaaccg tgtttcagtg gctggatcag caaccccgt cgtcagttct atatgtaagc    840
tttgggagta cttcggaagt ggatgaaaag gacttcttag agattgcgcg agggctcgtg    900
gatagcaaac agagcttcct gtgggtagtg agaccgggat tcgttaaggg ctcgacgtgg    960
gtcgagccgt tgccagatgg ttttctaggg gagagaggga gaatcgtgaa atgggttcca   1020
cagcaagagg ttttggctca cggagctata ggggcctttt ggacccactc tggttggaat   1080
tctactcttg aaagtgtctg tgaaggcgtt ccaatgatat tttctgattt tgggcttgac   1140
cagcctctaa acgctcgcta tatgtctgat gtgttgaagg ttggcgtgta cctggagaat   1200
ggttgggaaa gggggaaat tgccaacgcc atacgccggg taatggtgga cgaggaaggt   1260
gagtacatac gtcagaacgc tcgggtttta aaacaaaaag cggacgtcag ccttatgaag   1320
ggaggtagct cctatgaatc cctagaatcc ttggtaagct atatatcttc gttataa     1377

<210> SEQ ID NO 9
<211> LENGTH: 473
<212> TYPE: PRT
<213> ORGANISM: Artificial Sequence
<220> FEATURE:
<223> OTHER INFORMATION: Synthetic Polypeptide

<400> SEQUENCE: 9

-continued

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
                20                  25                  30

Leu Ser Lys Leu Ile Ala Glu Lys Gly His Lys Val Ser Phe Leu Ser
            35                  40                  45

Thr Thr Arg Asn Ile Gln Arg Leu Ser Ser His Ile Ser Pro Leu Ile
        50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415
```

Ala Arg Ser Leu Arg Ser Val Val Glu Lys Glu Gly Glu Ile Tyr
        420                 425                 430

Lys Ala Asn Ala Arg Glu Leu Ser Lys Ile Tyr Asn Asp Thr Lys Val
            435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 10
<211> LENGTH: 1422
<212> TYPE: DNA
<213> ORGANISM: Artificial Sequence
<220> FEATURE:
<223> OTHER INFORMATION: Synthetic Polynucleotide

<400> SEQUENCE: 10

```
atggctacca gtgactccat agttgacgac cgtaagcagc ttcatgttgc gacgttccca      60
tggcttgctt tcggtcacat cctcccttac cttcagcttt cgaaattgat agctgaaaag     120
ggtcacaaag tctcgtttct ttctaccacc agaaacattc aacgtctctc ttctcatatc     180
tcgccactca taaatgttgt tcaactcaca cttccacgtg tccaagagct gccggaggat     240
gcagaggcga ccactgacgt ccaccctgaa gatattccat atctcaagaa ggcttctgat     300
ggtcttcaac cggaggtcac ccggtttcta gaacaacact ctccggactg gattatttat     360
gattatactc actactggtt gccatccatc gcggctagcc tcggtatctc acgagcccac     420
ttctccgtca ccactccatg ggccattgct tatatgggac cctcagctga cgccatgata     480
aatggttcag atggtcgaac cacggttgag gatctcacga caccgcccaa gtggtttccc     540
tttccgacca agtatgctg gcggaagcat gatcttgccc gactggtgcc ttacaaagct     600
ccggggatat ctgatggata ccgtatgggg atggttctta agggatctga ttgtttgctt     660
tccaaatgtt accatgagtt tggaactcaa tggctacctc ttttggagac actacaccaa     720
gtaccggtgg ttccggtggg attactgcca ccggaaatac ccggagacga aaagatgaa      780
acatgggtgt caatcaagaa atggctcgat ggtaaacaaa aaggcagtgt ggtgtacgtt     840
gcattaggaa gcgaggcttt ggtgagccaa accgaggttg ttgagttagc attgggtctc     900
gagctttctg ggttgccatt tgtttgggct tatagaaaac caaaaggtcc cgcgaagtca     960
gactcggtgg agttgccaga cgggttcgtg aacgaactcg tgaccgtgg ttggtctgg     1020
acgagttggg cacctcagtt acgaatactg agccatgagt cggtttgtgg tttcttgact    1080
cattgtggtt ctggatcaat tgtggaaggg ctaatgtttg gtcaccctct aatcatgcta    1140
ccgattttg gggaccaacc tctgaatgct cgattactgg aggacaaaca ggtgggaatc    1200
gagataccaa gaaatgagga agatggttgc ttgaccaagg agtcggttgc tagatcactg    1260
aggtccgttg ttgtggaaaa agaaggggag atctacaagg cgaacgcgag ggagctgagt    1320
aaaatctata cgacactaa ggttgaaaaa gaatatgtaa gccaattcgt agactatttg    1380
gaaaagaatg cgcgtgcggt tgccatcgat catgagagtt aa                       1422
```

<210> SEQ ID NO 11
<211> LENGTH: 458
<212> TYPE: PRT
<213> ORGANISM: Artificial Sequence
<220> FEATURE:
<223> OTHER INFORMATION: Synthetic Polypeptide

<400> SEQUENCE: 11

-continued

```
Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu
            20                  25                  30

Glu Ser Glu Leu Glu Thr Val Ile Arg Glu Ile Pro Ala Pro Ser Phe
        35                  40                  45

Leu Ile Pro Leu Pro Lys His Leu Thr Ala Ser Ser Ser Ser Leu Leu
    50                  55                  60

Asp His Asp Arg Thr Val Phe Gln Trp Leu Asp Gln Gln Pro Pro Ser
65                  70                  75                  80

Ser Val Leu Tyr Val Ser Phe Gly Ser Thr Ser Glu Val Asp Glu Lys
                85                  90                  95

Asp Phe Leu Glu Ile Ala Arg Gly Leu Val Asp Ser Lys Gln Ser Phe
            100                 105                 110

Leu Trp Val Val Arg Pro Gly Phe Val Lys Gly Ser Thr Trp Val Glu
        115                 120                 125

Pro Leu Pro Asp Gly Phe Leu Gly Glu Arg Gly Arg Ile Val Lys Trp
    130                 135                 140

Val Pro Gln Gln Glu Val Leu Ala His Gly Ala Ile Gly Ala Phe Trp
145                 150                 155                 160

Thr His Ser Gly Trp Asn Ser Thr Leu Glu Ser Val Cys Glu Gly Val
                165                 170                 175

Pro Met Ile Phe Ser Asp Phe Gly Leu Asp Gln Pro Leu Asn Ala Arg
            180                 185                 190

Tyr Met Ser Asp Val Leu Lys Val Gly Val Tyr Leu Glu Asn Gly Trp
        195                 200                 205

Glu Arg Gly Glu Ile Ala Asn Ala Ile Arg Arg Val Met Val Asp Glu
    210                 215                 220

Glu Gly Glu Tyr Ile Arg Gln Asn Ala Arg Val Leu Lys Gln Lys Ala
225                 230                 235                 240

Asp Val Ser Leu Met Lys Gly Gly Ser Ser Tyr Glu Ser Leu Glu Ser
                245                 250                 255

Leu Val Ser Tyr Ile Ser Ser Leu Glu Asn Lys Thr Glu Thr Thr Val
            260                 265                 270

Arg Arg Arg Arg Arg Ile Ile Leu Phe Pro Val Pro Phe Gln Gly His
        275                 280                 285

Ile Asn Pro Ile Leu Gln Leu Ala Asn Val Leu Tyr Ser Lys Gly Phe
    290                 295                 300

Ser Ile Thr Ile Phe His Thr Asn Phe Asn Lys Pro Lys Thr Ser Asn
305                 310                 315                 320

Tyr Pro His Phe Thr Phe Arg Phe Ile Leu Asp Asn Asp Pro Gln Asp
                325                 330                 335

Glu Arg Ile Ser Asn Leu Pro Thr His Gly Pro Leu Ala Gly Met Arg
            340                 345                 350

Ile Pro Ile Ile Asn Glu His Gly Ala Asp Glu Leu Arg Arg Glu Leu
        355                 360                 365

Glu Leu Leu Met Leu Ala Ser Glu Glu Asp Glu Glu Val Ser Cys Leu
    370                 375                 380

Ile Thr Asp Ala Leu Trp Tyr Phe Ala Gln Ser Val Ala Asp Ser Leu
385                 390                 395                 400

Asn Leu Arg Arg Leu Val Leu Met Thr Ser Ser Leu Phe Asn Phe His
                405                 410                 415
```

Ala His Val Ser Leu Pro Gln Phe Asp Glu Leu Gly Tyr Leu Asp Pro
            420                 425                 430

Asp Asp Lys Thr Arg Leu Glu Glu Gln Ala Ser Gly Phe Pro Met Leu
        435                 440                 445

Lys Val Lys Asp Ile Lys Ser Ala Tyr Ser
    450                 455

<210> SEQ ID NO 12
<211> LENGTH: 1377
<212> TYPE: DNA
<213> ORGANISM: Artificial Sequence
<220> FEATURE:
<223> OTHER INFORMATION: Synthetic Polynucleotide

<400> SEQUENCE: 12

| | | |
|---|---|---|
| atgaactggc aaatcctgaa agaaatcctg ggtaaaatga tcaaacaaac caaagcgtcg | 60 |
| tcgggcgtta tctggaactc cttcaaagaa ctggaagaat cagaactgga aaccgttatt | 120 |
| cgcgaaatcc cggctccgtc gttcctgatt ccgctgccga acatctgac cgcgagcagc | 180 |
| agcagcctgc tggatcacga ccgtacggtc tttcagtggc tggatcagca accgccgtca | 240 |
| tcggtgctgt atgtttcatt cggtagcacc tctgaagtcg atgaaaaaga ctttctggaa | 300 |
| atcgctcgcg cctggtgga tagtaaacag tccttcctgt gggtggttcg tccgggtttt | 360 |
| gtgaaaggca gcacgtgggt tgaaccgctg ccggatggct tcctgggtga cgcggccgt | 420 |
| attgtcaaat gggtgccgca gcaagaagtg ctggcacatg tgctatcgg cgcgttttgg | 480 |
| acccactctg gttggaacag tacgctggaa tccgtttgcg aaggtgtccc gatgattttc | 540 |
| agcgattttg gcctggacca ccgctgaat gcccgctata tgtctgatgt tctgaaagtc | 600 |
| ggtgtgtacc tggaaaacgg ttgggaacgt ggcgaaattg cgaatgccat ccgtcgcgtt | 660 |
| atggtcgatg aagaaggcga atacattcgc cagaacgctc gtgtcctgaa acaaaaagcg | 720 |
| gacgtgagcc tgatgaaagg cggtagctct tatgaatcac tggaatcgct ggttagctac | 780 |
| atcagttccc tggaaaataa aaccgaaacc acggtgcgtc gccgtcgccg tattatcctg | 840 |
| ttcccggttc cgtttcaggg tcatattaac ccgatcctgc aactggcgaa tgttctgtat | 900 |
| tcaaaaggct tttcgatcac catcttccat acgaacttca caaaccgaa aaccagtaac | 960 |
| tacccgcact ttacgttccg ctttattctg gataacgacc cgcaggatga acgtatctcc | 1020 |
| aatctgccga cccacggccc gctggccggt atgcgcattc cgattatcaa tgaacacggt | 1080 |
| gcagatgaac tgcgccgtga actggaactg ctgatgctgg ccagtgaaga agatgaagaa | 1140 |
| gtgtcctgtc tgatcaccga cgcactgtgg tatttcgccc agagcgttgc agattctctg | 1200 |
| aacctgcgcc gtctggtcct gatgacgtca tcgctgttca attttcatgc gcacgtttct | 1260 |
| ctgccgcaat tgatgaact gggctacctg gacccggatg acaaaacccg tctggaagaa | 1320 |
| caagccagtg gttttccgat gctgaaagtc aaagacatta atccgccta ttcgtaa | 1377 |

<210> SEQ ID NO 13
<211> LENGTH: 475
<212> TYPE: PRT
<213> ORGANISM: Artificial Sequence
<220> FEATURE:
<223> OTHER INFORMATION: Synthetic Polypeptide

<400> SEQUENCE: 13

Met Asn Trp Gln Ile Leu Lys Glu Ile Leu Gly Lys Met Ile Lys Gln
1               5                   10                  15

Thr Lys Ala Ser Ser Gly Val Ile Trp Asn Ser Phe Lys Glu Leu Glu

-continued

```
               20                  25                  30
Glu Ser Glu Leu Glu Thr Val Ile Arg Glu Ile Pro Ala Pro Ser Phe
             35                  40                  45
Leu Ile Pro Leu Pro Lys His Leu Thr Ala Ser Ser Ser Leu Leu
         50                  55                  60
Asp His Asp Arg Thr Val Phe Gln Trp Leu Asp Gln Pro Pro Ser
 65                  70                  75                  80
Ser Val Leu Tyr Val Ser Phe Gly Ser Thr Ser Glu Val Asp Glu Lys
                 85                  90                  95
Asp Phe Leu Glu Ile Ala Arg Gly Leu Val Asp Ser Lys Gln Ser Phe
             100                 105                 110
Leu Trp Val Val Arg Pro Gly Phe Val Lys Gly Ser Thr Trp Val Glu
             115                 120                 125
Pro Leu Pro Asp Gly Phe Leu Gly Glu Arg Gly Arg Ile Val Lys Trp
             130                 135                 140
Val Pro Gln Gln Glu Val Leu Ala His Gly Ala Ile Gly Ala Phe Trp
145                 150                 155                 160
Thr His Ser Gly Trp Asn Ser Thr Leu Glu Ser Val Cys Glu Gly Val
                 165                 170                 175
Pro Met Ile Phe Ser Asp Phe Gly Leu Asp Gln Pro Leu Asn Ala Arg
             180                 185                 190
Tyr Met Ser Asp Val Leu Lys Val Gly Val Tyr Leu Glu Asn Gly Trp
             195                 200                 205
Glu Arg Gly Glu Ile Ala Asn Ala Ile Arg Arg Val Met Val Asp Glu
             210                 215                 220
Glu Gly Glu Tyr Ile Arg Gln Asn Ala Arg Val Leu Lys Gln Lys Ala
225                 230                 235                 240
Asp Val Ser Leu Met Lys Gly Gly Ser Ser Tyr Glu Ser Leu Glu Ser
                 245                 250                 255
Leu Val Ser Tyr Ile Ser Ser Leu Tyr Lys Asp Asp Ser Gly Tyr Ser
             260                 265                 270
Ser Ser Tyr Ala Ala Ala Ala Gly Met Glu Asn Lys Thr Glu Thr Thr
         275                 280                 285
Val Arg Arg Arg Arg Ile Ile Leu Phe Pro Val Pro Phe Gln Gly
             290                 295                 300
His Ile Asn Pro Ile Leu Gln Leu Ala Asn Val Leu Tyr Ser Lys Gly
305                 310                 315                 320
Phe Ser Ile Thr Ile Phe His Thr Asn Phe Asn Lys Pro Lys Thr Ser
                 325                 330                 335
Asn Tyr Pro His Phe Thr Phe Arg Phe Ile Leu Asp Asn Asp Pro Gln
             340                 345                 350
Asp Glu Arg Ile Ser Asn Leu Pro Thr His Gly Pro Leu Ala Gly Met
             355                 360                 365
Arg Ile Pro Ile Ile Asn Glu His Gly Ala Asp Glu Leu Arg Arg Glu
             370                 375                 380
Leu Glu Leu Leu Met Leu Ala Ser Glu Glu Asp Glu Val Ser Cys
385                 390                 395                 400
Leu Ile Thr Asp Ala Leu Trp Tyr Phe Ala Gln Ser Val Ala Asp Ser
                 405                 410                 415
Leu Asn Leu Arg Arg Leu Val Leu Met Thr Ser Ser Leu Phe Asn Phe
             420                 425                 430
His Ala His Val Ser Leu Pro Gln Phe Asp Glu Leu Gly Tyr Leu Asp
             435                 440                 445
```

Pro Asp Asp Lys Thr Arg Leu Glu Glu Gln Ala Ser Gly Phe Pro Met
    450                 455                 460

Leu Lys Val Lys Asp Ile Lys Ser Ala Tyr Ser
465                 470                 475

<210> SEQ ID NO 14
<211> LENGTH: 1428
<212> TYPE: DNA
<213> ORGANISM: Artificial Sequence
<220> FEATURE:
<223> OTHER INFORMATION: Synthetic Polynucleotide

<400> SEQUENCE: 14

```
atgaactggc aaatcctgaa agaaatcctg ggtaaaatga tcaaacaaac caaagcgtcg    60
tcgggcgtta tctggaactc cttcaaagaa ctggaagaat cagaactgga aaccgttatt   120
cgcgaaatcc cggctccgtc gttcctgatt ccgctgccga acatctgac cgcgagcagc    180
agcagcctgc tggatcacga ccgtacggtc tttcagtggc tggatcagca accgccgtca   240
tcggtgctgt atgtttcatt cggtagcacc tctgaagtcg atgaaaaaga ctttctggaa   300
atcgctcgcg gcctggtgga tagtaaacag tccttcctgt gggtggttcg tccgggtttt   360
gtgaaaggca gcacgtgggt tgaaccgctg ccggatggct tcctgggtga acgcggccgt   420
attgtcaaat gggtgccgca gcaagaagtg ctggcacatg gtgctatcgg cgcgttttgg   480
acccactctg gttggaacag tacgctggaa tccgtttgcg aaggtgtccc gatgattttc   540
agcgattttg cctggaccaa ccgctgaat gccgctata tgtctgatgt tctgaaagtc   600
ggtgtgtacc tggaaaacgg ttgggaacgt ggcgaaattg cgaatgccat ccgtcgcgtt   660
atggtcgatg aagaaggcga atacattcgc cagaacgctc gtgtcctgaa acaaaaagcg   720
gacgtgagcc tgatgaaagg cggtagctct tatgaatcac tggaatcgct ggttagctac   780
atcagttccc tgtacaaaga tgacagcggt tatagcagca gctatgcggc ggcggcgggt   840
atggaaaata aaccgaaac cacggtgcgt cgccgtcgcc gtattatcct gttcccggtt   900
ccgtttcagg gtcatattaa cccgatcctg caactggcga atgttctgta ttcaaaaggc   960
ttttcgatca ccatcttcca tacgaacttc aacaaaccga aaccagtaa ctacccgcac  1020
tttacgttcc gctttattct ggataacgac ccgcaggatg aacgtatctc caatctgccg  1080
acccacggcc cgctggccgg tatgcgcatt ccgattatca tgaacacgg tgcagatgaa  1140
ctgcgccgtg aactggaact gctgatgctg gccagtgaag aagatgaaga agtgtcctgt  1200
ctgatcaccg acgcactgtg gtatttcgcc cagagcgttg cagattctct gaacctgcgc  1260
cgtctggtcc tgatgacgtc atcgctgttc aattttcatg cgcacgtttc tctgccgcaa  1320
tttgatgaac tgggctacct ggacccggat gacaaaaccc gtctggaaga acaagccagt  1380
ggttttccga tgctgaaagt caaagacatt aaatccgcct attcgtaa              1428
```

<210> SEQ ID NO 15
<211> LENGTH: 1268
<212> TYPE: PRT
<213> ORGANISM: Artificial Sequence
<220> FEATURE:
<223> OTHER INFORMATION: Synthetic Polypeptide

<400> SEQUENCE: 15

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu

-continued

```
                20                  25                  30
Ala Asn Val Leu Tyr Ser Lys Gly Phe Ser Ile Thr Ile Phe His Thr
                35                  40                  45
Asn Phe Asn Lys Pro Lys Thr Ser Asn Tyr Pro His Phe Thr Phe Arg
 50                  55                  60
Phe Ile Leu Asp Asn Asp Pro Gln Asp Glu Arg Ile Ser Asn Leu Pro
 65                  70                  75                  80
Thr His Gly Pro Leu Ala Gly Met Arg Ile Pro Ile Ile Asn Glu His
                 85                  90                  95
Gly Ala Asp Glu Leu Arg Arg Glu Leu Glu Leu Leu Met Leu Ala Ser
                100                 105                 110
Glu Glu Asp Glu Glu Val Ser Cys Leu Ile Thr Asp Ala Leu Trp Tyr
                115                 120                 125
Phe Ala Gln Ser Val Ala Asp Ser Leu Asn Leu Arg Arg Leu Val Leu
                130                 135                 140
Met Thr Ser Ser Leu Phe Asn Phe His Ala His Val Ser Leu Pro Gln
145                 150                 155                 160
Phe Asp Glu Leu Gly Tyr Leu Asp Pro Asp Asp Lys Thr Arg Leu Glu
                165                 170                 175
Glu Gln Ala Ser Gly Phe Pro Met Leu Lys Val Lys Asp Ile Lys Ser
                180                 185                 190
Ala Tyr Ser Asn Trp Gln Ile Leu Lys Glu Ile Leu Gly Lys Met Ile
                195                 200                 205
Lys Gln Thr Lys Ala Ser Ser Gly Val Ile Trp Asn Ser Phe Lys Glu
                210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
                245                 250                 255
Leu Leu Asp His Asp Arg Thr Val Phe Gln Trp Leu Asp Gln Gln Pro
                260                 265                 270
Pro Ser Ser Val Leu Tyr Val Ser Phe Gly Ser Thr Ser Glu Val Asp
                275                 280                 285
Glu Lys Asp Phe Leu Glu Ile Ala Arg Gly Leu Val Asp Ser Lys Gln
                290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                325                 330                 335
Lys Trp Val Pro Gln Gln Glu Val Leu Ala His Gly Ala Ile Gly Ala
                340                 345                 350
Phe Trp Thr His Ser Gly Trp Asn Ser Thr Leu Glu Ser Val Cys Glu
                355                 360                 365
Gly Val Pro Met Ile Phe Ser Asp Phe Gly Leu Asp Gln Pro Leu Asn
                370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                405                 410                 415
Asp Glu Glu Gly Glu Tyr Ile Arg Gln Asn Ala Arg Val Leu Lys Gln
                420                 425                 430
Lys Ala Asp Val Ser Leu Met Lys Gly Gly Ser Ser Tyr Glu Ser Leu
                435                 440                 445
```

-continued

```
Glu Ser Leu Val Ser Tyr Ile Ser Ser Leu Gly Ser Gly Ala Asn Ala
    450                 455                 460
Glu Arg Met Ile Thr Arg Val His Ser Gln Arg Glu Arg Leu Asn Glu
465                 470                 475                 480
Thr Leu Val Ser Glu Arg Asn Glu Val Leu Ala Leu Leu Ser Arg Val
                485                 490                 495
Glu Ala Lys Gly Lys Gly Ile Leu Gln Gln Asn Gln Ile Ile Ala Glu
            500                 505                 510
Phe Glu Ala Leu Pro Glu Gln Thr Arg Lys Lys Leu Glu Gly Gly Pro
        515                 520                 525
Phe Phe Asp Leu Leu Lys Ser Thr Gln Glu Ala Ile Val Leu Pro Pro
    530                 535                 540
Trp Val Ala Leu Ala Val Arg Pro Arg Pro Gly Val Trp Glu Tyr Leu
545                 550                 555                 560
Arg Val Asn Leu His Ala Leu Val Val Glu Glu Leu Gln Pro Ala Glu
                565                 570                 575
Phe Leu His Phe Lys Glu Leu Val Asp Gly Val Lys Asn Gly Asn
            580                 585                 590
Phe Thr Leu Glu Leu Asp Phe Glu Pro Phe Asn Ala Ser Ile Pro Arg
        595                 600                 605
Pro Thr Leu His Lys Tyr Ile Gly Asn Gly Val Asp Phe Leu Asn Arg
    610                 615                 620
His Leu Ser Ala Lys Leu Phe His Asp Lys Glu Ser Leu Leu Pro Leu
625                 630                 635                 640
Leu Lys Phe Leu Arg Leu His Ser His Gln Gly Lys Asn Leu Met Leu
                645                 650                 655
Ser Glu Lys Ile Gln Asn Leu Asn Thr Leu Gln His Thr Leu Arg Lys
            660                 665                 670
Ala Glu Glu Tyr Leu Ala Glu Leu Lys Ser Glu Thr Leu Tyr Glu Glu
        675                 680                 685
Phe Glu Ala Lys Phe Glu Glu Ile Gly Leu Glu Arg Gly Trp Gly Asp
    690                 695                 700
Asn Ala Glu Arg Val Leu Asp Met Ile Arg Leu Leu Leu Asp Leu Leu
705                 710                 715                 720
Glu Ala Pro Asp Pro Cys Thr Leu Glu Thr Phe Leu Gly Arg Val Pro
                725                 730                 735
Met Val Phe Asn Val Val Ile Leu Ser Pro His Gly Tyr Phe Ala Gln
            740                 745                 750
Asp Asn Val Leu Gly Tyr Pro Asp Thr Gly Gly Gln Val Val Tyr Ile
        755                 760                 765
Leu Asp Gln Val Arg Ala Leu Glu Ile Glu Met Leu Gln Arg Ile Lys
    770                 775                 780
Gln Gln Gly Leu Asn Ile Lys Pro Arg Ile Leu Ile Leu Thr Arg Leu
785                 790                 795                 800
Leu Pro Asp Ala Val Gly Thr Thr Cys Gly Glu Arg Leu Glu Arg Val
                805                 810                 815
Tyr Asp Ser Glu Tyr Cys Asp Ile Leu Arg Val Pro Phe Arg Thr Glu
            820                 825                 830
Lys Gly Ile Val Arg Lys Trp Ile Ser Arg Phe Glu Val Trp Pro Tyr
        835                 840                 845
Leu Glu Thr Tyr Thr Glu Asp Ala Ala Val Glu Leu Ser Lys Glu Leu
    850                 855                 860
```

-continued

Asn Gly Lys Pro Asp Leu Ile Ile Gly Asn Tyr Ser Asp Gly Asn Leu
865             870             875             880

Val Ala Ser Leu Leu Ala His Lys Leu Gly Val Thr Gln Cys Thr Ile
            885             890             895

Ala His Ala Leu Glu Lys Thr Lys Tyr Pro Asp Ser Asp Ile Tyr Trp
        900             905             910

Lys Lys Leu Asp Asp Lys Tyr His Phe Ser Cys Gln Phe Thr Ala Asp
        915             920             925

Ile Phe Ala Met Asn His Thr Asp Phe Ile Ile Thr Ser Thr Phe Gln
    930             935             940

Glu Ile Ala Gly Ser Lys Glu Thr Val Gly Gln Tyr Glu Ser His Thr
945             950             955             960

Ala Phe Thr Leu Pro Gly Leu Tyr Arg Val Val His Gly Ile Asp Val
            965             970             975

Phe Asp Pro Lys Phe Asn Ile Val Ser Pro Gly Ala Asp Met Ser Ile
        980             985             990

Tyr Phe Pro Tyr Thr Glu Glu Lys Arg Arg Leu Thr Lys Phe His Ser
        995             1000            1005

Glu Ile Glu Glu Leu Leu Tyr Ser Asp Val Glu Asn Lys Glu His
    1010            1015            1020

Leu Cys Val Leu Lys Asp Lys Lys Lys Pro Ile Leu Phe Thr Met
    1025            1030            1035

Ala Arg Leu Asp Arg Val Lys Asn Leu Ser Gly Leu Val Glu Trp
    1040            1045            1050

Tyr Gly Lys Asn Thr Arg Leu Arg Glu Leu Ala Asn Leu Val Val
    1055            1060            1065

Val Gly Gly Asp Arg Arg Lys Glu Ser Lys Asp Asn Glu Glu Lys
    1070            1075            1080

Ala Glu Met Lys Lys Met Tyr Asp Leu Ile Glu Glu Tyr Lys Leu
    1085            1090            1095

Asn Gly Gln Phe Arg Trp Ile Ser Ser Gln Met Asp Arg Val Arg
    1100            1105            1110

Asn Gly Glu Leu Tyr Arg Tyr Ile Cys Asp Thr Lys Gly Ala Phe
    1115            1120            1125

Val Gln Pro Ala Leu Tyr Glu Ala Phe Gly Leu Thr Val Val Glu
    1130            1135            1140

Ala Met Thr Cys Gly Leu Pro Thr Phe Ala Thr Cys Lys Gly Gly
    1145            1150            1155

Pro Ala Glu Ile Ile Val His Gly Lys Ser Gly Phe His Ile Asp
    1160            1165            1170

Pro Tyr His Gly Asp Gln Ala Ala Asp Thr Leu Ala Asp Phe Phe
    1175            1180            1185

Thr Lys Cys Lys Glu Asp Pro Ser His Trp Asp Glu Ile Ser Lys
    1190            1195            1200

Gly Gly Leu Gln Arg Ile Glu Glu Lys Tyr Thr Trp Gln Ile Tyr
    1205            1210            1215

Ser Gln Arg Leu Leu Thr Leu Thr Gly Val Tyr Gly Phe Trp Lys
    1220            1225            1230

His Val Ser Asn Leu Asp Arg Leu Glu Ala Arg Arg Tyr Leu Glu
    1235            1240            1245

Met Phe Tyr Ala Leu Lys Tyr Arg Pro Leu Ala Gln Ala Val Pro
    1250            1255            1260

Leu Ala Gln Asp Asp

1265

<210> SEQ ID NO 16
<211> LENGTH: 3807
<212> TYPE: DNA
<213> ORGANISM: Artificial Sequence
<220> FEATURE:
<223> OTHER INFORMATION: Synthetic Polynucleotide

<400> SEQUENCE: 16

| | | | | | |
|---|---|---|---|---|---|
| atggagaata | agacagaaac | aaccgtaaga | cggaggcgga | ggattatctt | gttccctgta | 60 |
| ccatttcagg | gccatattaa | tccgatcctc | caattagcaa | acgtcctcta | ctccaaggga | 120 |
| ttttcaataa | caatcttcca | tactaacttt | aacaagccta | aacgagtaa | ttatcctcac | 180 |
| tttacattca | ggttcattct | agacaacgac | cctcaggatg | agcgtatctc | aaatttacct | 240 |
| acgcatggcc | ccttggcagg | tatgcgaata | ccaataatca | atgagcatgg | agccgatgaa | 300 |
| ctccgtcgcg | agtagagct | tctcatgctc | gcaagtgagg | aagacgagga | agtttcgtgc | 360 |
| ctaataactg | atgcgctttg | gtacttcgcc | caatcagtcg | cagactcact | gaatctacgc | 420 |
| cgtttggtcc | ttatgacaag | ttcattattc | aactttcacg | cacatgtatc | actgccgcaa | 480 |
| tttgacgagt | tgggttacct | ggacccggat | gacaaaacgc | gattggagga | caagcgtcg | 540 |
| ggcttcccca | tgctgaaagt | caaagatatt | aagagcgctt | atagtaattg | gcaaattctg | 600 |
| aaagaaattc | tcggaaaaat | gataaagcaa | accaaagcgt | cctctggagt | aatctggaac | 660 |
| tccttcaagg | agttagagga | atctgaactt | gaaacggtca | tcagagaaat | ccccgctccc | 720 |
| tcgttcttaa | ttccactacc | caagcacctt | actgcaagta | gcagttccct | cctagatcat | 780 |
| gaccgaaccg | tgtttcagtg | gctggatcag | caacccccgt | cgtcagttct | atatgtaagc | 840 |
| tttggggta | cttcggaagt | ggatgaaaag | gacttcttag | agattgcgcg | agggctcgtg | 900 |
| gatagcaaac | agagcttcct | gtgggtagtg | agaccgggat | tcgttaaggg | ctcgacgtgg | 960 |
| gtcgagccgt | tgccagatgg | ttttctaggg | gagagaggga | gaatcgtgaa | atgggttcca | 1020 |
| cagcaagagg | ttttggctca | cggagctata | ggggcttttt | ggacccactc | tggttggaat | 1080 |
| tctactcttg | aaagtgtctg | tgaaggcgtt | ccaatgatat | tttctgattt | tgggcttgac | 1140 |
| cagcctctaa | acgctcgcta | tatgtctgat | gtgttgaagg | ttggcgtgta | cctggagaat | 1200 |
| ggttgggaaa | gggggaaat | tgccaacgcc | atacgccggg | taatggtgga | cgaggaaggt | 1260 |
| gagtacatac | gtcagaacgc | tcgggtttta | aaacaaaaag | cggacgtcag | ccttatgaag | 1320 |
| ggaggtagct | cctatgaatc | cctagaatcc | ttggtaagct | atatatcttc | gttaggttct | 1380 |
| ggtgcaaacg | ctgaacgtat | gataacgcgc | gtccacagcc | aacgtgagcg | tttgaacgaa | 1440 |
| acgcttgttt | ctgagagaaa | cgaagtcctt | gccttgcttt | ccaggggttga | agccaaaggt | 1500 |
| aaaggtattt | tacaacaaaa | ccagatcatt | gctgaattcg | aagctttgcc | tgaacaaacc | 1560 |
| cggaagaaac | ttgaaggtgg | tccttttcttt | gaccttctca | aatccactca | ggaagcaatt | 1620 |
| gtgttgccac | catgggttgc | tctagctgtg | aggccaaggc | ctggtgtttg | gaatactta | 1680 |
| cgagtcaatc | tccatgctct | tgtcgttgaa | gaactccaac | ctgctgagtt | tcttcatttc | 1740 |
| aaggaagaac | tcgttgatgg | agttaagaat | ggtaatttca | ctcttgagct | tgatttcgag | 1800 |
| ccattcaatg | cgtctatccc | tcgtccaaca | ctccacaaat | acattggaaa | tggtgttgac | 1860 |
| ttccttaacc | gtcatttatc | ggctaagctc | ttccatgaca | aggagagttt | gcttccattg | 1920 |
| cttaagttcc | ttcgtcttca | cagccaccag | ggcaagaacc | tgatgttgag | cgagaagatt | 1980 |
| cagaacctca | acactctgca | acacaccttg | aggaaagcag | aagagtatct | agcagagctt | 2040 |

-continued

```
aagtccgaaa cactgtatga agagtttgag gccaagtttg aggagattgg tcttgagagg   2100
ggatggggag acaatgcaga gcgtgtcctt gacatgatac gtcttctttt ggaccttctt   2160
gaggcgcctg atccttgcac tcttgagact tttcttggaa gagtaccaat ggtgttcaac   2220
gttgtgatcc tctctccaca tggttacttt gctcaggaca atgttcttgg ttaccctgac   2280
actggtggac aggttgttta cattcttgat caagttcgtg ctctggagat agagatgctt   2340
caacgtatta gcaacaagg actcaacatt aaaccaagga ttctcattct aactcgactt   2400
ctacctgatg cggtaggaac tacatgcggt gaacgtctcg agagagttta tgattctgag   2460
tactgtgata ttcttcgtgt gcccttcaga acagagaagg gtattgttcg caaatggatc   2520
tcaaggttcg aagtctggcc atatctagag acttacaccg aggatgctgc ggttgagcta   2580
tcgaaagaat tgaatggcaa gcctgacctt atcattggta actacagtga tggaaatctt   2640
gttgcttctt tattggctca caaacttggt gtcactcagt gtaccattgc tcatgctctt   2700
gagaaaacaa gtacccggga ttctgatatc tactggaaga agcttgacga caagtaccat   2760
ttctcatgcc agttcactgc ggatattttc gcaatgaacc acactgattt catcatcact   2820
agtacttttcc aagaaattgc tggaagcaaa gaaactgttg ggcagtatga agccacaca   2880
gcctttactc ttcccggatt gtatcgagtt gttcacggga ttgatgtgtt tgatcccaag   2940
ttcaacattg tctctcctgg tgctgatatg agcatctact tcccttacac agaggagaag   3000
cgtagattga ctaagttcca ctctgagatc gaggagctcc tctacagcga tgttgagaac   3060
aaagagcact tatgtgtgct caaggacaag aagaagccga ttctcttcac aatggctagg   3120
cttgatcgtg tcaagaactt gtcaggtctt gttgagtggt acgggaagaa cacccgcttg   3180
cgtgagctag ctaacttggt tgttgttgga ggagacagga ggaaagagtc aaaggacaat   3240
gaagagaaag cagagatgaa gaaaatgtat gatctcattg aggaatacaa gctaaacggt   3300
cagttcaggt ggatctcctc tcagatggac cgggtaagga acggtgagct gtaccggtac   3360
atctgtgaca ccaagggtgc ttttgtccaa cctgcattat atgaagcctt tgggttaact   3420
gttgtggagg ctatgacttg tggtttaccg actttcgcca cttgcaaagg tggtccagct   3480
gagatcattg tgcacggtaa atcgggtttc cacattgacc cttaccatgg tgatcaggct   3540
gctgatactc ttgctgattt cttcaccaag tgtaaggagg atccatctca ctgggatgag   3600
atctcaaaag gagggcttca gaggattgag gagaaataca cttggcaaat ctattcacag   3660
aggctcttga cattgactgg tgtgtatgga ttctggaagc atgtctcgaa ccttgaccgt   3720
cttgaggctc gccgttacct tgaaatgttc tatgcattga agtatcgccc attggctcag   3780
gctgttcctc ttgcacaaga tgattga                                       3807
```

<210> SEQ ID NO 17
<211> LENGTH: 808
<212> TYPE: PRT
<213> ORGANISM: Arabiodopsis thaliana

<400> SEQUENCE: 17

Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
                20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu

-continued

```
                50                  55                  60
Glu Gly Gly Pro Phe Phe Asp Leu Leu Lys Ser Thr Gln Glu Ala Ile
 65                  70                  75                  80

Val Leu Pro Pro Trp Val Ala Leu Ala Val Arg Pro Arg Pro Gly Val
                 85                  90                  95

Trp Glu Tyr Leu Arg Val Asn Leu His Ala Leu Val Glu Glu Leu
                100                 105                 110

Gln Pro Ala Glu Phe Leu His Phe Lys Glu Leu Val Asp Gly Val
                115                 120                 125

Lys Asn Gly Asn Phe Thr Leu Glu Leu Asp Phe Glu Pro Phe Asn Ala
130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
                180                 185                 190

Asn Leu Met Leu Ser Glu Lys Ile Gln Asn Leu Asn Thr Leu Gln His
                195                 200                 205

Thr Leu Arg Lys Ala Glu Glu Tyr Leu Ala Glu Leu Lys Ser Glu Thr
210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
                245                 250                 255

Leu Asp Leu Leu Glu Ala Pro Asp Pro Cys Thr Leu Glu Thr Phe Leu
                260                 265                 270

Gly Arg Val Pro Met Val Phe Asn Val Val Ile Leu Ser Pro His Gly
                275                 280                 285

Tyr Phe Ala Gln Asp Asn Val Leu Gly Tyr Pro Asp Thr Gly Gly Gln
                290                 295                 300

Val Val Tyr Ile Leu Asp Gln Val Arg Ala Leu Glu Ile Glu Met Leu
305                 310                 315                 320

Gln Arg Ile Lys Gln Gln Gly Leu Asn Ile Lys Pro Arg Ile Leu Ile
                325                 330                 335

Leu Thr Arg Leu Leu Pro Asp Ala Val Gly Thr Thr Cys Gly Glu Arg
                340                 345                 350

Leu Glu Arg Val Tyr Asp Ser Glu Tyr Cys Asp Ile Leu Arg Val Pro
                355                 360                 365

Phe Arg Thr Glu Lys Gly Ile Val Arg Lys Trp Ile Ser Arg Phe Glu
370                 375                 380

Val Trp Pro Tyr Leu Glu Thr Tyr Thr Glu Asp Ala Ala Val Glu Leu
385                 390                 395                 400

Ser Lys Glu Leu Asn Gly Lys Pro Asp Leu Ile Ile Gly Asn Tyr Ser
                405                 410                 415

Asp Gly Asn Leu Val Ala Ser Leu Leu Ala His Lys Leu Gly Val Thr
                420                 425                 430

Gln Cys Thr Ile Ala His Ala Leu Glu Lys Thr Lys Tyr Pro Asp Ser
                435                 440                 445

Asp Ile Tyr Trp Lys Lys Leu Asp Asp Lys Tyr His Phe Ser Cys Gln
                450                 455                 460

Phe Thr Ala Asp Ile Phe Ala Met Asn His Thr Asp Phe Ile Ile Thr
465                 470                 475                 480
```

```
Ser Thr Phe Gln Glu Ile Ala Gly Ser Lys Glu Thr Val Gly Gln Tyr
            485                 490                 495

Glu Ser His Thr Ala Phe Thr Leu Pro Gly Leu Tyr Arg Val Val His
        500                 505                 510

Gly Ile Asp Val Phe Asp Pro Lys Phe Asn Ile Val Ser Pro Gly Ala
        515                 520                 525

Asp Met Ser Ile Tyr Phe Pro Tyr Thr Glu Lys Arg Arg Leu Thr
    530                 535                 540

Lys Phe His Ser Glu Ile Glu Glu Leu Leu Tyr Ser Asp Val Glu Asn
545                 550                 555                 560

Lys Glu His Leu Cys Val Leu Lys Asp Lys Lys Pro Ile Leu Phe
                565                 570                 575

Thr Met Ala Arg Leu Asp Arg Val Lys Asn Leu Ser Gly Leu Val Glu
                580                 585                 590

Trp Tyr Gly Lys Asn Thr Arg Leu Arg Glu Leu Ala Asn Leu Val Val
                595                 600                 605

Val Gly Gly Asp Arg Arg Lys Glu Ser Lys Asp Asn Glu Glu Lys Ala
610                 615                 620

Glu Met Lys Lys Met Tyr Asp Leu Ile Glu Glu Tyr Lys Leu Asn Gly
625                 630                 635                 640

Gln Phe Arg Trp Ile Ser Ser Gln Met Asp Arg Val Arg Asn Gly Glu
                645                 650                 655

Leu Tyr Arg Tyr Ile Cys Asp Thr Lys Gly Ala Phe Val Gln Pro Ala
                660                 665                 670

Leu Tyr Glu Ala Phe Gly Leu Thr Val Val Glu Ala Met Thr Cys Gly
                675                 680                 685

Leu Pro Thr Phe Ala Thr Cys Lys Gly Gly Pro Ala Glu Ile Ile Val
                690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
                725                 730                 735

His Trp Asp Glu Ile Ser Lys Gly Gly Leu Gln Arg Ile Glu Glu Lys
            740                 745                 750

Tyr Thr Trp Gln Ile Tyr Ser Gln Arg Leu Leu Thr Leu Thr Gly Val
            755                 760                 765

Tyr Gly Phe Trp Lys His Val Ser Asn Leu Asp Arg Leu Glu Ala Arg
        770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
                805

<210> SEQ ID NO 18
<211> LENGTH: 2427
<212> TYPE: DNA
<213> ORGANISM: Arabiodopsis thaliana

<400> SEQUENCE: 18
atggcaaacg ctgaacgtat gattacccgt gtccactccc aacgcgaacg cctgaacgaa      60
accctggtgt cggaacgcaa cgaagttctg gcactgctga ccgtgtggaa agctaagggc     120
aaaggtattc tgcagcaaaa ccagattatc gcggaatttg aagccctgcc ggaacaaacc     180
cgcaaaaagc tggaaggcgg tccgtttttc gatctgctga atctacgca ggaagcgatc     240
```

```
gttctgccgc cgtgggtcgc actggcagtg cgtccgcgtc cgggcgtttg ggaatatctg    300
cgtgtcaacc tgcatgcact ggtggttgaa gaactgcagc cggctgaatt tctgcacttc    360
aaggaagaac tggttgacgg cgtcaaaaac ggtaatttta ccctggaact ggattttgaa    420
ccgttcaatg ccagtatccc gcgtccgacg ctgcataaat atattggcaa cggtgtggac    480
tttctgaatc gccatctgag cgcaaagctg ttccacgata agaatctct gctgccgctg     540
ctgaaattcc tgcgtctgca tagtcaccag ggcaagaacc tgatgctgtc gaaaaaatt    600
cagaacctga ataccctgca acacacgctg cgcaaggcgg aagaatacct ggccgaactg    660
aaaagtgaaa ccctgtacga agaattcgaa gcaaagttcg aagaaattgg cctggaacgt    720
ggctggggtg acaatgctga acgtgttctg gatatgatcc gtctgctgct ggacctgctg    780
gaagcaccgg acccgtgcac cctggaaacg tttctgggtc gcgtgccgat ggttttcaac    840
gtcgtgattc tgtccccgca tggctatttt gcacaggaca atgtgctggg ttacccggat    900
accggcggtc aggttgtcta tattctggat caagttcgtg cgctggaaat tgaaatgctg    960
cagcgcatca agcagcaagg cctgaacatc aaaccgcgta ttctgatcct gacccgtctg   1020
ctgccggatg cagttggtac cacgtgcggt gaacgtctgg aacgcgtcta tgacagcgaa   1080
tactgtgata ttctgcgtgt cccgtttcgc accgaaaagg gtattgtgcg taaatggatc   1140
agtcgcttcg aagtttggcc gtatctggaa acctacacgg aagatgcggc cgtgaactg    1200
tccaaggaac tgaatggcaa accggacctg attatcggca actatagcga tggtaatctg   1260
gtcgcatctc tgctggctca taaactgggt gtgacccagt gcacgattgc acacgctctg   1320
gaaaagacca aatatccgga ttcagacatc tactggaaaa agctggatga caaatatcat   1380
ttttcgtgtc agttcaccgc ggacattttt gccatgaacc acacggattt tattatcacc   1440
agtacgttcc aggaaatcgc gggctccaaa gaaaccgtgg gtcaatacga atcacatacc   1500
gccttcacgc tgccgggcct gtatcgtgtg gttcacggta cgatgttttt tgacccgaaa   1560
ttcaatattg tcagtccggg cgcggatatg tccatctatt ttccgtacac cgaagaaaag   1620
cgtcgcctga cgaaattcca ttcagaaatt gaagaactgc tgtactcgga cgtgaaaaac   1680
aaggaacacc tgtgtgttct gaaagataaa aagaaaccga tcctgtttac catggcccgt   1740
ctggatcgcg tgaagaatct gtcaggcctg gttgaatggt atggtaaaaa cacgcgtctg   1800
cgcgaactgg caaatctggt cgtggttggc ggtgaccgtc gcaaggaatc gaaagataac   1860
gaagaaaagg ctgaaatgaa gaaaatgtac gatctgatcg aagaatacaa gctgaacggc   1920
cagtttcgtt ggatcagctc tcaaatggac cgtgtgcgca atggcgaact gtatcgctac   1980
atttgcgata ccaagggtgc gtttgttcag ccggcactgt acgaagcttt cggcctgacc   2040
gtcgtggaag ccatgacgtg cggtctgccg acctttgcga cgtgtaaagg cggtccggcc   2100
gaaattatcg tgcatggcaa atctggtttc catatcgatc cgtatcacgg tgatcaggca   2160
gctgacaccc tggcggattt ctttacgaag tgtaaagaag acccgtcaca ctgggatgaa   2220
atttcgaagg gcggtctgca acgtatcgaa gaaaaatata cctggcagat ttacagccaa   2280
cgcctgctga ccctgacggg cgtctacggt ttttggaaac atgtgtctaa tctggatcgc   2340
ctggaagccc gtcgctatct ggaaatgttt tacgcactga gtatcgcccg ctggcacaa    2400
gccgttccgc tggcacagga cgactaa                                       2427
```

<210> SEQ ID NO 19
<211> LENGTH: 464
<212> TYPE: PRT

<213> ORGANISM: Oryza brachyantha

<400> SEQUENCE: 19

Met Glu Asn Gly Ser Ser Pro Leu His Val Ile Phe Pro Trp Leu
1               5                   10                  15

Ala Phe Gly His Leu Leu Pro Phe Leu Asp Leu Ala Glu Arg Leu Ala
            20                  25                  30

Ala Arg Gly His Arg Val Ser Phe Val Ser Thr Pro Arg Asn Leu Ala
        35                  40                  45

Arg Leu Arg Pro Val Arg Pro Ala Leu Arg Gly Leu Val Asp Leu Val
    50                  55                  60

Ala Leu Pro Leu Pro Arg Val His Gly Leu Pro Asp Gly Ala Glu Ala
65                  70                  75                  80

Thr Ser Asp Val Pro Phe Glu Lys Phe Glu Leu His Arg Lys Ala Phe
                85                  90                  95

Asp Gly Leu Ala Ala Pro Phe Ser Ala Phe Leu Asp Ala Ala Cys Ala
            100                 105                 110

Gly Asp Lys Arg Pro Asp Trp Val Ile Pro Asp Phe Met His Tyr Trp
        115                 120                 125

Val Ala Ala Ala Gln Lys Arg Gly Val Pro Cys Ala Val Leu Ile
    130                 135                 140

Pro Cys Ser Ala Asp Val Met Ala Leu Tyr Gly Gln Pro Thr Glu Thr
145                 150                 155                 160

Ser Thr Glu Gln Pro Glu Ala Ile Ala Arg Ser Met Ala Ala Glu Ala
                165                 170                 175

Pro Ser Phe Glu Ala Glu Arg Asn Thr Glu Glu Tyr Gly Thr Ala Gly
            180                 185                 190

Ala Ser Gly Val Ser Ile Met Thr Arg Phe Ser Leu Thr Leu Lys Trp
        195                 200                 205

Ser Lys Leu Val Ala Leu Arg Ser Cys Pro Glu Leu Glu Pro Gly Val
    210                 215                 220

Phe Thr Thr Leu Thr Arg Val Tyr Ser Lys Pro Val Val Pro Phe Gly
225                 230                 235                 240

Leu Leu Pro Pro Arg Arg Asp Gly Ala His Gly Val Arg Lys Asn Gly
                245                 250                 255

Glu Asp Asp Gly Ala Ile Ile Arg Trp Leu Asp Glu Gln Pro Ala Lys
            260                 265                 270

Ser Val Val Tyr Val Ala Leu Gly Ser Glu Ala Pro Val Ser Ala Asp
        275                 280                 285

Leu Leu Arg Glu Leu Ala His Gly Leu Glu Leu Ala Gly Thr Arg Phe
    290                 295                 300

Leu Trp Ala Leu Arg Arg Pro Ala Gly Val Asn Asp Gly Asp Ser Ile
305                 310                 315                 320

Leu Pro Asn Gly Phe Leu Glu Arg Thr Gly Glu Arg Gly Leu Val Thr
                325                 330                 335

Thr Gly Trp Val Pro Gln Val Ser Ile Leu Ala His Ala Ala Val Cys
            340                 345                 350

Ala Phe Leu Thr His Cys Gly Trp Gly Ser Val Val Glu Gly Leu Gln
        355                 360                 365

Phe Gly His Pro Leu Ile Met Leu Pro Ile Ile Gly Asp Gln Gly Pro
    370                 375                 380

Asn Ala Arg Phe Leu Glu Gly Arg Lys Val Gly Val Ala Val Pro Arg
385                 390                 395                 400

| | | | | | | | | | | | |
|---|---|---|---|---|---|---|---|---|---|---|---|
|Asn|His|Ala|Asp|Gly|Ser|Phe|Asp|Arg|Ser|Gly|Val|Ala|Gly|Ala|Val|
| | |405| | | |410| | | |415| |

| | | | | | | | | | | | |
|Arg|Ala|Val|Ala|Val|Glu|Glu|Glu|Gly|Lys|Ala|Phe|Ala|Ala|Asn|Ala|
| |420| | | | |425| | | | |430| |

| | | | | | | | | | | | |
|Arg|Lys|Leu|Gln|Glu|Ile|Val|Ala|Asp|Arg|Glu|Arg|Asp|Glu|Arg|Cys|
|435| | | | |440| | | | |445| |

| | | | | | | | | | | | |
|Thr|Asp|Gly|Phe|Ile|His|His|Leu|Thr|Ser|Trp|Asn|Glu|Leu|Glu|Ala|
|450| | | | |455| | | | |460| |

<210> SEQ ID NO 20
<211> LENGTH: 1395
<212> TYPE: DNA
<213> ORGANISM: Oryza brachyantha

<400> SEQUENCE: 20

```
atggaaaatg gtagcagtcc gctgcatgtt gttattttc cgtggctggc atttggtcat    60
ctgctgccgt ttctggatct ggcagaacgt ctggcagcac gtggtcatcg tgttagcttt   120
gttagcacac cgcgtaatct ggcacgtctg cgtccggttc gtccggcact gcgtggtctg   180
gttgatctgg ttgcactgcc gctgcctcgt gttcatggtc tgccggatgg tgccgaagca   240
accagtgatg ttccgtttga aaaatttgaa ctgcaccgca agcatttga tggcctggct   300
gcaccgttta gcgcatttct ggatgcagca tgtgccggtg ataaacgtcc ggattgggtt   360
attccggatt ttatgcatta ttgggttgca gcagcagcac agaaacgtgg tgttccgtgt   420
gcagttctga ttccgtgtag cgcagatgtt atggcactgt atggtcagcc gaccgaaacc   480
agcaccgaac agccggaagc aattgcacgt agcatggcag cagaagcacc gagctttgaa   540
gcagaacgta ataccgaaga atatggtaca gccggtgcaa gcggtgttag cattatgacc   600
cgttttagtc tgaccctgaa atggtcaaaa ctggttgccc tgcgtagctg tccggaactg   660
gaaccgggtg tttttaccac actgacccgt gtttatagca aaccggttgt gccgtttggt   720
ctgctgcctc cgcgtcgtga tggtgcacat ggtgttcgta aaaatggtga agatgatggt   780
gccattattc gttggctgga tgaacagcct gcaaaaagcg ttgtttatgt tgcactgggt   840
agcgaagcac cggtttcagc cgatctgctg cgtgaactgg cacatggtct ggaattagca   900
ggcacccgtt ttctgtgggc tctgcgtcgt cctgccggtg ttaatgatgg tgatagcatt   960
ctgccgaatg gttttctgga acgtaccggt gaacgcggtc tggttaccac cggttgggtt  1020
ccgcaggtta gtattctggc ccatgcagca gtttgtgcat ttctgaccca ttgtggttgg  1080
ggtagcgttg ttgaaggttt acagtttggc catccgctga ttatgctgcc gattattggt  1140
gatcagggtc cgaatgcacg ctttctggaa ggtcgtaaag ttggtgttgc agttccgcgt  1200
aaccatgcag atggtagctt tgatcgtagc ggtgttgccg gtgccgttcg tgcagttgca  1260
gttgaagaag aaggtaaagc ctttgcagca aatgcccgta aactgcaaga aattgttgca  1320
gatcgtgaac gtgatgaacg ttgtaccgat ggttttattc atcatctgac cagctggaat  1380
gaactggaag cataa                                                   1395
```